United States Patent [19]

Taylor et al.

[11] Patent Number: 5,728,095
[45] Date of Patent: Mar. 17, 1998

[54] METHOD OF USING AN ORTHOPAEDIC FIXATION DEVICE

[75] Inventors: Harold S. Taylor; John Charles Taylor, both of Memphis, Tenn.

[73] Assignee: Smith & Nephew, Inc., Memphis, Tenn.

[21] Appl. No.: 726,713

[22] Filed: Oct. 7, 1996

Related U.S. Application Data

[63] Continuation-in-part of Ser. No. 396,624, Mar. 1, 1995, abandoned.

[51] Int. Cl.[6] .................................................. A61B 17/60
[52] U.S. Cl. ........................... 606/54; 606/56; 606/57; 606/59
[58] Field of Search .................................. 606/54, 55, 56, 606/57, 58, 59, 60, 61

[56] References Cited

U.S. PATENT DOCUMENTS

| | | | |
|---|---|---|---|
| 1,308,799 | 7/1919 | Masland . | |
| 2,055,024 | 9/1936 | Bittner, Jr. | 128/85 |
| 2,250,417 | 7/1941 | Ettinger | 128/92 |
| 2,391,537 | 12/1945 | Anderson | 128/84 |
| 2,487,989 | 11/1949 | Sherburne | 287/88 |
| 3,176,805 | 4/1965 | Gandy | 189/28 |
| 3,727,610 | 4/1973 | Riniker | 128/92 A |

(List continued on next page.)

FOREIGN PATENT DOCUMENTS

| | | |
|---|---|---|
| WO91/06253 | 5/1991 | European Pat. Off. . |
| WO92/17313 | 10/1992 | European Pat. Off. . |
| 0 589 565 | 3/1994 | European Pat. Off. . |
| 25 46 046 | 4/1977 | Germany . |
| 820813 | 4/1981 | U.S.S.R. . |
| 1 255 118 | 9/1986 | U.S.S.R. . |
| 1 519 673 | 11/1989 | U.S.S.R. . |
| 108119 | 7/1917 | United Kingdom . |
| 2077 847 | 12/1981 | United Kingdom . |

OTHER PUBLICATIONS

*Monticelli Spinelli® External Fixation System*, cover and pp. 1–28.

(List continued on next page.)

*Primary Examiner*—Michael Buiz
*Assistant Examiner*—Daphna Shai
*Attorney, Agent, or Firm*—Earl M. Douglas

[57] ABSTRACT

An external fixator for positioning a first element or the like relative to a second element or the like. The external fixator includes a first base for mounting to the first element; a second base for mounting to the second element; a plurality of adjustable effective length struts; connector structure for rotatably attaching the first ends of a first pair of struts relative to one another and relative to the first base; connector structure for rotatably attaching the first ends of a second pair of struts relative to one another and relative to the first base; connector structure for rotatably attaching the first ends of a third pair of struts relative to one another and relative to the first base; connector structure for rotatably attaching the second ends of the first pair of struts relative to one another and relative to the second base; connector structure for rotatably attaching the second ends of the second pair of struts relative to one another and relative to the second base member; and connector structure for rotatably attaching the second ends of the third pair of struts relative to one another and relative to the second base member.

A unique method of using an external fixation device to reposition a first bone segment relative to a second bone segment is claimed herein. The unique method of using the external fixation device of the current invention includes attaching said first base member to said first bone segment, attaching said second base member to said second bone segment, and adjusting the effective length of at least one of the struts, thereby repositioning said first bone segment relative to said second bone segment.

49 Claims, 26 Drawing Sheets

U.S. PATENT DOCUMENTS

| | | | |
|---|---|---|---|
| 3,941,123 | 3/1976 | Volkov et al. | 128/84 B |
| 3,977,397 | 8/1976 | Kalnberz et al. | 128/92 A |
| 4,033,340 | 7/1977 | Kalnberz | 128/92 A |
| 4,100,919 | 7/1978 | Oganesyan et al. | 128/42 B |
| 4,112,935 | 9/1978 | Latypov et al. | 128/69 |
| 4,308,863 | 1/1982 | Fischer | 128/92 A |
| 4,361,144 | 11/1982 | Slätis | 128/92 A |
| 4,482,266 | 11/1984 | Kaneko | 403/135 |
| 4,483,334 | 11/1984 | Murray | 128/92 A |
| 4,502,473 | 3/1985 | Harris et al. | 128/92 A |
| 4,541,422 | 9/1985 | de Zbikowski | 128/92 A |
| 4,570,625 | 2/1986 | Harris et al. | 128/92 G |
| 4,615,338 | 10/1986 | Ilizarov et al. | 128/92 A |
| 4,620,533 | 11/1986 | Mears | 128/92 Z |
| 4,624,249 | 11/1986 | Alvarez Cambras | 128/92 ZK |
| 4,628,922 | 12/1986 | Dewar | 128/92 Z |
| 4,662,365 | 5/1987 | Gotzen et al. | 128/92 ZW |
| 4,768,524 | 9/1988 | Hardy | 128/92 Z |
| 4,889,111 | 12/1989 | Ben-Dov | 128/419 F |
| 4,928,546 | 5/1990 | Walters | 74/479 |
| 4,973,331 | 11/1990 | Pursley et al. | 606/54 |
| 4,988,244 | 1/1991 | Sheldon et al. | 409/132 |
| 5,028,180 | 7/1991 | Sheldon et al. | 409/201 |
| 5,062,844 | 11/1991 | Jamison et al. | 606/54 |
| 5,170,790 | 12/1992 | Lacoste et al. | 138/660.01 |
| 5,180,380 | 1/1993 | Pursley et al. | 606/54 |
| 5,209,750 | 5/1993 | Stef | 606/54 |
| 5,259,710 | 11/1993 | Charles | 409/235 |
| 5,275,598 | 1/1994 | Cook | 606/54 |
| 5,354,158 | 10/1994 | Sheldon et al. | 409/201 |
| 5,388,935 | 2/1995 | Sheldon | 409/201 |
| 5,405,347 | 4/1995 | Lee et al. | 606/54 |
| 5,461,515 | 10/1995 | Sorce | 359/872 |
| 5,466,085 | 11/1995 | Sheldon et al. | 403/157 |
| 5,490,784 | 2/1996 | Carmein | 434/55 |

OTHER PUBLICATIONS

Richards Medical Company, *Richards External Fixation Systems*, 1983, 8 pages.

Hex–Fix Surgical Technique brochure, title page and pp. 1–7.

Smith & Nephew Richards Inc., *The Original Ilizarov System, The Ilizarov External Fixator General Surgical Technique Brochure*, 1988.

The Ilizarov Method Bioskills Workshop Handbook, Essential Concepts & Methodology for Application of the Ilizarov Technique, 26 pages.

Geng, Z.J., Haynes, L.S., "A 3–2–1 Kinematic Configuration Of A Stewart Platform And Its Application to Six Degree Of Freedom Pose Measurements", *Robotics & Computer–Integrated Manufacturing*, vol. 11, No. 1, 1994, pp. 23–34.

Sreenivasan, S.V., Waldron, K.J., Nanua, P., "Closed–Form Direct Displacement Analysis Of A 6–6 Stewart Platform", *Mech. Mach Theory*, vol. 29, No. 6, 1994, pp. 855–864.

Dasgupta, B., Mruthyunjaya, T.S., "A Canonical Formulation of The Direct Position Kinematics Problem For A General 6–6 Stewart Platform", *Mech. Mach. Theory*, vol. 29, No. 6, 1994, pp. 819–827.

Liu, K., Lewis, F.L., Fitzgerald, M., "Solution Of Nonlinear Kinematics Of A Parallel–Link Constrained Stewart Platform Manipulator", *Circuits Systems Signal Process*, vol. 13, No. 2–3, 1994, pp. 167–183.

Zhuang, H., Roth, Z.S., "Method For Kinematic Calibration Of Stewart Platforms", *Journal of Robotic Systems*, 10(3), 1993, pp. 391–405.

Stoughton, R.S., Arai, T., "A Modified Sewart Platform Manipulator With Improved Dexterity", *IEEE Transactions On Robotics And Automation*, vol. 9, No. 2, Apr. 1993.

Wen, F., Liang, C., "Displacement Analysis Of The 6–6 Stewart Platform Mechanisms", *Mech Mach Theory*, vol. 29, No. 4, 1994, pp. 547–557.

Zhang, C., Song, S., "Forward Position Analysis Of Nearly General Stewart Platforms", *Journal of Mechanical Design*, vol. 116, pp. 54–60, Mar. 1994.

Nair, R., Maddocks, J.H., "On The Forward Kinematics Of Parallel Manipulators", *The International Journal of Robotics Research*, vol. 13, No. 2, Apr. 1994, pp. 171–188.

Dasgupta, B., Mruthyunjaya, T.S., "Letter To The Editor", *Mech. Mach. Theory*, vol. 29, No. 2., 1994, p. 341.

Fenton, R.G., "Response", *Mech. Mach. Theory*, vol. 29, No. 2, 1994, p. 343.

Liu, K., Fitzgerald, J.M., Lewis, F.L., "Kinematic Analysis of a Stewart Platform Manipulator", *IEEE Transaction On Industrial Electronics*, vol. 40, No. 2, Apr. 1993, pp. 282–293.

Raghavan, M., "The Stewart Platform of General Geometry Has 40 Configurations", *Journal of Mechanical Design*, vol. 115, Jun. 1993, pp. 277–282.

Ji, Z., "Dynamics Decomposition for Stewart Platform", *Journal of Mechanical Design*, vol. 116, Mar. 1994, pp. 67–69.

Chen, N., Song, S., "Direct Position Analysis of the 4–6 Stewart Platforms", *Journal of Mechanical Design*, vol. 116, Mar. 1994, pp. 61–66.

Wohlhart, K., "Displacement Analysis Of The General Spherical Stewart Platform", *Mech. Mach. Theory*, vol. 29, No. 4, 1994, pp. 581–589.

Nanua, P., Waldron, K.J., and Murthy, V., "Direct Kinematic Solution of a Stewart Platform", *IEEE Transactions On Robotics And Automation*, vol. 6, No. 4, Aug. 1990, pp. 438–443.

Fichter, E.F., "A Stewart Platform–Based Manipulator: General Theory and Practical Construction", *International Journal of Robotics Research*, vol. 5, No. 2, pp. 157–182.

*Techniques In Orthopaedics, Basic Ilizarov Techniques*, vol. 5, No. 4, Dec. 1990, 4 pages.

Catagni, M.A., Malzev, V., Kirienko, Al., *Advances In Ilizarov Apparatus Assembly*, 1994.

VARIAX™, Giddings & Lewis® Automation Technology, 4 pages.

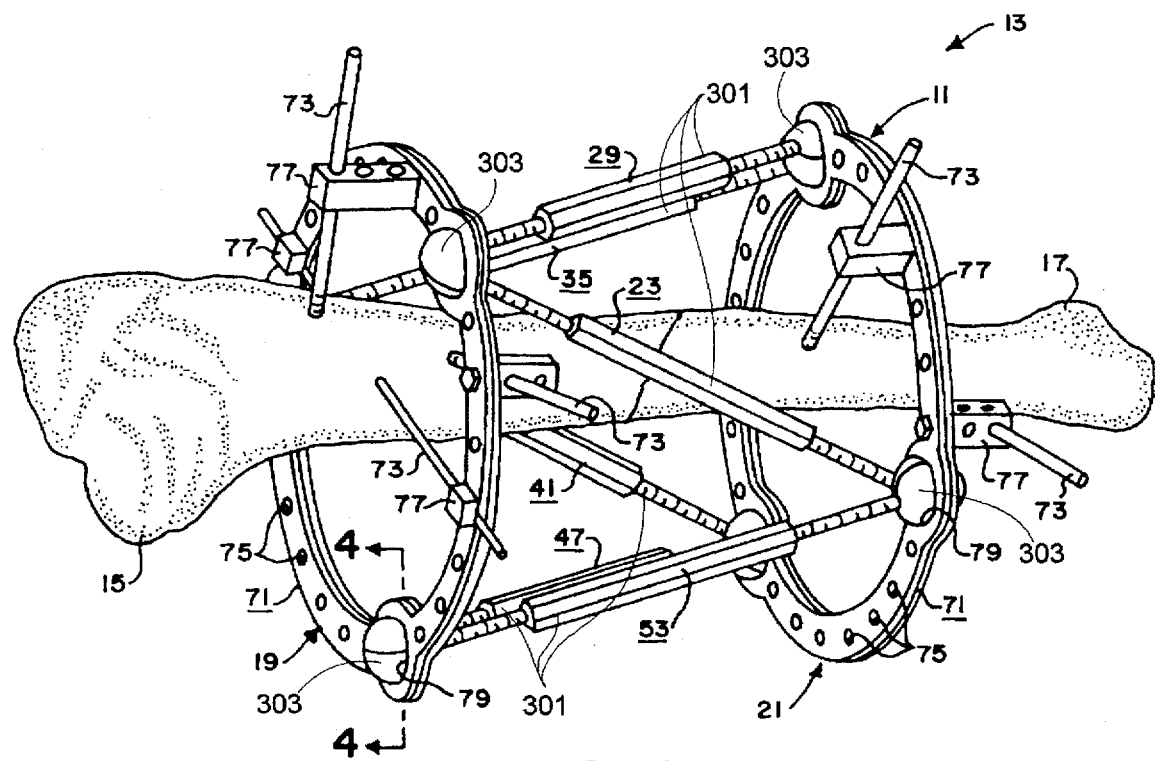
FIG. 1
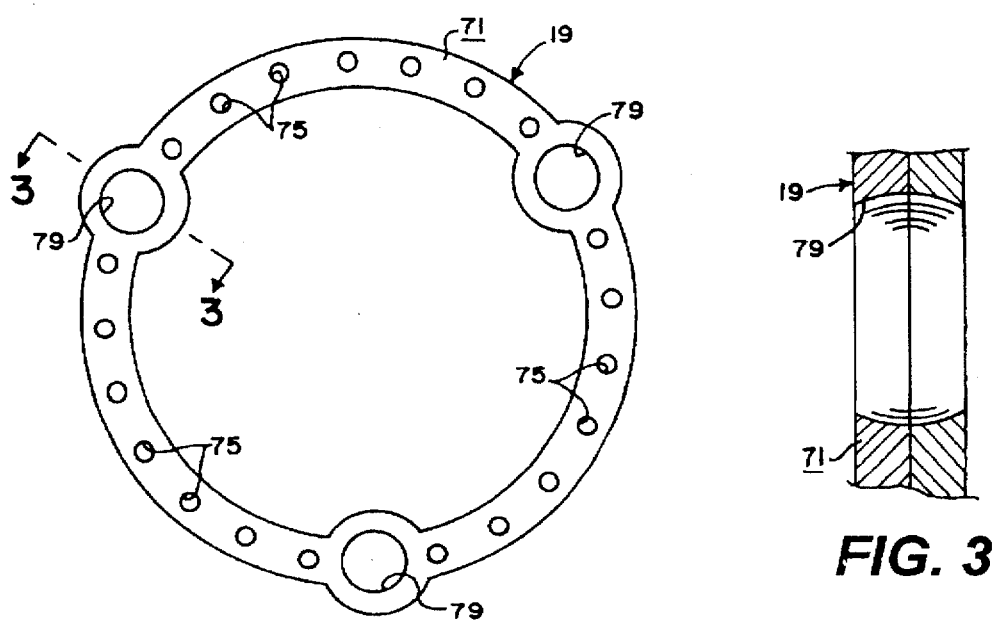
FIG. 2
FIG. 3

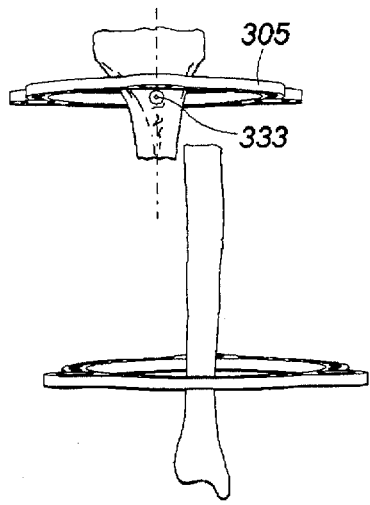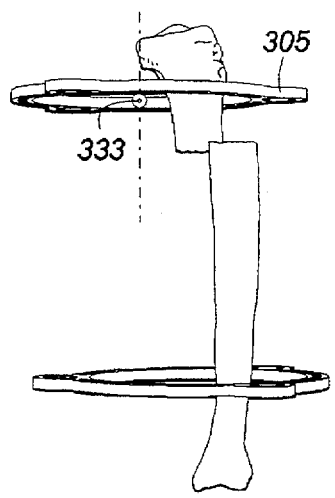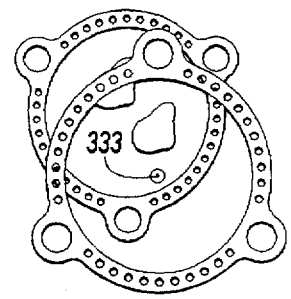
FIG. 34A    FIG. 34B    FIG. 34C
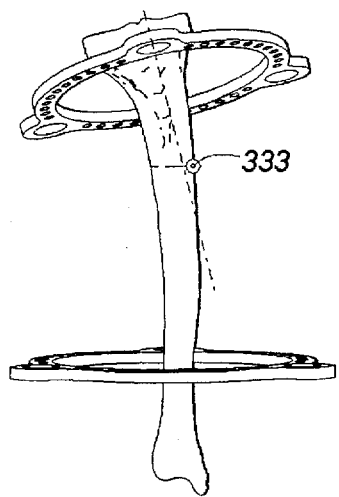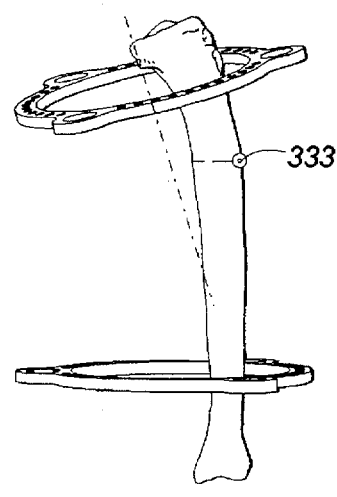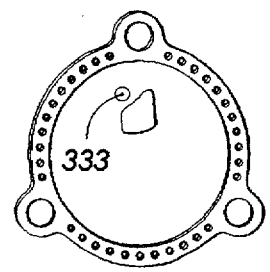
FIG. 35A    FIG. 35B    FIG. 35C (I)        (II)

METHOD OF USING AN ORTHOPAEDIC FIXATION DEVICE

This is a continuation-in-part of application Ser. No. 08/396,624 filed on 1 Mar., 1995, now abandoned.

BACKGROUND OF THE INVENTION

1. Field of the Invention

The present invention relates, in general, to a device that allows complete repositioning of two members relative to one another and, more specifically, to an improved orthopedic external fixator including a mechanism that allows two bone elements or portions to be fixed relative to one another while allowing complete repositioning of the two bone elements or portions relative to one another.

2. Background Art

It is often necessary to realign, reposition and/or securely hold two elements relative to one another. For example, in the practice of medicine, bone fragments and the like must sometimes be aligned or realigned and repositioned to restore boney continuity and skeletal function, etc. At times this may be accomplished by sudden maneuver, usually followed by skeletal stabilization with cast, plate and screws, intramedullary devices, or external skeletal fixators.

A bone fragment can be moved, in general, from its original position as in a nonunion or malunion or from its intended position as in congenital deformities along six separate axes, a combination of three orthogonal translational axes (e.g., typical "X," "Y" and "Z" axes) and three orthogonal rotational axes (e.g., rotation about such typical "X," "Y" and "Z" axes).

Certain boney skeletal injuries or conditions are sometimes treated with an external device that is attached to the boney skeleton with threaded and/or smooth pins and/or threaded and/or smooth and/or beaded wires. Such constructs are commonly referred to as orthopedic external fixators or external skeletal fixators. External fixators may be utilized to treat acute fractures of the skeleton, soft tissue injuries, delayed union of the skeleton when bones are slow to heal, nonunion of the skeleton when bones have not healed, malunion whereby broken or fractured bones have healed in a malposition, congenital deformities whereby bones develop a malposition, and bone lengthening, widening, or twisting.

External fixators vary considerably in design and capabilities, and may include multiple or single bars or rods, and a plurality of clamps for adjustably securing the bars to pins or wires which are, in turn, joined to the boney skeleton. The pins or wires may extend completely through the boney skeleton extending out each side of the limb or may extend through the boney skeleton and out one side of the limb. Pins which extend completely through the boney skeleton and out both sides of the limb are commonly referred to as "transfixation pins." Pins which extend through the boney skeleton and out only one side of the limb are commonly referred to as "half pins." Such external fixators may be circumferential for encircling a patient's body member (e.g., a patient's femur), or may be unilateral for extending along one side of a patient's body member. More that one unilateral external fixator can be applied to the same length of the patient's body member. Materials for fixators also vary, including metals, alloys, plastics, composites, and ceramics. External fixators vary in their ability to accommodate different spatial relations between the pin and bar.

Prior art external fixators stabilize bone fragments by holding the fragments in a relatively fixed spatial relation. Some of the more completely adjustable external fixators allow the physician to reorient one fragment with respect to the other along all six axes in an acute motion, usually by loosening one or more clamps and effecting the corrective motion manually and retightening clamps to hold the fragments stably.

A circumfrential external fixator system was disclosed by G. A. Ilizarov during the early 1950's. The Ilizarov system include at least two rings or "halos" that encircle a patient's body member (e.g., a patient's leg), connecting rods extending between the two rings, transfixion pins that extend through the patient's boney structure, and connectors for connecting the transfixion pins to the rings. Use of the Ilizarov system to deal with angulation, translation and rotation is disclosed in "Basic Ilizarov Techniques," *Techniques in Orthopaedics®*, Vol. 5, No. 4, December 1990, pages 55–59.

Mears, U.S. Pat. No. 4,620,533, issued Nov. 4, 1986, discloses a unilateral external fixator system including a plurality of fixation pins attached to at least one rigid bar through adjustable clamps having articulating bails which allow rotational adjustment of each pin or bar.

Stef, U.S. Pat. No. 5,209,750, issued May 11, 1993, discloses a unilateral external fixator system including an orthopedic brace for rigidly connecting groups of pins screwed into a long bone for the reduction of a fracture of the long bone. The brace includes a telescopic support made up of an elongated tube and an elongated rod slidable within the tube. A first plate is attached to the outer end of the tube and a second plate is attached to the outer end of the rod Third and fourth plates are adjustably attached to the first and second plates, respectively, by way of threaded rods and ball-and-socket joints. Jaws are attached to each third and fourth plate to secure the pins to the brace, Prior art orthopedic external fixators differ in their ability to move or adjust one bone fragment with respect to the other in a gradual fashion. Some allow gradual translation, others allow gradual rotation about two axes. The Ilizarov system can provide an external fixation device that could provide gradual correction along and about six axes; however such a device would require many parts and would be relatively complicated to build and use in a clinical situation.

Often orthopedic external fixators such as Ilizarov fixators must be modified later on after their initial application. Such modification may be necessary to convert from one correctional axis to another or to convert from an initial adjustment type of fixator to a weight bearing type of fixator, some of the correctional configurations not being stable enough for weight bearing.

More simplistic external fixators may accomplish a rotation of fragments about a center of rotation contained on the external fixator. This may or may not correspond to the center of rotation necessary to fully correct the deformity by angular correction alone. In no circumstances will a center of rotation confined to the external fixator create a virtual center of rotation remote to the external fixator as is frequently required in the treatment of these deformities. Some orthopedic external fixators utilize a simple hinge which cannot create a center of rotation remote to its mechanism. The Ilizarov system provides a circumferential encompassing type fixator that is more universal in that it permits the placement of the hinge axis around the bone, but does not allow rotation about an axis remote to its mechanism. A focal hinge made of an arc segment of gear or track with a following carriage can create a center of rotation remote to the mechanism but may not be applicable to certain situations where because of anatomy or preference the mechanism is to be applied to the concavity of a deformity, especially a severe deformity where there is no space to apply the long arc segment of gear or track necessary to fully correct the deformity.

Anderson, U.S. Pat. No. 2,391,537, issued Dec. 25, 1945, discloses an orthopedic external fixator for fracture reduction including a pair of hollow tubes telescopically joined together, a plurality of pins for transfixing bone elements, a first fixation unit slidably mounted on one of the tubes for connecting a pair of the transfixion pins to that tube, and a second fixation unit attached to the end of the other tube for connecting a pair of the transfixation pins to that tube. One of the tubes is telescopically mounted within the other tube. A threaded adjusting shaft is mounted within the tubes and can be manually rotated by way of a wrench head located at the outer end of one of the tubes. Rotation of the shaft causes a nut nonrotatably located within the tubes to move longitudinally along the shaft. Coil springs located within the tubes on either side of the nut transfer longitudinal movement of the nut to the tubes while permitting a certain desired yielding and eliminating any perfectly solid and hard contact. A geared mechanism allows for correction of rotational deformity, utilizing an arc segment of gear and a mating carriage with corresponding pinion.

A "Stewart platform" is a fully parallel mechanism used in flight and automotive simulators, robotic end-effectors, and other applications requiring spatial mechanisms with high structural stiffness; and includes a base platform, a top platform, and six variable limbs extending between the base and top platforms. See S. V. Sreenivasan et al., "Closed-Form Direct Displacement Analysis of a 6—6 Stewart Platform," *Mech. Mach. Theory*, Vol. 29, No. 6, pp. 855–864, 1994.

Nothing in the known prior art discloses or suggests the present invention. For example, nothing in the known prior art discloses a fixator that can be adjusted in six axes by changing strut lengths only, without requiring joints to be unclamped, etc. Further nothing in the known prior art discloses or suggests a mechanism including, in general, a first member or swash plate for attachment relative to a first element; a second member or swash plate for attachment relative to a second element; an adjustable effective length first strut having a first end movably attached to the first member and a second end movably attached to the second member; an adjustable effective length second strut having a first end movably attached to the first member and a second end movably attached to the second member; an adjustable effective length third strut having a first end movably attached to the first member and a second end movably attached to the second member; an adjustable effective length fourth strut having a first end movably attached to the first member and a second end movably attached to the second member; an adjustable effective length fifth strut having a first end movably attached to the first member and a second end movably attached to the second member; and an adjustable effective length sixth strut having a first end movably attached to the first member and a second end movably attached to the second member, with the first ends of the first and second struts joined relative to one another so that movement of the first end of one of the first and second struts will cause a corresponding movement of the first end of the other strut, with the first ends of the third and fourth struts joined relative to one another so that movement of the first end of one of the third and fourth struts will cause a corresponding movement of the first end of the other strut, with the first ends of the fifth and sixth struts joined relative to one another so that movement of the first end of one of the fifth and sixth struts will cause a corresponding movement of the first end of the other strut, with the second ends of the first and sixth struts joined relative to one another so that movement of the second end of one of the first and sixth struts will cause a corresponding movement of the second end of the other strut, with the second ends of the second and third struts joined relative to one another so that movement of the second end of one of the second and third struts will cause a corresponding movement of the second end of the other strut, with the second ends of the fourth and fifth struts joined relative to one another so that movement of the second end of one of the fourth and fifth struts will cause a corresponding movement of the second end of the other strut.

SUMMARY OF THE INVENTION

The present invention provides a novel device that allows two elements to be positioned relative to one another while allowing complete repositioning of the two elements relative to one another. A basic concept of the present invention is to provide an eight member device that allows two elements to be positioned or fixed relative to one another while allowing complete repositioning of the two elements relative to one another. The present invention further includes a novel method of using the device described herein.

The present invention includes, in general, a first member or swash plate for attachment relative to a first element; a second member or swash plate for attachment relative to a second element; an adjustable effective length first strut having a first end movably attached to the first member and a second end movably attached to the second member; an adjustable effective length second strut having a first end movably attached to the first member and a second end movably attached to the second member; an adjustable effective length third strut having a first end movably attached to the first member and a second end movably attached to the second member; an adjustable effective length fourth strut having a first end movably attached to the first member and a second end movably attached to the second member; an adjustable effective length fifth strut having a first end movably attached to the first member and a second end movably attached to the second member; and an adjustable effective length sixth strut having a first end movably attached to the first member and a second end movably attached to the second member. The first ends of the first and second struts are joined relative to one another so that movement of the first end of one of the first and second struts will cause a corresponding movement of the first end of the other strut. The first ends of the third and fourth struts are joined relative to one another so that movement of the first end of one of the third and fourth struts will cause a corresponding movement of the first end of the other strut. The first ends of the fifth and sixth struts are joined relative to one another so that movement of the first end of one of the fifth and sixth struts will cause a corresponding movement of the first end of the other strut. The second ends of the first and sixth struts are joined relative to one another so that movement of the second end of one of the first and sixth struts will cause a corresponding movement of the second end of the other strut. The second ends of the second and third struts are joined relative to one another so that movement of the second end of one of the second and third struts will cause a corresponding movement of the second end of the other strut. The second ends of the fourth and fifth struts are joined relative to one another so that movement of the second end of one of the fourth and fifth struts will cause a corresponding movement of the second end of the other strut.

In accordance with the unique method of using the device of the current invention, deformities can be substantially corrected by simply adjusting the length of one or more of the adjustable struts. By fully characterizing the skeletal deformity, determining the appropriate device size, and anticipating the position of the device on the limb, the surgeon can substantially correct complex deformities by using the unique method of the current invention. Also, fracture fragments can undergo delayed reduction without device or pin revision. Skeletal deformity is completely characterized by measuring six deformity parameters: the three projected angles (rotations) and three projected translations between major fragments. The signs (+/−) of these angles and translations are determined by the mathematical convention of coordinate axes and the right-hand rule. The three device parameters consist of proximal and distal ring diameters and neutral strut length. Four mounting parameters are anticipated before surgery for chronic situations and measured radiographically and clinically after surgery for acute fractures. They are anterior-posterior, lateral-medial, axial, and rotary Eccentricities. These parameters are used in a general deformity equation in accordance with the novel method of the current invention to provide the appropriate strut lengths required to correct a deformity.

One object of the present invention is to provide a device that allows complete repositioning of two or more elements such as two or more bone fragments.

Another object of the present invention is to provide a device that allows sudden repositioning of two or more elements to be accomplished predictably and which may be left in place for additional time or may be replaced by other means of stabilization.

Another object of the present invention is to provide a device that allows gradual repositioning of two or more elements over an extended period of time either in an incremental fashion with discreet adjustments or continuous motion if motorized, etc.

Another object of the present invention is to provide a device that allows a slow controlled reposition of two or more elements.

Another object of the present invention is to provide a device that is capable of correcting all six degrees of freedom and at no time is unstable to move grossly unless the gross motion locks are loosened.

Another object of the present invention is to provide a device that allows relative repositioning of two or more elements by changing the effective lengths of six similar struts, either gradually or suddenly.

Another object of the present invention is to provide a device that can move one fragment with respect to the other in six orthogonal degrees of freedom, a combination of three orthogonal translational axes (e.g., typical "X," "Y" and "Z" axes) and three orthogonal rotational axes (e.g., rotation about such typical "X," "Y" and "Z" axes), limited in extent of relative repositioning only by the physical constraints of the device.

Another object of the present invention is to provide a device that is relatively compact, to some extent telescoping upon itself.

Another object of the present invention is to provide a device that is universal in that it can be used for any situation requiring relative motion between elements including compression (shortening), distraction (lengthening), translation, angulation, or rotation and any combination of such movements.

Another object of the present invention is to provide a device that can create a center of rotation of the elements to be fixed relative to one another that may be remote to the device itself, but may also allow rotation within or close to the device confines.

Another object of the present invention is to provide a device that allows coarse and/or fine adjustment of the relative position of two or more elements.

Another object of the present invention is to provide a mechanism for producing a prescribed relative change in position between two bone fragments in conjunction with external fixation of the bone fragments for correction of angular and translational displacements of acutely fractured fragments, correction of angular and translational deformities in nonunion and malunion, etc.

Another object of the present invention is to provide a device having a universal repositioning character.

Another object of the present invention is to provide a device having an overall simplicity of construction and use unlike other external fixators.

Another object of the present invention is to provide a device having six similar struts which can be adjusted in length and attached at either end by passive, clamping or non-clamping joint connections to two end members.

Another object of the present invention is to provide a device that is self locking and not prone to spontaneous slippage due to the inherent stability of strut adjustment mechanisms to resist rotation when loaded in tension or compression. The strut adjustment mechanism could include turnbuckles, gear and rack, screw and nut, or hydraulic cylinder, etc., and may include means of coarse and fine adjustment thereby allowing rapid approximation and subsequent precise adjustments.

Another object of the present invention is to provide a device that utilizes struts that are purposely angled with respect to the long axis. This angulation provides mechanical characteristic which allows the present invention to correct all six degrees of freedom.

Another object of the present invention is to provide a device that can be adjusted to move elements such as bone fragments from one relative position to another without losing control of the elements while making all degrees of freedom always available without having to reposition element fixation pins or wires and without having to reposition the point of attachment of the struts.

Another object of the present invention is to provide a device that can be completely repositioned by changing the effective lengths of the struts by adjusting the effective length of one or more struts.

Another object of the present invention is to provide a device that is especially designed for, but not limited to, securely holding bone fragments, repositioning bone fragments, and reproducing joint motion.

Another object of the present invention is to provide a device that may be used to reposition any two bodies relative to each other.

Another object of the present invention is to provide a device that can also be used as a telescope device with the primary mirror attached to one swash plate and the secondary mirror attached to the opposite swash plate with the six struts acting not only as a stabilizing device but also provide means for aligning and positioning the mirrors/lenses with respect to each other.

Another object of the present invention is to provide a device that can be used in the laboratory for positioning components, and in construction to reposition two members.

Another object of the present invention is to provide a device that can be considered both fixator and mechanism. To the extent that each combination of lengths for the six struts yields a stable construct, the present invention provides a stabilizing device for bone fragments and functions as a skeletal external fixation device. To the extent that changing the effective lengths of one or more of the struts results in relative motion between the swash plates, the present invention provides a mechanism for moving bone fragments.

Another object of the present invention is to provide a device that can be used to reestablish skeletal joint motion after injury or disease by being attached to either side of a skeletal joint to reproduce not only hinge type motion most like the elbow or ankle joints, but more complex motions such as those with changing instant centers of rotation, or even spherical motion like the hip by allowing one bone fragment to be moved along six independent axes with respect to another bone fragment.

Another object of the present invention is to provide a device that does not have to be mounted exactly along a particular axis at the time of initial attachment or surgery.

Another object of the present invention is to provide a device in which the orientation of the device with respect to the skeletal joint can be determined after the device is applied and the relative lengthening or shortening of the six struts necessary to provide the preferred motion can then be determined.

Another object of the present invention is to provide a device having ball joints composed of two hemispheres, or a hyperhemisphere in conjunction with a hypohemisphere.

Another object of the present invention is to provide a device having three or more bodies contained with a spherical socket.

Another object of the present invention is to provide a device that operates as a true parallel and simultaneous manipulator.

Another object of the present invention is to provide a device in which the only adjustments necessary for correcting one or six orthogonal deformities is to simply change strut lengths, regardless of whether a translation or angulation or combination of up to three orthogonal rotations and three orthogonal translations is desired.

Another object of the present invention is to provide a device which is not limited to "serial" mechanisms or steps to accomplish a six axis correction.

Another object of the present invention is to provide a device in which all the struts are free to rotate at each end.

Another object of the present invention is to provide a device which allows six axes correction without limiting the correction to a sudden correction in which a number of joints or all of the joints are loosened, the device moved, and the joints then retightened.

Another object of the present invention is to provide a device in which all coupling joints (strut to end plate) are not clamped while the device, even though not clamped, provides stability by virtue of its geometry with angled struts.

Another object of the present invention is to provide a device that uses passive unclamped joints to couple six struts to two end plates or bodies.

Another object of the present invention is to provide a device which can correct a six axis deformity in a controlled fashion.

Another object of the present invention is to provide a device having six angled struts with the joints at the end of each strut left free to rotate and with the geometry of the six strut fixator providing a stable device.

Another object of the present invention is to provide a device that allows slow controlled repositioning of two or more bone fragments only during lengthening along the long axis and also during correction of angular deformity.

Another object of the present invention is to provide a device that allows gradual or sudden adjustment of the effective length thereof.

Another object of the present invention is to provide a device that allows biologically compatible relative velocities between bone fragments on the order of one millimeter per day.

Another object of the present invention is to provide a device that can predictably and reproducibly cause small displacements between bone fragments.

Another object of the present invention is to provide a device that allows coordinate transformation based on mathematical computation of only three points on one end plate and resulting changes in length of six struts spanning only six points.

Another object of the present invention is to provide a device that functions, kinematically speaking, generally as a parallel manipulator in that the basic device is capable of accomplishing a simultaneous six degree of freedom motion of bone fragments relative to one another.

Another object of the present invention is to provide a device including two base members jointed by a plurality of adjustable effective length struts with the ends of each strut coupled to a base member by a shared joint (i.e., a joint shared with the end of another strut) or a non-shared joint.

Another object of the present invention is to provide an external fixator that allows a surgeon to reposition bone fragments without having to first loosen a plurality of joints, then reposition the bone fragments, and then retightened the plurality of joints.

Another object of the present invention is to provide a device having two base members and at least six struts joining the two base members together with shared vertices with six shared vertices or coupling of struts to the base members for repositioning objects including bone fragments.

Another object of the present invention is to provide a device having a ball-and-socket joint with four degrees of freedom (i.e., in addition to rotation about three orthogonal axes as typically accomplished by conventional ball-and-socket joints, the bail-and-socket joint of the present invention includes hemispheres which are additionally free to rotate about an axis perpendicular to the face of each hemisphere passing through the center of the hemispheres).

Another object of the present invention is to provide a device having struts that are attached to end or base members by couplings which permits rotation (the exact number of rotations being determined by the type of coupling), that maintains its position until one or more strut lengths are adjusted, that permits a gradual predictable corrective motion, that has stability provided by purposely angling the struts to create a "triangle" that prevents motion along the orthogonal axes, and not by creating a clamping force at the couplings.

Another object of the present invention is to provide a device that does not require the joints between the struts and base members to be clamped to prevent unwanted motion or to prevent motion after reduction.

Another object of the present invention is to provide a device that maximizes the amount of space on the end plates for attachment of pin clamps and eases space restrictions.

Another object of the present invention is to provide a device that can be used in small sizes in situations where space is at a premium, for example, in external fixation of children's bones.

Another object of the present invention is to provide external fixation, telescopes, laboratory or construction jacks.

Another object of the present invention is to provide a new use for a Stewart platform. More specifically, another object of the present invention is to use a Stewart platform in orthopedics to secure first and second bone elements relative to one another.

Another object of the present invention is to provide a novel technique for using the device of the present invention. More specifically, it is an object of the present invention to provide a technique for systematically determining the appropriate strut lengths necessary to use the device of the present invention to correct a deformity.

Another object of the present invention is to provide a novel technique for using the device of the present invention to correct acute deformities.

Another object of the present invention is to provide a novel technique for using the device of the present invention to correct chronic deformities.

Another object of the present invention is to provide a novel systematic technique that can be done on a computer or calculator for determining the appropriate e strut lengths necessary to use the device of the present invention to correct a deformity.

Another object of the present invention is to provide a novel technique for using the device of the present invention in manner that minimizes risks to structures such as nerves surrounding the deformity.

BRIEF DESCRIPTION OF THE DRAWINGS

FIG. 1 is a perspective view of a first preferred embodiment of the external fixator of the present invention shown in combination with other elements of an orthopedic external fixator and a fractured tibia.

FIG. 2 is an end elevational view of one end plate of the external fixator of FIG. 1.

FIG. 3 is a sectional view substantially as taken on line 3—3 of FIG. 2 on an enlarged scale with portions thereof omitted for clarity.

FIG. 34 is a diagram illustrating a preferred selection of an origin in accordance with the method of the current invention, and includes an anterior-posterior view (A), a lateral-medial view (B), and a cross-sectional axial view (C) of the base members of the current invention mounted on a fractured tibia.

FIG. 35 is a diagram illustrating a preferred selection of an origin in accordance with the method of the current invention, and includes an anterior-posterior view (A), a lateral-medial view (B), and a cross-sectional axial view (C) of the base members of the current invention mounted on a deformity having significant angulation.

DESCRIPTION OF THE PREFERRED EMBODIMENTS

Figure 4:
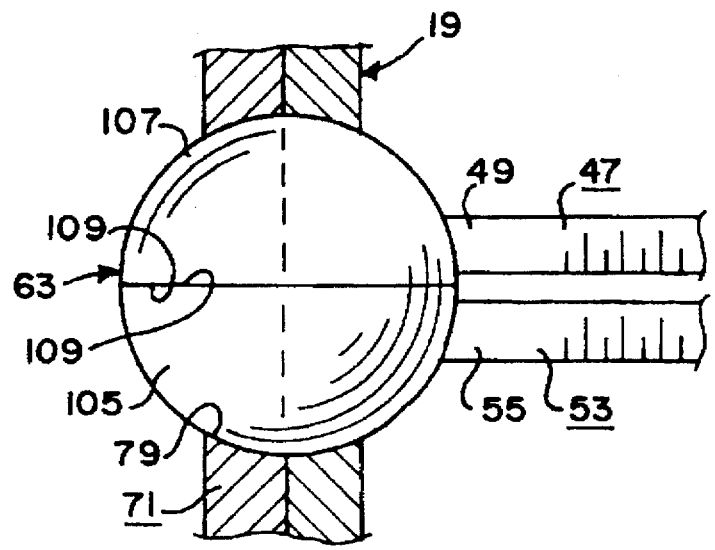
FIG. 4 is a sectional view substantially as taken on line 4—4 of FIG. 1 on an enlarged scale and with portions omitted and broken away for clarity.
Figure 5:
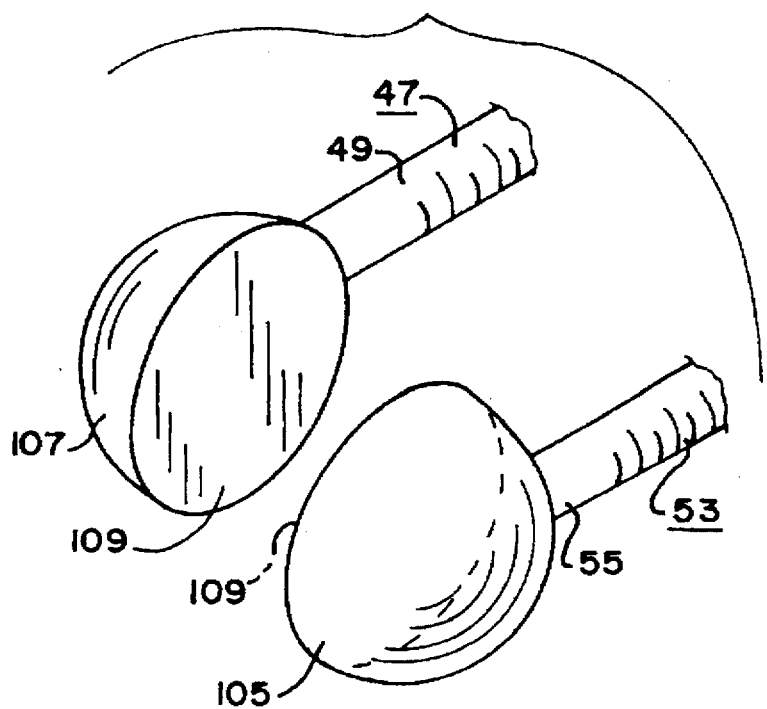
FIG. 5 is an exploded perspective view of parts of one of the connector means of the external fixator of FIG. 1.

A first preferred embodiment of the present invention is shown in FIGS. 1–9, and identified by the numeral 11. The external fixator 11 is part of a circumferential-type orthopedic external fixator 13 for securing a first bone element 15 relative to a second bone element 17.

The external fixator 11 includes a first base member 19 for attachment to the first bone element 15; a second base member 21 for attachment to the second bone element 17; an adjustable effective length first strut 23 having a first end 25 and a second end 27; an adjustable effective length second strut 29 having a first end 31 and a second end 33; an adjustable effective length third strut 35 having a first end 37 and a second end 39; an adjustable effective length fourth strut 41 having a first end 43 and a second end 45; an adjustable effective length fifth strut 47 having a first end 49 and a second end 51; an adjustable effective length sixth strut 53 having a first end 55 and a second end 57; first connector means 59 for rotatably attaching the first ends 25, 31 of the first and second struts 23, 29 relative to one another and relative to the first base member 19; second connector means 61 for rotatably attaching the first ends 37, 43 of the third and fourth struts 35, 41 relative to one another and relative to the first base member 19; third connector means 63 for rotatably attaching the first ends 49, 55 of the fifth and sixth struts 47, 53 relative to one another and relative to the first base member 19; fourth connector means 65 for rotatably attaching the second ends 27, 57 of the first and sixth struts 23, 53 relative to one another and relative to the second base member 21; fifth connector means 67 for rotatably attaching the second ends 33, 39 of the second and third struts 29, 35 relative to one another and relative to the second base member 21; and sixth connector means 69 for rotatably attaching the second ends 45, 51 of the fourth and fifth struts 41, 47 relative to one another and relative to the second base member 21. When used herein, the phrase "rotatably attaching" when describing the attachment between two or more parts or elements means that the referenced parts or elements are attached to one another in such a manner that allows rotation therebetween.

Figure 25:
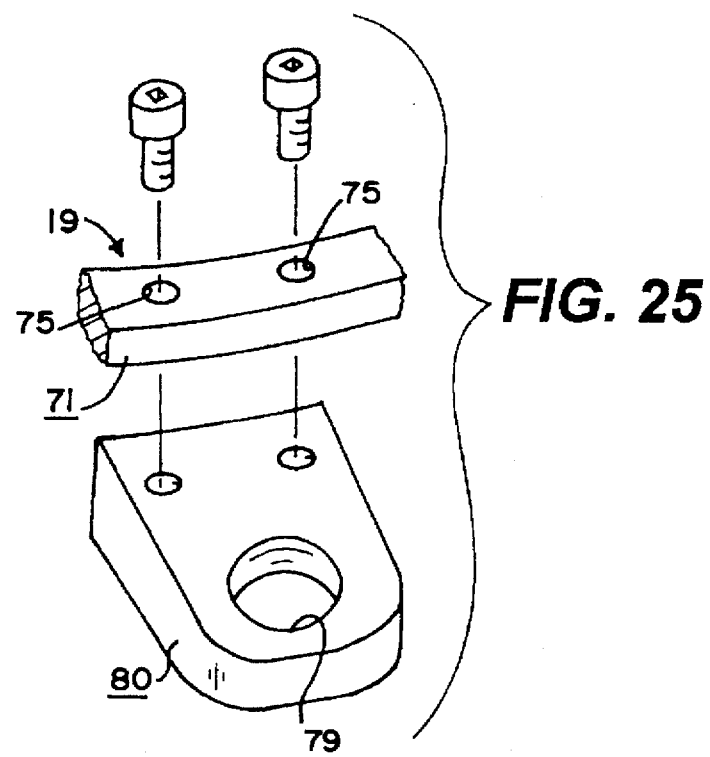
FIG. 25 is an exploded view of an alternate arrangement of a base member and associated structure for use with the embodiment of FIGS. 1–10.

The first and second base members 19, 21 may be constructed in various manners, out of various materials, and in various shapes and sizes. Thus, for example, each base member 19, 21 may consist of a one-piece or multi-piece Iiizarov-type halo or ring 71 for encircling a patient's limb, etc. and for being secured to one of the bone elements 15, 17 or the like by way of transfixation screws, wires or pins 73, etc., as will now be apparent to those skilled in the art. Each ring 71 preferably has a plurality of spaced apertures 75 therethrough for allowing the transfixation screws, wires or pins 73, etc., to be secured thereto with typical fixator clamps 77 or the like as will now be apparent to those skilled in the art. The spaced apertures 75 may also be used to join the various connector means 59, 61, 63, 65, 67, 69 to the respective ring 71. However, with respect to the preferred embodiment shown in FIGS. 1–7, each ring 71 preferably differs from a typical Ilizarov-type ring by having a plurality of partially spherical cavities 79 for reasons which will hereinafter become apparent. The partially spherical cavities 79 may be formed integrally with the rings 71 as shown clearly in FIGS. 2–4. On the other hand, each partially spherical cavity 79 may be formed in a plate member 80 that can be bolted or otherwise fixedly attached to one of the rings 71 as clearly shown in FIG. 25 and as will now be apparent to those skilled in the art. Additional, each partially spherical cavity 79 may be partially formed in the rings 71 and partially formed in separate plate members which coact with one another to define the partially spherical cavities 79, etc.

Each of the struts 23, 29, 35, 41, 47, 53 are preferably similar in construction to one another. The construction and operation of each strut 23, 29, 35, 41, 47, 53 may vary and may be designed to provide coarse and/or fine adjustment of the effective length thereof. When used herein, the phrase "effective length" when describing the length of one or more struts 23, 29, 35, 41, 47, 53 means the distance between the center of rotation of two associated connector means 59, 61, 63, 65, 67, 69. The embodiment of each strut 23, 29, 35, 41, 47, 53 shown generally in FIGS. 1–9 includes a first component 81, a second component 83, and coupling means 85 for adjustably coupling the first and second components 81, 83 to one another. Each first component 81 preferably includes an elongated rod 87 having a threaded end 89. Each second component 83 preferably includes an elongated rod 91 having a threaded end 93. Each coupling means 85 preferably has a first threaded portion 95 for coacting with the threaded end 89 of the rod 87 of the first components 81 and a second threaded portion 97 for coacting with the threaded end 93 of the rod 91 of the second component 83. The threaded end 89, threaded end 93, first threaded portion 95, and second threaded portion 97 are preferably designed so that rotation of the coupling means 85 about its longitudinal axis will cause the first and second components 81, 83 to move in opposite directions. Thus, for example, the threaded end 89 of the first component 81 and the first threaded portion 95 of the coupling means 85 may have coacting right-hand threads while the threaded end 93 of the second component 83 and the second threaded portion 97 of the coupling means 85 may have coacting left-hand threads, or vice versa, so that rotating the coupling means 85 about its longitudinal axis will cause the associated parts to act like or as a turnbuckle to either extend or retract the first and second components 81, 83 relative to one another and the coupling means 85 and thereby adjust or vary the overall length of each strut 23, 29, 35, 41, 47, 53 as will now be apparent to those skilled in the art. Also, while the threaded end 89 of the rod 87 and the threaded end 93 of the rod 91 are shown in the drawings as male threads and while the threaded portions 95, 97 of the coupling means 85 are shown in the drawings as female threads, an opposite construction can be used (i.e., having female threads on the threaded end 89 of the rod 87 and the threaded end 93 of the rod 91, and male threads on the threaded portions 95, 97 of the coupling means 85).

It should be understood that the effective length of each strut 23, 29, 35, 41, 47, 53 can be adjusted in various other manners and by various other means. For example, each strut 23, 29, 35, 41, 47, 53 could include a hydraulic or pneumatic piston, electric motor and gear trains, etc., and various controls for allowing the effective length of each strut 23, 29, 35, 41, 47, 53 to be easily and accurately controlled. Further, each strut 23, 29 rod with threaded ends and each connector means 59, 61, 63, 65, 67, 69 could have a threaded aperture for coacting therewith as more fully described hereinbelow with reference to the embodiment of FIG. 27.

Figure 8:
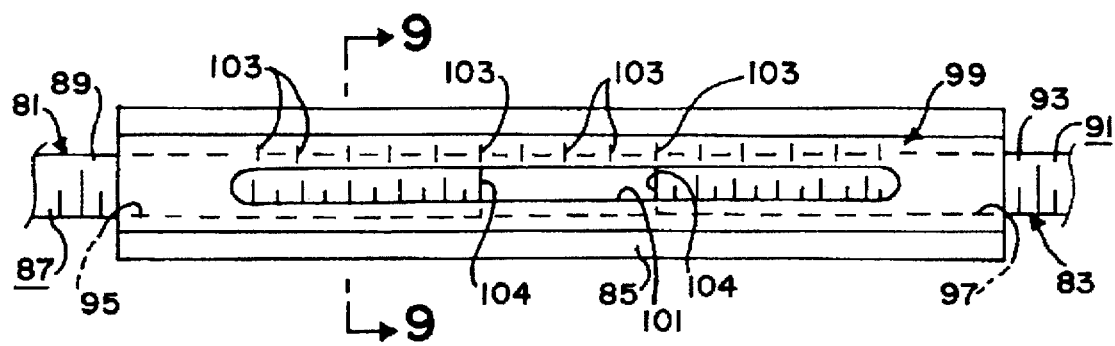
FIG. 8 is a front elevational view of portions of an adjustable effective length strut of the external fixator of FIG. 1.
Figure 9:
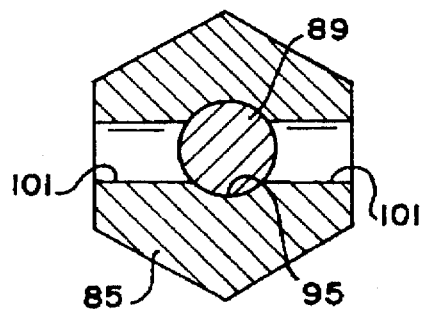
FIG. 9 is a sectional view substantially as taken on line 9—9 of FIG. 8.
Figure 10:
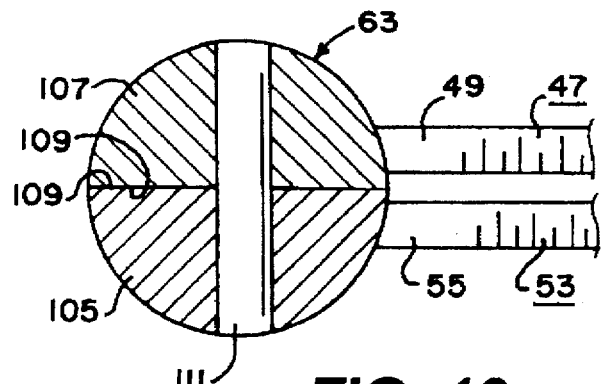
FIG. 10 is a sectional view of parts of a modified embodiment of a connector means of the present invention.

The device 11 may include indicia or gauge means 99 for providing an indication or relative measurement of the effective length of each strut 23, 29, 35, 41, 47, 53. For example, as shown in FIGS. 8 and 9, the coupling means 85 of each strut 23, 29, 35, 41, 47, 53 may have one or more elongated slots 101 which allows portions of the distal end of each component 81, 83 of each strut 23, 29, 35, 41, 47, 53 to be viewed therethrough, and a plurality of spaced apart indicia marks 103 or the like along the effective length of the slots 101 forming a graduated scale so that an accurate indication of the effective length of each strut 23, 29, 35, 41, 47, 53 can be easily and quickly determined by merely noting the position of a certain portion of each component 81, 83 relative to the indicia marks 103. Thus, for example, the indicia marks 103 may be graduated so that the alignment of the distal end 104 of each elongated rod 87, 91 with a certain indicia mark 103 as clearly shown in FIG. 8 will provide an indication or relative measurement of the overall length of each strut 23, 29, 35, 41, 47, 53 as will now be apparent to those skilled in the art.

In the embodiments shown in FIGS. 1–7 and 10, each of the connector means 59, 61, 63, 65, 67, 69 consists of a split-ball connector including a first partially spherical member 105 attached to one of the ends 25, 27, 31, 33, 37, 39, 43, 45, 49, 51, 55, 57 of one of the struts 23, 29, 35, 41, 47, 53, and a second partially spherical member 107 attached to one of the ends 25, 27, 31, 33, 37, 39, 43, 45, 49, 51, 55, 57 of another of the struts 23, 29, 35, 41, 47, 53. Each of the partially spherical members 105, 107 of the connector means 59, 61, 63, 65, 67, 69 preferably has a planar face portion 109. Each of the partially spherical cavities 79 in the ring 71 of each base member 19, 21 is preferably sized and designed for rotatably entrapping a respective pair of the partially spherical members 105, 107 of the connector means 59, 61, 63, 65, 67, 69 with the planar face portions 109 thereof held movably against one another (see, for example, FIG. 4). While not necessary, each connector means 59, 61, 63, 65, 67, 69 may include pivot means such as a pivot rod 111 extending through the center of each planar face portion 109 of a coacting pair of partially spherical members 105, 107 for pivotally joining that pair of partially spherical members 105, 107 together as clearly shown in FIG. 10.

The split-ball connectors of FIGS. 1–7 and 10 have certain advantages. They save space since only three split-ball joints are necessary per swash plate or base member 19, 21 versus six separate joints if spherical ball joints on the end of each strut 23, 29, 35, 41, 47, 53. Also, if spherical ball joints are used on the end of each strut 23, 29, 35, 41, 47, 53, when adjusting the effective length of any strut 23, 29, 35, 41, 47, 53 rising the turnbuckle structure shown in FIGS. 1–9, there would be a tendency for the threaded half shafts and ball to rotate, preventing predictable adjustment in strut length. However, the split-ball connectors of FIGS. 1–7 and 10, containing hemispheres attached to adjacent struts, would prevent either hemisphere from rotating independently about its strut axis, but would allow the combined split ball joint to rotate about three axes as a unit. Therefore, when adjusting the effective length of any individual strut 23, 29, 35, 41, 47, 53 by rotating the coupling means 85, rotation of the corresponding rod 87, 91 is blocked by the coaction of the split-ball connectors. It would be necessary to block rotation of the corresponding rod 87, 91 whenever a coupling means 85 is rotated if using spherical ball joints on the end of each strut 23, 29, 33, 41, 47, 53 as will now be apparent to those skilled in the art.

Figure 11:
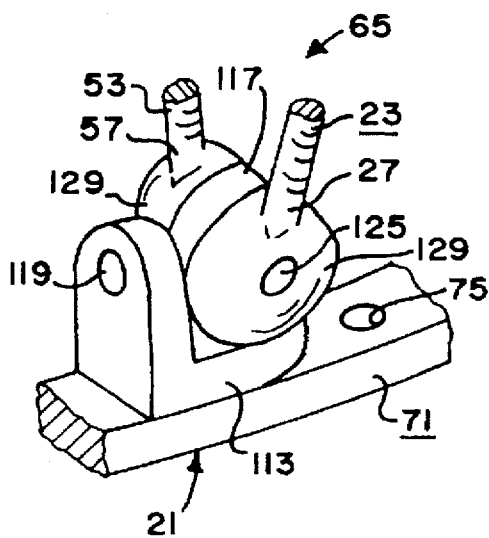
FIG. 11 is a perspective view of a modified embodiment of a connector means of the present invention.
Figure 12:
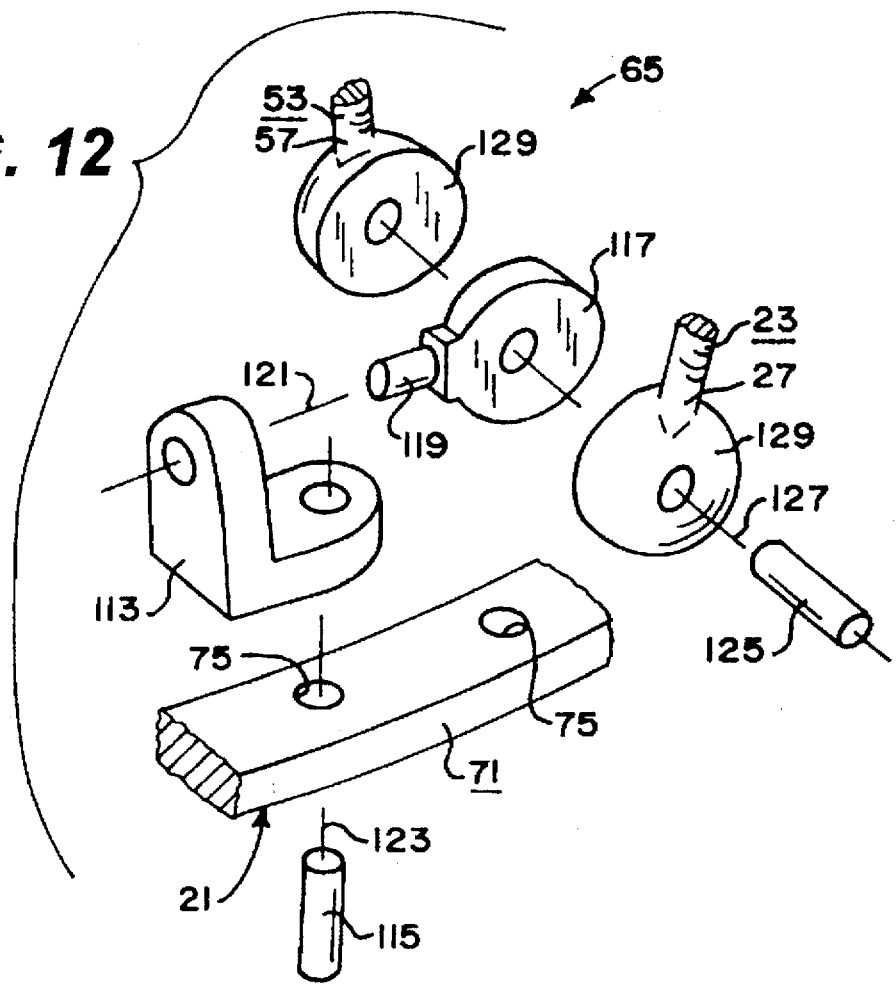
FIG. 12 is an exploded perspective view of FIG. 11.

In the embodiment shown in FIGS. 11 and 12, each of the connector means 59, 61, 63, 65, 67, 69 consists of a split U-joint connector or the like. While only the connector means 65 is shown in FIGS. 11 and 12, the other connector means 59, 61, 63, 67, 69 are preferably similar or identical in construction thereto. The split U-joint connector as shown in FIGS. 11 and 12 includes a first member 113, a shaft member 115 for attaching the first member 113 to a respective one of the first and second base members 19, 21, a second member 117, a pivot member 119 for pivotally attaching the second member 117 to the first member 113 with the longitudinal axis 121 of the pivot member 119 extending transverse to the longitudinal axis 123 of the shaft member 115, and a pivot member 125 for pivotally attaching one of the ends 25, 27, 31, 33, 37, 39, 43, 45, 49, 51, 55, 57 of one of the struts 23, 29, 35, 41, 47, 53 and one of the ends 25, 27, 31, 33, 37, 39, 43, 45, 49, 51, 55, 57 of another of the struts 23, 29, 35, 41, 47, 53 to the second member 117 (shown pivotally attaching the end 27 of the strut 23 and the end 57 of the strut 53 to the second member 117) with the longitudinal axis 127 of the pivot member 125 extending transverse to the longitudinal axis 121 of the pivot member 119. The ends 25, 27, 31, 33, 37, 39, 43, 45, 49, 51, 55, 57 of the struts 23, 29, 35, 41, 47, 53 may include enlarged heads 129 through which the pivot member 125 extend as indicated in FIGS. 11 and 12. The shalt member 115 may be bolted or press-fitted or otherwise securely attached to the first member 113 or may be formed as an integral, one-piece unit with the first member 113, or may be rotatably secured to the respective base member 19, 21 by a typical retainer clip or the like as will now be apparent to those skilled in the art for pivotally attaching the first member 113 to a respective one of the first and second base members 19, 21. The pivot member 119 may be press-fitted or otherwise securely attached to the second member 117 or may be formed as an integral, one-piece unit with the second member 117, and may be rotatably secured to the first member 113 by a typical retainer clip or the like as will now be apparent to those skilled in the art. The pivot member 125 may be press-fitted or otherwise securely attached to one of the coacting members (i.e., the second member 117 or one of the enlarged heads 129) or may be formed as an integral, one-piece unit with one of the coacting members (i.e., the second member 117 or one of the enlarged heads 129), or may be rotatably secured relative to each coacting member (i.e., to the second member 117 and both of the enlarged heads 129) by typical retainer clips or the like as will now be apparent to those skilled in the art.

Figure 13:
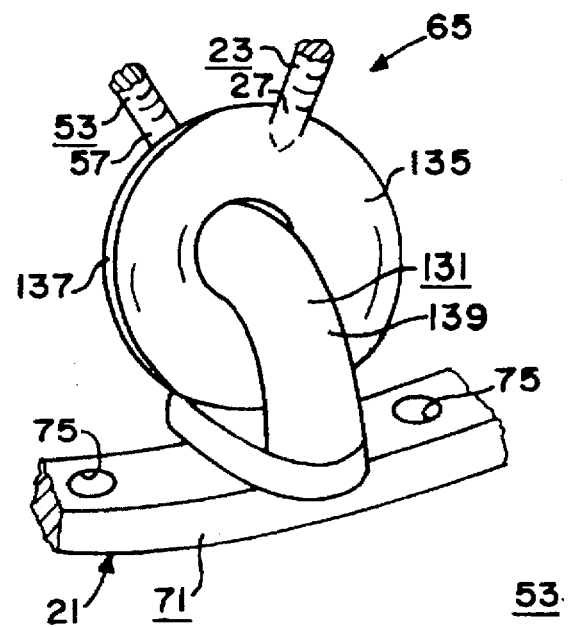
FIG. 13 is a perspective view of another modified embodiment of a connector means of the present invention.
Figure 14:
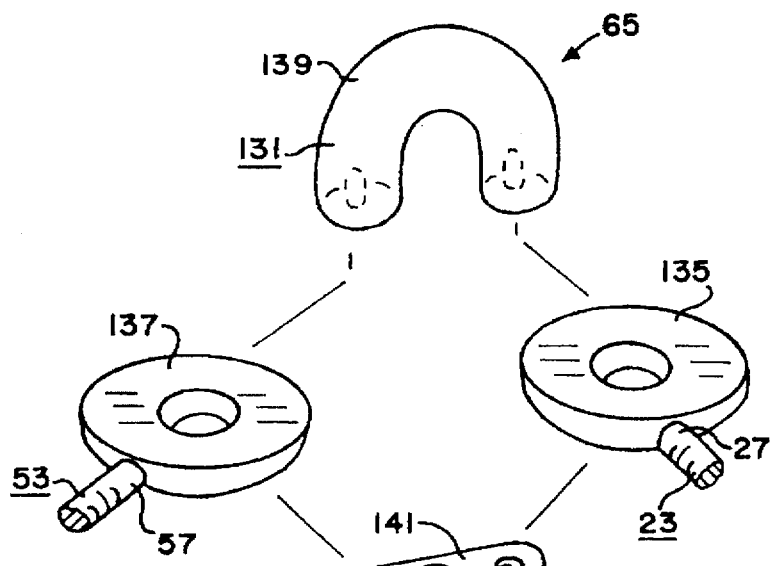
FIG. 14 is an exploded perspective view of FIG. 13.

In the embodiment shown in FIGS. 13 and 14, each of the connector means 59, 61, 63, 65, 67, 69 consists of a split chain link connector or the like. While only the connector means 65 is shown in FIGS. 13 and 14, the other connector means 59, 61, 63, 67, 69 are preferably similar or identical in construction thereto. The split chain link connector as shown in FIGS. 13 and 14 includes a first ring member 131, a shaft member 133 attaching the first ring member 131 to a respective one of the first and second base members 19, 21, a second ring member 135 attached to one of the ends 25, 27, 31, 33, 37, 39, 43, 45, 49, 51, 55, 57 of one of the struts 23, 29, 35, 41, 47, 53 (shown attached to the end 27 of the strut 23) and pivotally attached to the first ring member 131, and a third ring member 137 attached to one of the ends 25, 27, 31, 33, 37, 39, 43, 45, 49, 51, 55, 57 of another of the struts 23, 29, 35, 41, 47, 53 (shown attached to the end 57 of the strut 53) and pivotally attached to the first and second ring members 131, 135. Each first ring member 131 is preferably formed by a U-shaped member 139 for extending through the second and third ring members 135, 137, and a bridge member 141 for closing the U-shaped member 139 after the U-shaped member 139 is passed through the central hole in the second and third ring members 135, 137. The bridge member 141 may be removably attached to the U-shaped member 139 by screws 142 or the like (see FIG. 14). The shaft member 133 may be bolted, press-fitted or otherwise securely attached to the bridge member 141 or may be formed as an integral, one-piece unit with the bridge member 141, or may be rotatably secured to both the bridge member 141 and the respective base member 19, 21 by typical retainer clips or the like as will now be apparent to those skilled in the art to pivotally attach the first ring member 131 to a respective one of the first and second base members 19, 21. The method of attaching the second and third ring members 135, 137 to the respective ends 25, 27, 31, 33, 37, 39, 43, 45, 49, 51, 55, 57 of the struts 23, 29, 35, 41, 47, 53 may vary as will now be apparent to those skilled in the art. Thus, for example, each ring member 135, 137 may be integrally formed as a one-piece unit with a respective end 25, 27, 31, 33, 37, 39, 43, 45, 49, 51, 55, 57 of a respective strut 23, 29, 35, 41, 47, 53 as will now be apparent to those skilled in the art.

Figure 15:
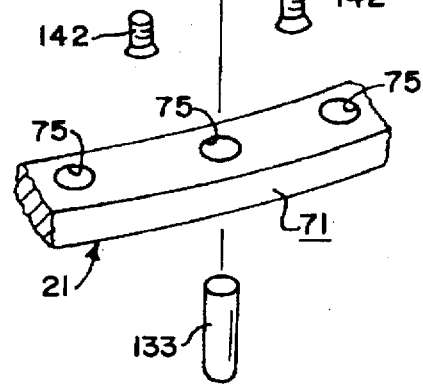
FIG. 15 is a perspective view of yet another modified embodiment of a connector means of the present invention.
Figure 15:
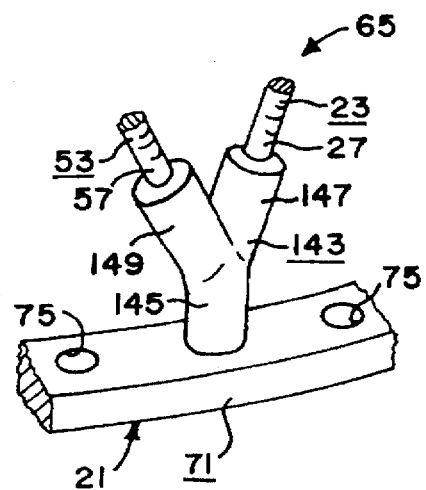
Figure 16:
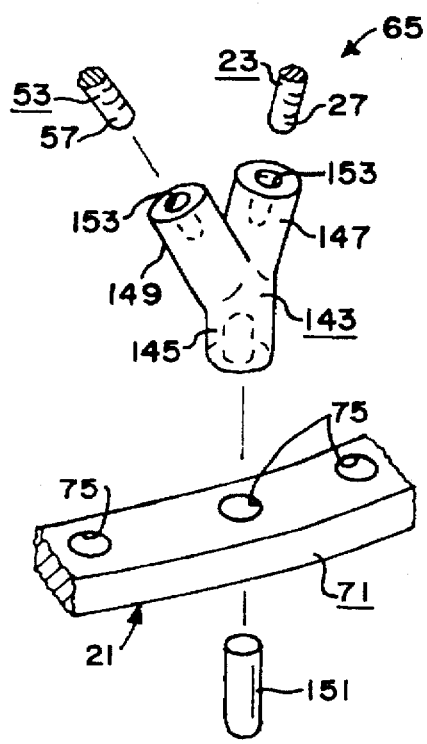
FIG. 16 is an exploded perspective view of FIG. 15.

In the embodiment shown in FIGS. 15 and 16, each of the connector means 59, 61, 63, 65, 67, 69 consists of a flexible or elastic connector. While only the connector means 65 is shown in FIGS. 15 and 16, the other connector means 59, 61, 63, 67, 69 are preferably similar or identical in construction thereto. The flexible or elastic connector as shown in FIGS. 15 and 16 includes a flexible or elastic Y-shaped body member 143 constructed out of a flexible or elastic rubber or the like with a trunk portion 145 for attachment to a respective one of the first and second base members 19, 21, a first arm 147 for attachment to one of the ends 25, 27, 31, 33, 37, 39, 43, 45, 49, 51, 55, 57 of one of the struts 23, 29, 35, 41, 47, 53 (shown attached to the end 27 of the strut 23), and a second arm 149 for attachment to one of the ends 25, 27, 31, 33, 37, 39, 43, 45, 49, 51, 55, 57 of another one of the struts 23, 29, 35, 41, 47, 53 (shown attached to the end 57 of the strut 53). While the trunk portion 145 may be fixedly attached to a respective one of the first and second base members 19, 21 due to the flexibility or elasticity thereof, a shaft member 151 may be provided for connecting the trunk portion 145 to a respective one of the first and second base members 19, 21. The shaft member 151 may be bolted or press-fitted or otherwise securely attached to the trunk portion 145 or may be formed as an integral, one-piece unit with the trunk portion 145, or may be rotatably secured to the respective base member 19, 21 by a typical retainer clip or the like as will now be apparent to those skilled in the art to pivotally connect the trunk portion 145 to a respective one of the first and second base members 19, 21. The method of attaching the first and second arms 147, 149 to the respective ends 25, 27, 31, 33, 37, 39, 43, 45, 49, 51, 55, 57 of the struts 23, 29, 35, 41, 47, 53 may vary as will now be apparent to those skilled in the art. Thus, for example, the respective ends 25, 27, 31, 33, 37, 39, 43, 45, 49, 51, 55, 57 of the struts 23, 29, 35, 41, 47, 53 may be externally threaded and each arm portion 147, 149 may have a threaded aperture 153 for threadably receiving the respective ends 25, 27, 31, 33, 37, 39, 43, 45, 49, 51, 55, 57 of the struts 23, 29, 35, 41, 47, 53. The threaded aperture 153 may be formed in a tubular metal insert in each arm portion 147, 149 as will now be apparent to those skilled in the art.

Figure 17:
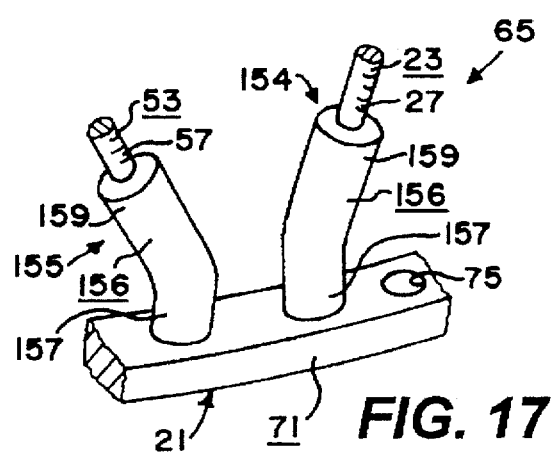
FIG. 17 is a perspective view of yet another modified embodiment of a connector means of the present invention.
Figure 18:
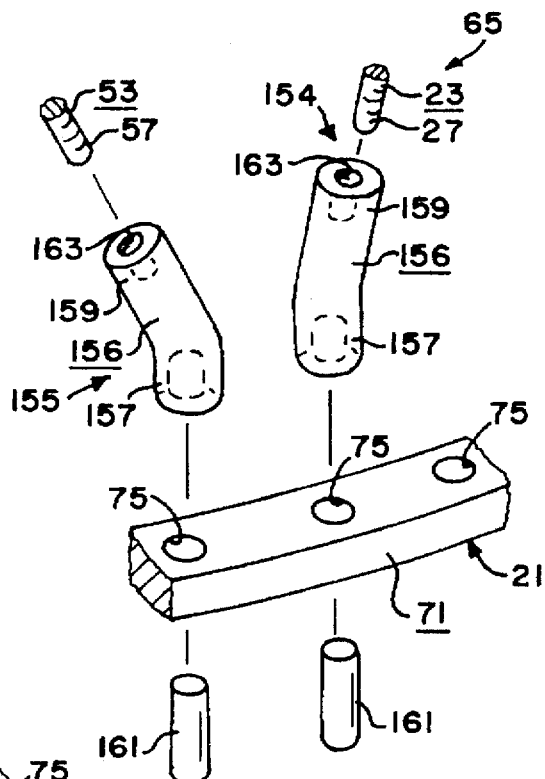
FIG. 18 is an exploded perspective view of FIG. 17.

In the embodiment shown in FIGS. 17 and 18, each of the connector means 59, 61, 63, 65, 67, 69 consists of a flexible or elastic connector. While only the connector means 65 is shown in FIGS. 17 and 18, the other connector means 59, 61, 63, 67, 69 are preferably similar or identical in construction thereto. The flexible or elastic connector as shown in FIGS.

17 and 18 includes a first body means 154 attached to a respective one of the first and second base members 19, 21 and to one of the ends 25, 27, 31, 33, 37, 39, 43, 45, 49, 51, 55, 57 of one of the struts 23, 29, 35, 41, 47, 53, and a second body means 155 attached to the respective one of the first and second base members 19, 21 adjacent and independently of the first body means 154 and to one of the ends 25, 27, 31, 33, 37, 39, 43, 45, 49, 51, 55, 57 of one of the struts 23, 29, 35, 41, 47, 53. Each body means 154, 155 preferably includes a flexible or elastic body member 156 constructed out of a flexible or elastic rubber or the like with a first end portion 157 for attachment to a respective one of the first and second base members 19, 21, and a second end portion 159 for attachment to one of the ends 25, 27, 31, 33, 37, 39, 43, 45, 49, 51, 55, 57 of one of the struts 23, 29, 35, 41, 47, 53 (FIGS. 17 and 18 show the first body means 154 attached to the end 27 of the strut 23 and the second body means 155 attached to the end 57 of the strut 53). While the first end portion 157 may be fixedly attached to a respective one of the first and second base members 19, 21 due to the flexibility or elasticity thereof, a shaft member 161 may be provided for connecting the first end portion 157 to a respective one of the first and second base members 19, 21. The shaft member 161 may be bolted or press-fitted or otherwise securely attached to the first end portion 157 or may be formed as an integral, one-piece unit with the first end portion 157, or may be rotatably secured to the respective base member 19, 21 by a typical retainer clip or the like as will now be apparent to those skilled in the art for pivotally connecting the first end portion 157 to a respective one of the first and second base members 19, 21. The method of attaching the respective ends 25, 27, 31, 33, 37, 39, 43, 45, 49, 51, 55, 57 of the struts 23, 29, 35, 41, 47, 53 to the second end portion 159 may vary as will now be apparent to those skilled in the art. Thus, for example, the respective ends 25, 27, 31, 33, 37, 39, 43, 45, 49, 51, 55, 57 of the struts 23, 29, 35, 41, 47, 53 may be externally threaded and each second end portion 159 may have a threaded aperture 163 for threadably receiving the respective ends 25, 27, 31, 33, 37, 39, 43, 45, 49, 51, 55, 57 of the struts 23, 29, 35, 41, 47, 53. The threaded aperture 163 may be formed in a tubular metal insert in each end portion 159 as will now be apparent to those skilled in the art.

Figure 19:
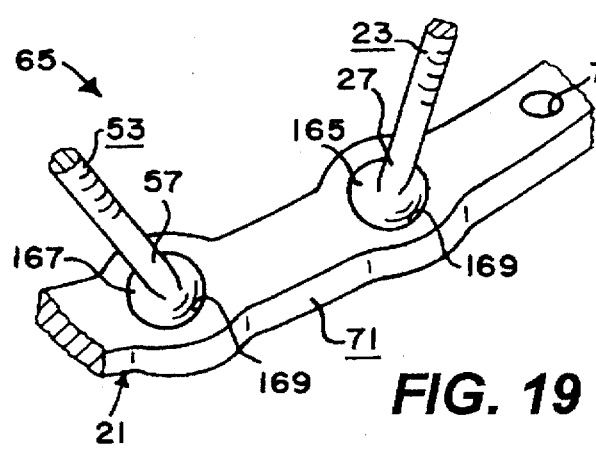
FIG. 19 is a perspective view of yet another modified embodiment of a connector means of the present invention.
Figure 20:
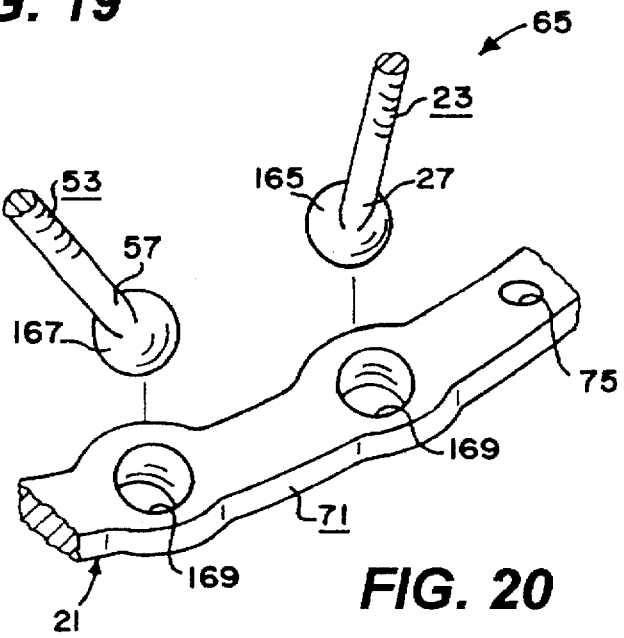
FIG. 20 is an exploded perspective view of FIG. 19.
Figure 26:
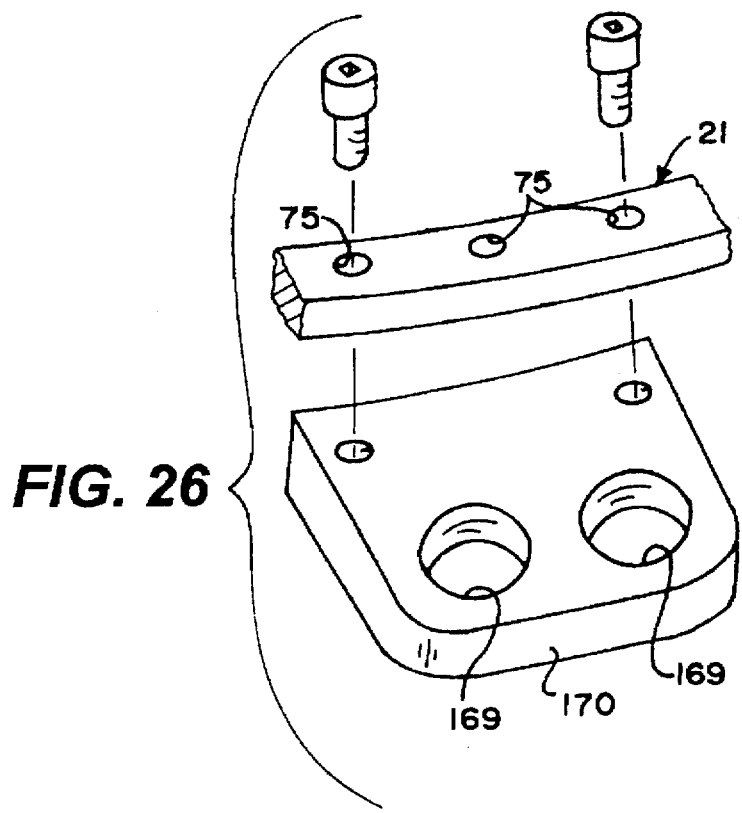
FIG. 26 is an exploded view of an alternate arrangement of a base member and associated structure for use with the embodiment of FIGS. 19 and 20.

In the embodiment shown in FIGS. 19 and 20, each of the connector means 59, 61, 63, 65, 67, 69 consists of a pair of spherical members. While only the connector means 65 is shown in FIGS. 19 and 20, the other connector means 59, 61, 63, 67, 69 are preferably similar or identical in construction thereto. The connector means as shown in FIGS. 19 and 20 includes a first spherical member 165 attached to one of the ends 25, 27, 31, 33, 37, 39, 43, 45, 49, 51, 55, 57 of one of the struts 23, 29, 35, 41, 47, 53, and a second spherical member 167 attached to another of the ends 25, 27, 31, 33, 37, 39, 43, 45, 49, 51, 55, 57 of one of the struts 23, 29, 35, 41, 47, 53. FIGS. 19 and 20 show the first spherical member 165 attached to the end 27 of the strut 23 and the second spherical member 167 attached to the end 57 of the strut 53. With respect to the embodiment shown in FIGS. 19 and 20, each ring 71 of each base member 19, 21 has a plurality of partially spherical cavities 169 sized and designed for rotatably entrapping one of the spherical members 165, 167. The partially spherical cavities 169 may be formed integrally with the rings 71 as shown clearly in FIGS. 19 and 20. On the other hand, each partially spherical cavity 169, or a coacting pair of partially spherical cavities 169, may be formed in a plate member 170 that can be bolted or otherwise fixedly attached to one of the rings 71 as clearly shown in FIG. 26 and as will now be apparent to those skilled in the art. Additional, each partially spherical cavity 169 may be partially formed in the rings 71 and partially formed in separate plate members which coact with one another to define the partially spherical cavities 169, etc.

Figure 21:
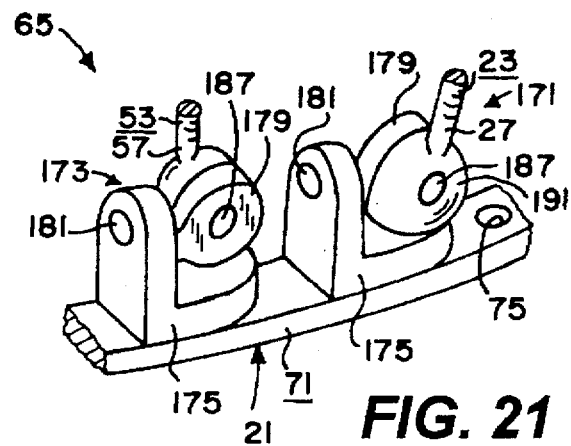
FIG. 21 is a perspective view of yet another modified embodiment of a connector means of the present invention.
Figure 22:
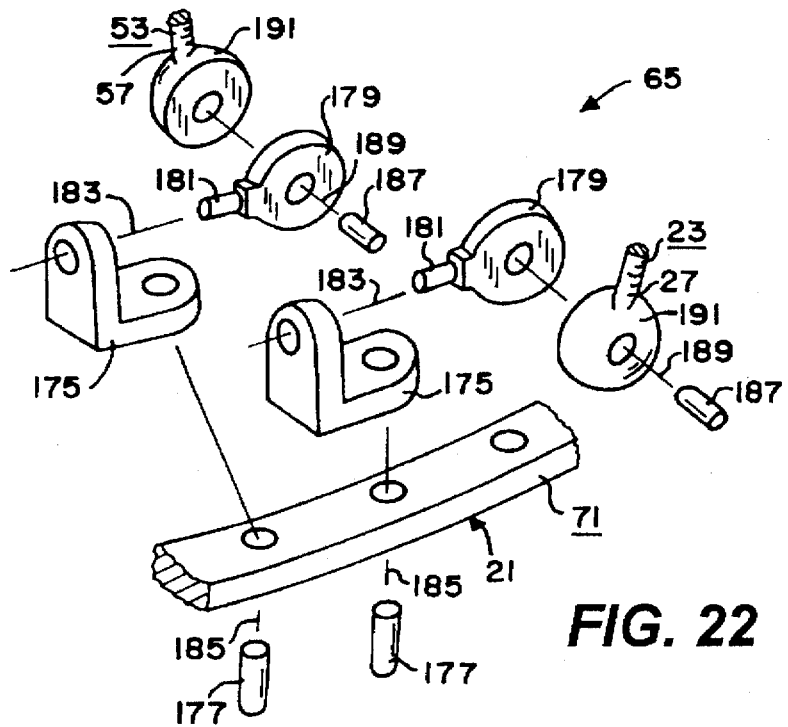
FIG. 22 is an exploded perspective view of FIG. 21.

In the embodiment shown in FIGS. 21 and 22, each of the connector means 59, 61, 63, 65, 67, 69 consists of a pair of U-joint type connectors. While only the connector means 65 is shown in FIGS. 21 and 22, the other connector means 59, 61, 63, 67, 69 are preferably similar or identical in construction thereto. The U-joint type connectors as shown in FIGS. 21 and 22 includes a first U-joint connector 171 attached to a respective one of the first and second base members 19, 21 and to one of the ends 25, 27, 31, 33, 37, 39, 43, 45, 49, 51, 55, 57 of one of the struts 23, 29, 35, 41, 47, 53, and a second U-joint connector 173 attached to the respective one of the first and second base members 19, 21 adjacent and independently of the first second U-joint connector 171 and to one of the ends 25, 27, 31, 33, 37, 39, 43, 45, 49, 51, 55, 57 of another of the struts 23, 29, 35, 41, 47, 53. Each U-joint connector 171, 173 preferably includes a first member 175, a shaft member 177 for attaching the first member i 75 to a respective one of the base members 19, 21, a second member 179, a pivot member 181 for pivotally attaching the second member 179 to the first member 175 with the longitudinal axis 183 of the pivot member 181 extending transverse to the longitudinal axis 185 of the shaft member 177, and a pivot member 187 for pivotally attaching one of the ends 25, 27, 31, 33, 37, 39, 43, 45, 49, 51, 55, 57 of one of the struts 23, 29, 35, 41, 47, 53 to the second member 179 with the longitudinal axis 189 of the pivot member 187 extending transverse to the longitudinal axis 183 of the pivot member 181. The ends 25, 27, 31, 33, 37, 39, 43, 45, 49, 51, 55, 57 of the struts 23, 29, 35, 41, 47, 53 may include enlarged heads 191 through which the pivot member 187 extend as indicated in FIGS. 21 and 22. The shaft member 177 may be bolted or press-fitted or otherwise securely attached to the first member 175 or may be formed as an integral, one-piece unit with the first member 175, or may be rotatably secured to the respective base member 19, 21 by a typical retainer clip or the like as will now be apparent to those skilled in the art for pivotally attaching the first member 175 to a respective one of the base members 19, 21. The pivot member 181 may be press-fitted or otherwise securely attached to the second member 179 or may be formed as an integral, one-piece unit with the second member 179, and may be rotatably secured to the first member 175 by a typical retainer clip or the like as will now be apparent to those skilled in the art. The pivot member 187 may be press-fitted or otherwise securely attached to one of the coacting members (i.e., the second member 179 or the respective enlarged head 191) or may be formed as an integral, one-piece unit with one of the coacting members (i.e., the second member 179 or the respective enlarged head 191), or may be rotatably secured relative to each coacting member (i.e., to the second member 179 and the respective enlarged head 191) by typical retainer clips or the like as will now be apparent to those skilled in the art.

Figure 23:
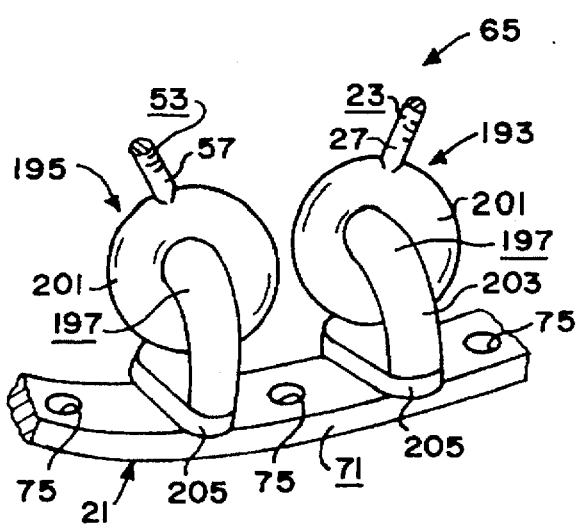
FIG. 23 is a perspective view of yet another modified embodiment of a connector means of the present invention.
Figure 24:
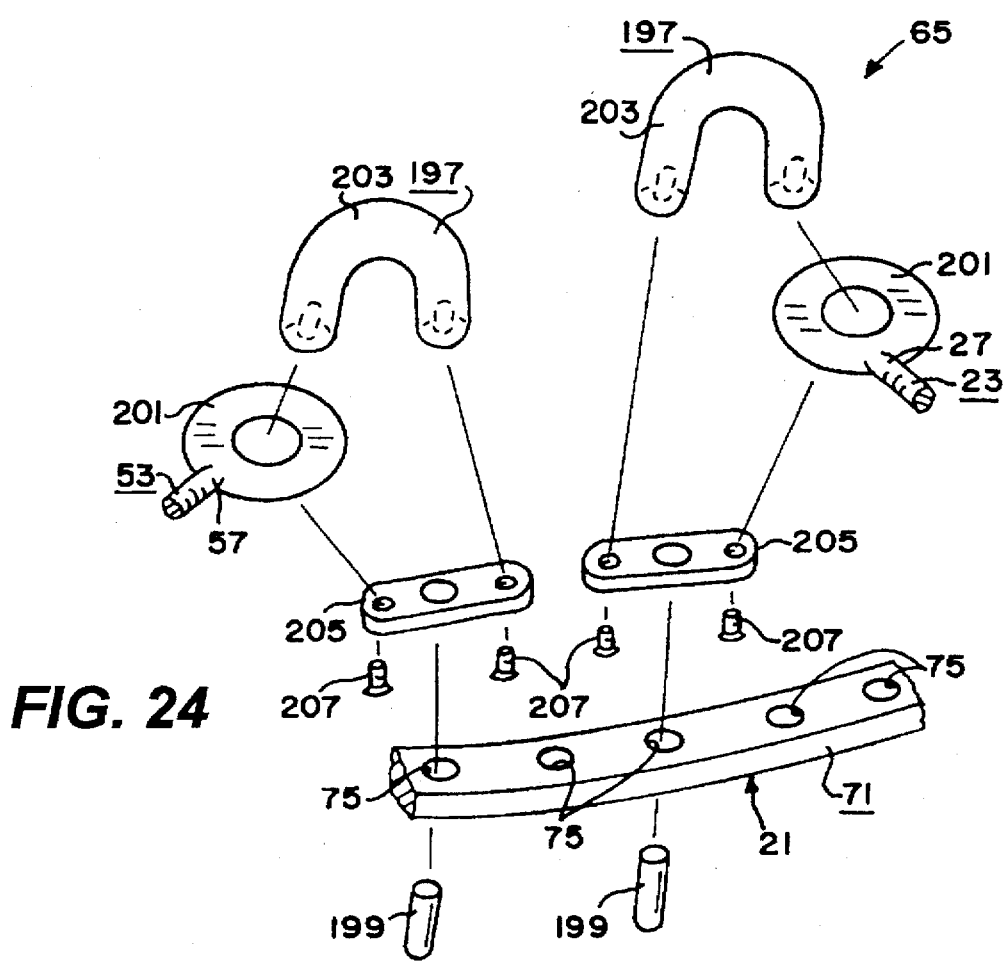
FIG. 24 is an exploded perspective view of FIG. 23.

In the embodiment shown in FIGS. 23 and 24, each of the connector means 59, 61, 63, 65, 67, 69 consists of a pair of chain link connectors. While only the connector means 65 is shown in FIGS. 23 and 24, the other connector means 59, 61, 63, 67, 69 are preferably similar or identical in construction thereto. The chain link connectors as shown in FIGS. 23 and 24 includes a first chain link connector 193 attached to a respective one of the first and second base members 19, 21 and to one of the ends 25, 27, 31, 33.37, 39, 43, 45, 49, 51, 55, 57 of one of the struts 23, 29, 35, 41, 47, 53, and a second chain link connector 195 attached to the respective one of the first and second base members 19, 21 adjacent and independently of the first chain link connector 193 and to one of the ends 25, 27, 31, 33, 37, 39, 43, 45, 49, 51, 55, 57 of another of the struts 23, 29, 35, 41, 47, 53. Each chain link connector 193, 195 preferably includes a first ring member 197, a pivot member 199 pivotally attaching the first ring member 197 to a respective one of the first and second base members 19, 21, a second ring member 201 attached to one of the ends 25, 27, 31, 3,3, 37, 39, 43, 45, 49, 51, 55, 57 of one of the struts 23, 29, 35, 41, 47, 53 (the second ring member 201 of the first chain link connector 193 is shown in FIGS. 23 and 24 attached to the end 27 of the strut 23; the second ring member 201 of the second chain link connector 195 is shown in FIGS. 23 and 24 attached to the end 57 of the strut 53) and pivotally attached to the first ring member 197. Each first ring member 197 is preferably formed by a U-shaped member 203 for extending through the second ring member 201, and a bridge member 205 for closing the U-shaped member 203 after the U-shaped member 203 is passed through the central hole in the second member 201. The bridge member 205 may be removably attached to the U-shaped member 203 by screws 207 or the like (see FIG. 24). The pivot member 199 may be press-fitted or otherwise securely attached to the bridge member 205 or may be formed as an integral, one-piece unit with the bridge member 205, or may be rotatably secured to both the bridge member 205 and the respective base member 19, 21 by typical retainer clips or the like as will now be apparent to those skilled in the art. The method of attaching the second ring member 201 to the respective ends 25, 27, 31, 33, 37, 39, 43, 45, 49, 51, 55, 57 of the struts 23, 29, 35, 41, 47, 53 may vary as will now be apparent to those skilled in the art. Thus, for example, each ring member 201 may be integrally formed as a one-piece unit with a respective end 25, 27, 31, 33, 37, 39, 43, 45, 49, 51, 55, 57 of a respective strut 23, 29, 35, 41, 47, 53 as will now be apparent to those skilled in the art.

Figure 27:
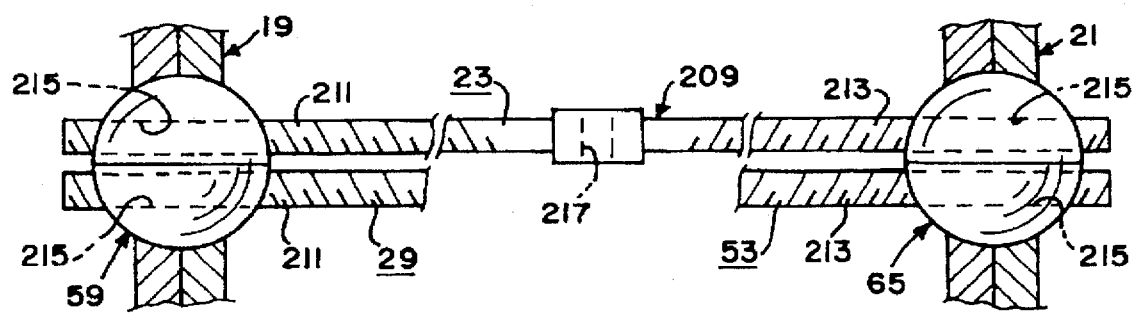
FIG. 27 is a sectional view similar to FIG. 4 but showing modified embodiments of the adjustable effective length struts and connector means of the external fixator of the present invention.

In the embodiment shown in FIG. 27, each adjustable effective length strut 23, 29, 35, 41, 47, 53 may consist of a one-piece, integral rod 209 having one end 211 with left hand external threads thereon, having another end 213 with fight hand external threads thereon, and each connector means 59, 61, 63, 65, 67, 69 may have an appropriately handed threaded aperture 215 for screwably receiving one of the ends 211, 213 of one of the rods 209. While only the connector means 59, 65 are shown in FIG. 27, the other connector means 61, 63, 67, 69 may be similar or identical in construction thereto. Likewise, while only portions of the struts 23, 29, 53 are shown in FIG. 27, the other struts 35, 41, 47 may be similar or identical in construction thereto. Each rod 209 may include grip means between the opposite ends to aid in the rotation thereof about its longitudinal axis. The grip means may consist simply of a transverse aperture 217 through the rod 209 to allow a bar or the like (not shown) to be inserted therethrough to provide a handle to allow the rod 209 to be easily rotated about its longitudinal axis as will now be apparent to those skilled in the art. The midportion of each rod 209 may be enlarged, etc., adjacent the transverse aperture 217 for reinforcement, etc. When a rod 209 is rotated, the associated connector means 59, 61, 63, 63, 67, 69 on the opposite ends thereof will move toward or away from one another, causing the effective length of the rod 209 to be varied and causing a corresponding or related movement of the base members 19, 21 as will now be apparent to those skilled in the art. It should also be noted that while FIG. 27 shows the split-ball connectors of FIGS. 1–7 and 10, it is not limited thereto and may be used with the type connectors shown in FIGS. 11–24, etc.

Figure 28:
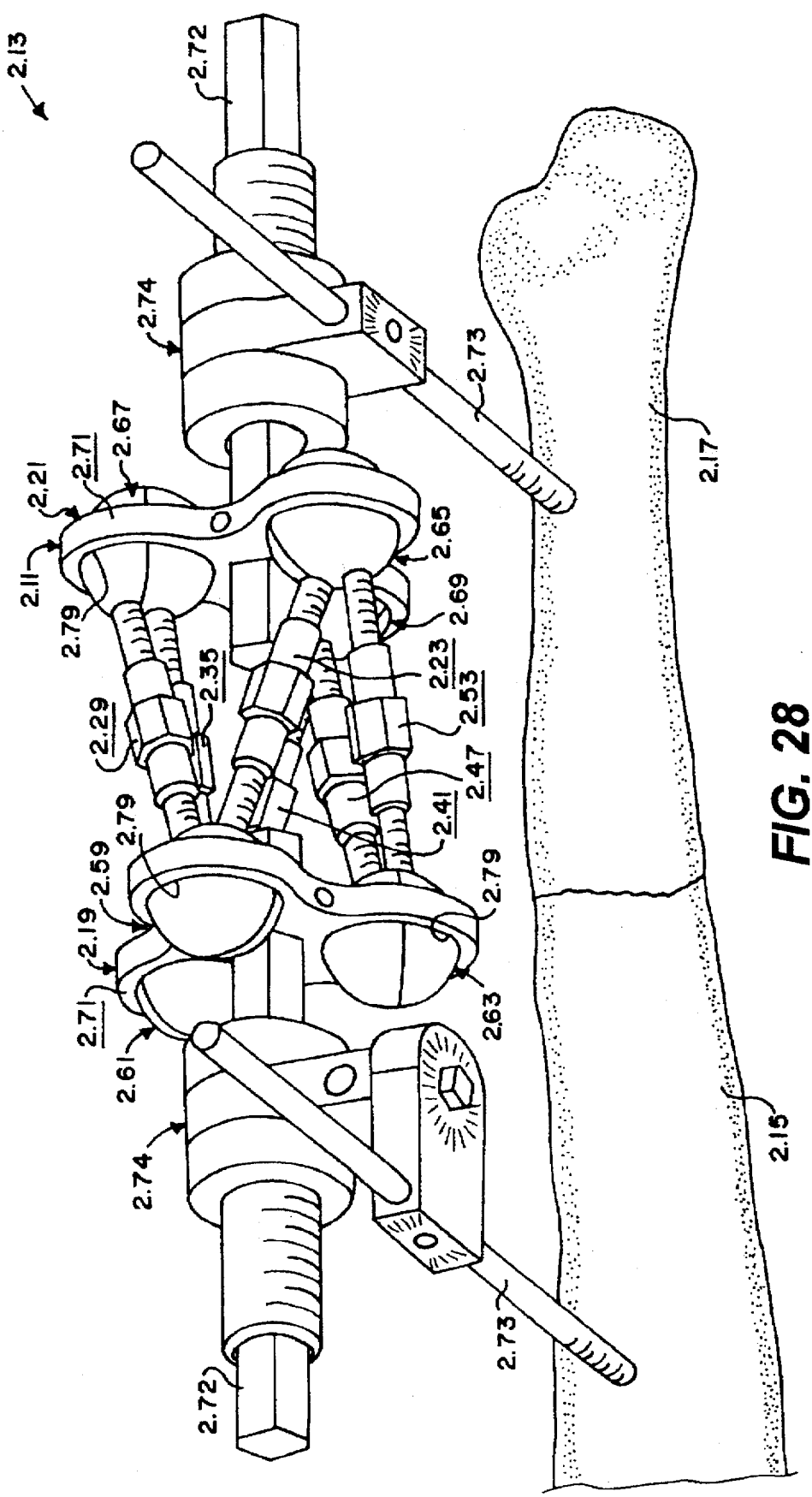
FIG. 28 is a perspective view of a second preferred embodiment of the present invention shown in combination with other elements of an orthopedic external fixator and a fractured tibia.

A second preferred embodiment of the present invention is shown in FIG. 28, and identified by the numeral 2.11. The external fixator 2.11 is a concentric part of a unilateral-type orthopedic external fixator 2.13 for securing a first bone element 2.15 relative to a second bone element 2.17.

The external fixator 2.11 includes a first base member 2.19 for attachment to the first bone element 2.15; a second base member 2.21 for attachment to the second bone element 2.17; an adjustable effective length first strut 2.23 having a first end and a second end; an adjustable effective length second strut 2.29 having a first end and a second end; an adjustable effective length third strut 2.35 having a first end and a second end; an adjustable effective length fourth strut 2.41 having a first end and a second end; an adjustable effective length fifth strut 2.47 having a first end and a second end; an adjustable effective length sixth strut 2.53 having a first end and a second end; first connector means 2.59 for rotatably attaching the first ends of the first and second struts 2.23, 2.29 to one another and relative to the first base member 2.19; second connector means 2.61 for rotatably attaching the first ends of the third and fourth struts 2.35, 2.41 to one another and relative to the first base member 2.19; third connector means 2.63 for rotatably attaching the first ends of the fifth and sixth struts 2.47, 2.53 to one another and relative to the first base member 2.19; fourth connector means 2.65 for rotatably attaching the second ends of the first and sixth struts 2.23, 2.53 to one another and relative to the second base member 2.21; fifth connector means 2.67 for rotatably attaching the second ends of the second and third struts 2.29, 2.35 to one another and relative to the second base member 2.21; and sixth connector means 2.69 for rotatably attaching the second ends of the fourth and fifth struts 2.41, 2.47 to one another and relative to the second base member 2.21.

The first and second base members 2.19, 2.21 may be constructed in various manners, out of various materials, and in various shapes and sizes. Thus, for example, each base member 2.19, 2.21 may consist of a one-piece or multi-piece plate 2.71 for being concentrically secured to a rigid elongated rod 2.72 or the like by way of typical set screws or the like. Standard transfixation screws, wires or pins 2.73, etc., are coupled relative to the base members 2.19, 2.21 and rods 2.72 by various connectors 2.74 which may be mounted on or an integral pan of the plates 2.71, or may be mounted directly on the rods 2.72 as shown in FIG. 28 and as will now be apparent to those skilled in the art.

The struts 2.23, 2.29, 2.35, 2.41, 2.47, 2.53 and connector means 2.59, 2.61, 2.63, 2.65, 2.67, 2.69 are preferably identical to the various struts 23, 29, 35, 41, 47, 53 and connectors means 59, 61, 63, 65, 67, 69 discloses hereinabove relative to the device 11 and reference should be made to the detailed disclosure hereinabove of the various struts 23, 29, 35, 41, 47, 53 and connectors means 59, 61, 63, 65, 67, 69 for a complete understanding of the various possible constructions of the struts 2.23, 2.29, 2.35, 2.41, 2.47, 2.53 and connector means 2.59, 2.61, 2.63, 2.65, 2.67, 2.69 of the device 2.11. Each plate 2.71 is constructed for use with the connector means 2.59, 2.61, 2.63, 2.65, 2.67, 2.69 used. Thus, for example, with respect to the embodiment shown in FIG. 28, each plate 2.71 preferably has a plurality of partially spherical cavities 2.79 therein for rotatably entrapping a respective pair of the partially spherical members of the split-ball connector means shown.

Figure 29:
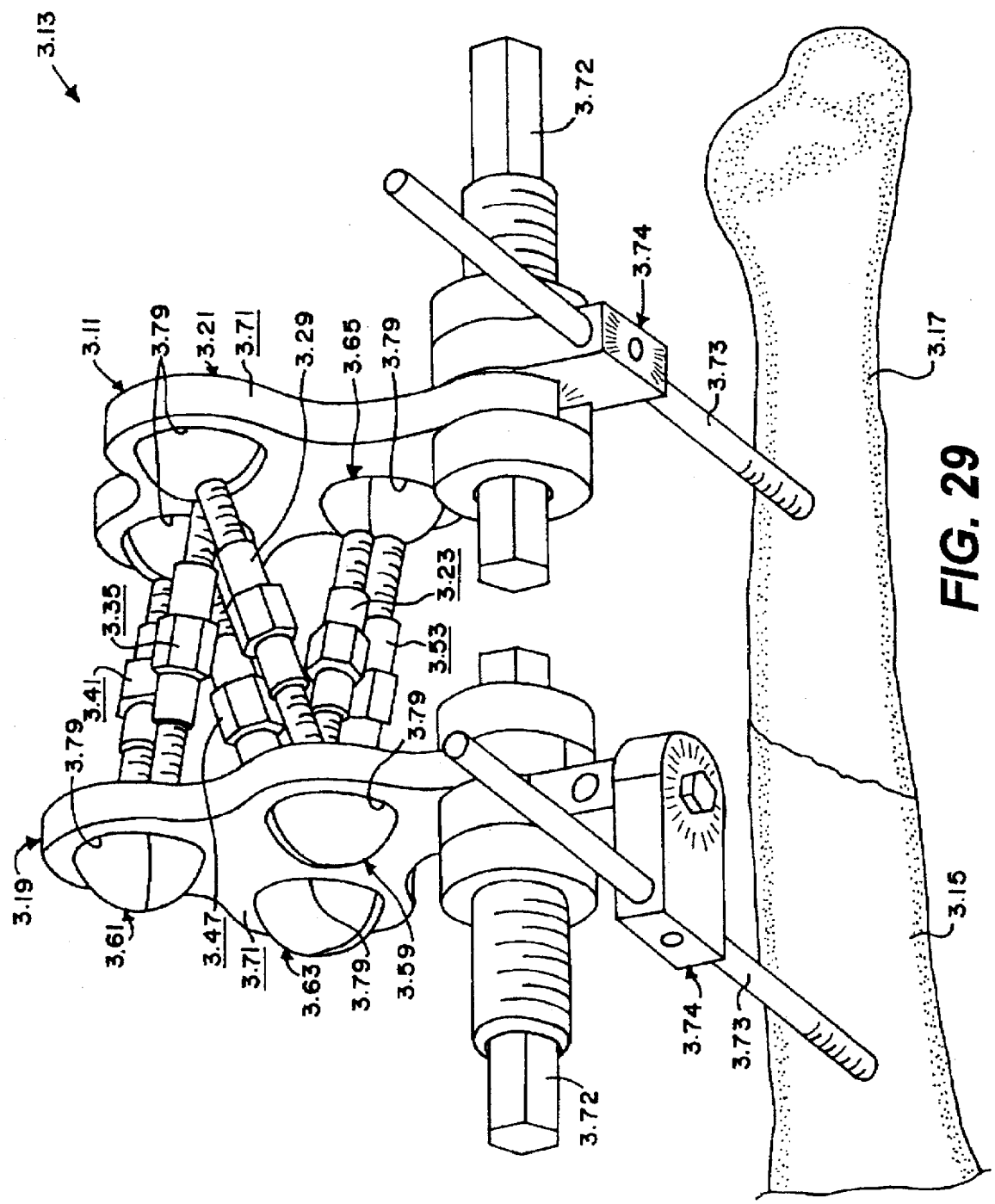
FIG. 29 is a perspective view of a third preferred embodiment of the present invention shown in combination with other elements of an orthopedic external fixator and a fractured tibia.

A third preferred embodiment of the present invention is shown in FIG. 29, and identified by the numeral 3.11. The external fixator 3.11 is part of a eccentrically mounted, unilateral-type orthopedic external fixator 3.13 for securing a first bone element 3.15 relative to a second bone element 3.17.

The external fixator 3.11 includes a first base member 3.19 for attachment to the first bone element 3.15; a second base member 3.21 for attachment to the second bone element 3.17; an adjustable effective length first strut 3.23 having a first end and a second end; an adjustable effective length second strut 3.29 having a first end and a second end; an adjustable effective length third strut 3.35 having a first end and a second end; an adjustable effective length fourth strut 3.41 having a first end and a second end; an adjustable effective length fifth strut 3.47 having a first end and a second end; an adjustable effective length sixth strut 3.53 having a first end and a second end; first connector means 3.59 for rotatably attaching the first ends of the first and second struts 3.23, 3.29 to one another and relative to the first base member 3.19; second connector means 3.61 for rotatably attaching the first ends of the third and fourth struts 3.35, 3.41 to one another and relative to the first base member 3.19; third connector means 3.63 for rotatably attaching the first ends of the fifth and sixth struts 3.47, 3.53 to one another and relative to the first base member 3.19; fourth connector means 3.65 for rotatably attaching the second ends of the first and sixth struts 3.23, 3.53 to one another and relative to the second base member 3.21; fifth connector means 3.67 for rotatably attaching the second ends of the second and third struts 3.29, 3.35 to one another and relative to the second base member 3.21; and sixth connector means 3.69 for rotatably attaching the second ends of the fourth and fifth struts 3.41, 3.47 to one another and relative to the second base member 3.21.

The first and second base members 3.19, 3.21 may be constructed in various manners, out of various materials, and in various shapes and sizes. Thus, for example, each base member 3.19, 3.21 may consist of a one-piece or multi-piece plate 3.71 for being eccentrically secured to a rigid elongated rod 3.72 or the like by way of typical set screws or the like. Standard transfixation screws, wires or pins 3.73, etc., are coupled relative to the base members 3.19, 3.21 and rods 3.72 by various connectors 3.74 which may be mounted on or an integral part of the plates 3.71, or may be mounted directly on the rods 3.72 as shown in FIG. 29 and as will now be apparent to those skilled in the art.

The struts 3.23, 3.29, 3.35, 3.41, 3,47, 3.53 and connector means 3.59, 3.61, 3.63, 3.65, 3.67, 3.69 are preferably identical to the various struts 23, 29, 35, 41, 47, 53 and connectors means 59, 61, 63, 65, 67, 69 discloses hereinabove relative to the device 11 and reference should be made to the detailed disclosure hereinabove of the various struts 23, 29, 35, 41, 47, 53 and connectors means 59, 61, 63, 65, 67, 69 for a complete understanding of the various possible constructions of the struts 3.23, 3.29, 3.35, 3.41, 3.47, 3.53 and connector means 3.59, 3.61, 3.63, 3.65, 3.67, 3.69 of the device 3.11. Each plate 3.71 is constructed for use with the connector means 3.59, 3.61, 3.63, 3.65, 3.67, 3.69 used. Thus, for example, with respect to the embodiment shown in FIG. 29, each plate 3.71 preferably has a plurality of partially spherical cavities 3.79 therein for rotatably entrapping a respective pair of the partially spherical members of the split-ball connector means shown.

As thus constructed, the present invention provides a novel external fixator and repositioning mechanism. The fixator preferably includes two base members or swash plates coupled together by six struts which are adjustable in length. The fixator of the current invention can, however, include more or less than six struts. Preferably, the device includes from two to eight struts that are adjustable in length. These struts in their resting positions are inclined with respect to one another. In the preferred embodiments, these struts are regularly spaced and similar in manufacture to aid in construction and clinical use, although irregular arrays of dissimilarly constructed struts could effect a gradual six axis correction. Each strut of one preferred embodiment is essentially a turnbuckle attached to a half sphere at either end. One half sphere is mated to a half sphere of an adjacent strut in a partially encapsulating socket, there being three such sockets on each of the swash plates. The sockets of one swash plate may be staggered with respect to the sockets of the other swash plate when viewed axially. The partial sockets which constrain the split balls may be an integral part of the swash plates or may be attached additionally.

The present invention functions as a fixator and a mechanism without the sockets actually clamping the balls against rotation. Ideally there is sufficient clearance to allow rotation of the balls about three axes and each half spheres about an axis perpendicular to the face of each half sphere, passing through the centers of the hemispheres without allowing excessive play along the three translational axes. Additional clamping of the balls could be done to prevent motion, but the present device is able to function as a repositioning mechanism by virtue of the changing length of the struts and therefore a concomitant rotation of half spheres about each other and/or the ball joint pair within their sockets.

The present device can function as a stabilizing fixator even though the balls are not tightly clamped but free to rotate. External fixation pin clamps may either be an integral part of the swash plates or may be attached. These clamps are then attached to pins or wires which are attached to bone fragments. Bone fragment positions may be changed by adjusting the effective lengths of the six struts accordingly. Each new six coordinate position of one fragment relative to the other can be achieved by changing the effective lengths of the six struts. Each combination of strut lengths determines a unique six coordinate position of one fragment relative to the other. No change in position between fragments can occur unless there is a change in the effective length of one or more struts. There is no over constraint, in that any change of any strut length causes a change in position of one fragment with respect to the other. The exact change in length for each strut to move one fragment relative to the other a prescribed amount can be accomplished by coordinate transformation by hand calculation, calculator, or computer.

Alternatively, similar accessory swash plates with only the centers of the split balls represented can be utilized to determine initial lengths of the struts. Orthogonal x-rays of a deformed limb are taken, and these, plus careful physical examination, are used to characterize or measure a deformity. In its deformed position, one fragment can be thought of as moved from its original or preferred position by displacement along and/or about the six axes which can be corrected by the present external fixator. Assuming a neutral or home position of the present invention, the accessory swash plates are held in a similar home position. One accessory swash plate is then displaced from the other accessory swash plate along and/or about the six axes in an amount equal to the deformities as measured on x-ray and physical exam. While the accessory swash plates are held in this deformed spatial relationship the distance between marks corresponding to the centers of the split ball joints are measured. The corresponding strut is then adjusted to match.

This is repeated for the remaining five strut lengths. At the end of this process the present invention is deformed exactly as the limb. The present invention is then securely attached to the bone fragments with skeletal pins or wires. The struts are then gradually or suddenly adjusted to their original or home length. The boney deformity is corrected as the present invention is corrected since the present invention is attached to the bone.

METHODS OF USING THE DEVICE OF THE CURRENT INVENTION

The unique methods of using the current invention shall be described for a preferred embodiment of the novel fixator that is illustrated in FIG. 1. As described above, this embodiment of the device includes two circular base members 71, and six adjustable length struts 301 (individually designated 23, 29, 35, 41, 47, and 53) interconnecting the two base members 71. The struts 301 are attached to the base members 71 by six split-ball connectors 303. In addition, most of the detailed description of the method provided herein specifically relates to hard tissue deformities, and particularly tibial deformities. Although the following methods are described in terms of this preferred embodiment of the present invention and tibial deformities, those of ordinary skill in the art can readily apply theses methods to other embodiments of the present invention and other tissue deformities.

1. Summary of Methods

In accordance with the unique method of using the device of the current invention, projective geometry, trigonometry, and matrix algebra are used to provide a general deformity equation that mathematically characterizes the deformity. With the general deformity equation, the lengths of each of the adjustable struts can be determined that will configure the device to mimic or mirror the deformity. The general deformity equation is based on a number of parameters, including the position of the bone relative to the device (i.e., device parameters and eccentricities), and the relative positions of the bone fragments (i.e., deformity parameters).

Figure 30:
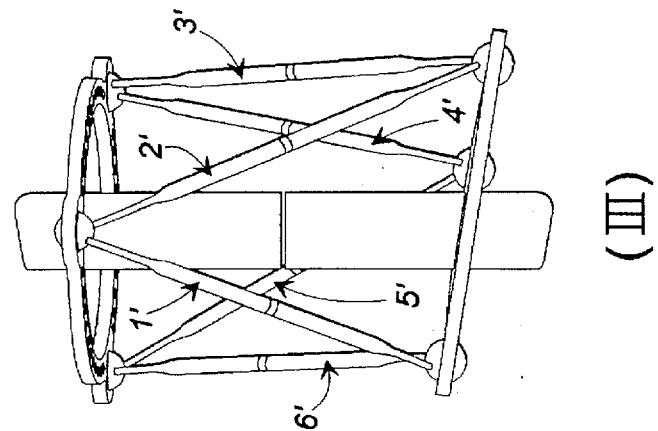
FIG. 30 illustrates three steps involved in a first unique preferred method of using the device of the current invention, and includes a perspective view of a preferred embodiment in a first orientation (I), a diagram illustrating the measurement of various parameters used in accordance with the unique preferred method of the present invention (II), and a perspective view of a preferred embodiment in a second orientation (III).
Figure 30:
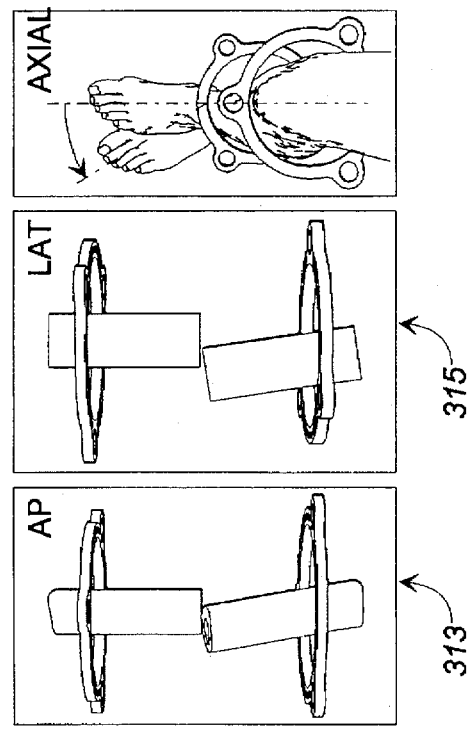
Figure 30:
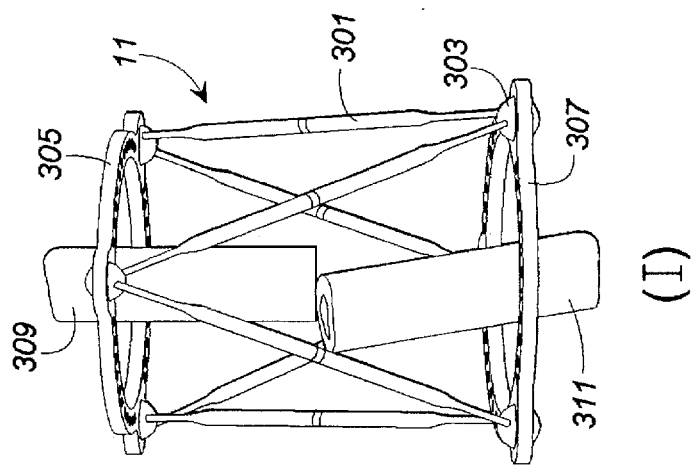
Figure 31:
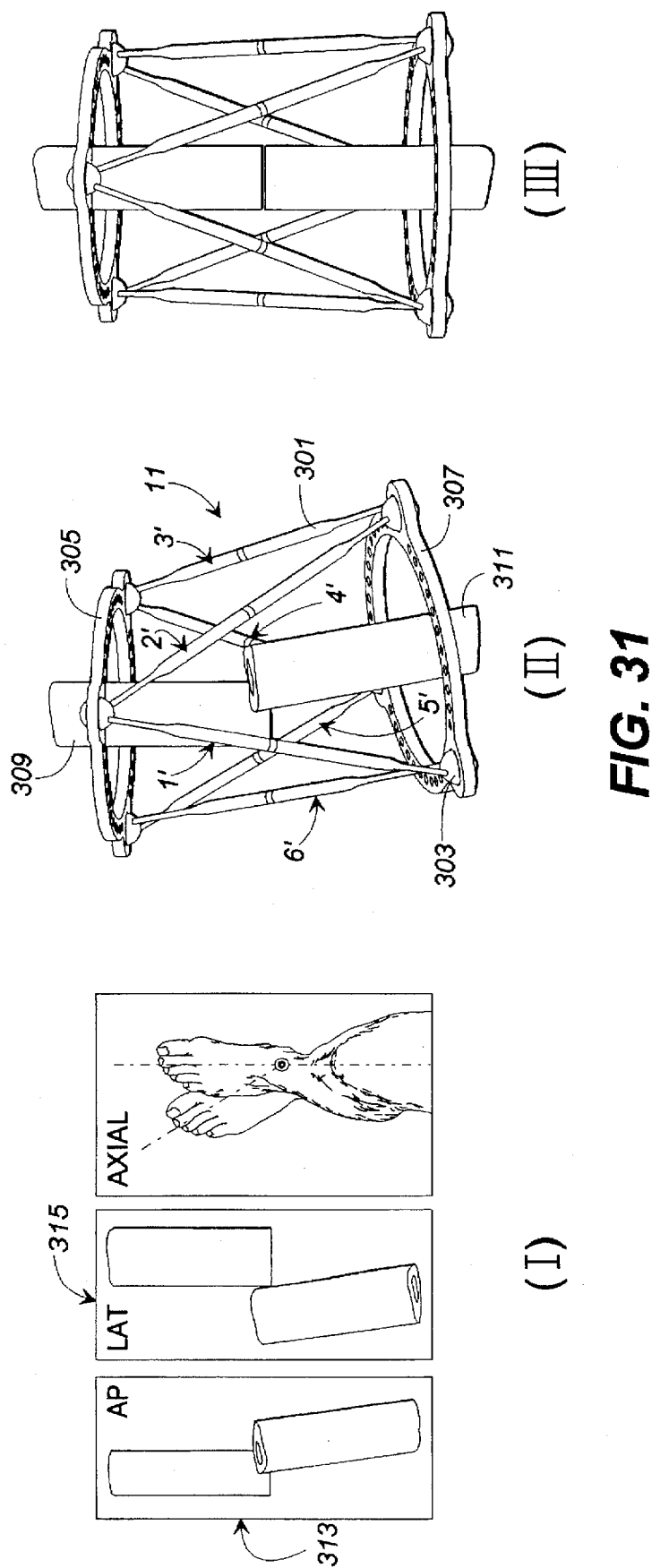
FIG. 31 illustrates three steps involved in a second unique preferred method of using the device of the current invention, and includes a diagram illustrating the measurement of various parameters used in accordance with the unique preferred method of the present invention (I), a perspective view of a preferred embodiment in a first orientation (II), and a perspective view of a preferred embodiment in a second orientation (III).

Because of the unique design of the present external fixator, by adjusting the length of one or more of the adjustable struts, the device can be configured to mimic or mirror virtually any bone deformity. As illustrated in FIGS. 30 and 31, there are two preferred methods of using the device of the current invention. In accordance with the first method illustrated in FIG. 30, there are generally three steps. First, the device in its neutral position is placed on the deformity (I). The deformity is then analyzed and characterized in terms of a variety of parameters (II). These parameters are then used to determine the appropriate length of each strut that is required to configure the device to mirror the deformity (III), and thereby correct the deformity. This method shall be referred to herein as the acute deformity technique. In accordance with the second method of the present invention as illustrated in FIG. 31, the deformity is first characterized in terms of a variety of parameters and the anticipated positioning of the device (I). The length of each strut is then adjusted so that the device is configured to mimic the deformity and the device is placed on the deformity (II). The length of each strut is again adjusted to reconfigure the device back to its neutral position (III), and thereby correct the deformity. This method shall be referred to herein as the chronic deformity technique. As described in greater detail herein below, the strut lengths necessary to reproduce (i.e., the chronic technique) or compensate (i.e., the acute technique) a given deformity are determined using various orthopaedic and geometric principles.

A third preferred method of using the device of the current invention can be used for either chronic deformities or residual deformities. In accordance with this technique, a deformed device (i.e., a device wherein each of the strut lengths are not equal) is place on a deformity, and the deformity is characterized in terms of the geometric relationship of the deformity segments to one another, and to the device. Based on this geometric characterization, the new effective lengths of the struts that are required to correct the deformity are determined, wherein such new effective lengths are not the same, i.e. the device remains deformed after the deformity is corrected.

A. The Chronic Technique

The chronic technique of the present invention is generally used to correct congenital deformities and acquired or post traumatic malunion or nonunion deformities. In general, the unique process of using the device of the present invention in accordance with the chronic technique for correcting a deformity between first and second bone segments includes the following steps. Referring to FIG. 31 (I), in accordance with the chronic technique, the surgeon measures anterior-posterior radiograph 313, lateral-medial radiograph 315, and performs a clinical exam of the bone, which yield six deformity parameters. Based on a further clinical examination, the surgeon determines which size device should be used. The selected device size provides three device parameters. The surgeon then anticipates the relative position of the deformity with respect to the device based on pre-op planning, thus providing four mounting parameters. These thirteen parameters are input to a deformity computer or calculator program based on a general deformity equation, which returns six specific new strut lengths that will configure the device 11 to exactly mimic the deformity. The struts are then adjusted to the new strut lengths, and the device is attached to the skeleton (II). The deformity will be substantially corrected when the struts are restored to their neutral length (III).

More specifically, the unique process of using the device of the present invention in accordance with the chronic technique for correcting a deformity between first and second bone segments includes the following steps:

1. determining the deformity parameters, which include the following measurements of the position of the first bone segment relative to the second bone segment as determined from radiographs and a clinical examination:
   a. anterior-posterior (AP) displacement as seen on the lateral-medial view,
   b. lateral-medial (LAT) displacement, as seen on the AP view,
   c. axial displacement, as seen on either the LAT or AP view,
   d. AP angulation, as seen on the LAT view,
   e. LAT angulation, as seen on the AP view,
   f. axial rotation, as determined through a clinical examination;
2. determining an origin at the deformity site that will act as a convenient reference point, preferably it is at the same level that the AP and LAT displacements are measured;
3. selecting an appropriate size device that will provide the device parameters, which include the effective diameter of the first base member, the effective diameter of the second base member, and the initial neutral length of the struts;

4. predetermining an appropriate location on the first bone segment 309 for attachment of the first base member 305 to the first bone segment 309, and determining the device eccentricities if the device is positioned at such predetermined appropriate location, wherein the device eccentricities include:
   a. the vertical distance from the first base member 305 to the origin,
   b. the horizontal displacement of the origin from the centerline of the device 11, whereby the horizontal displacement consists of anterior-posterior displacement and lateral-medial displacement, and
   c. a predetermined orientation of the device and the amount the second bone fragment is rotated about its axis from its correct position;

wherein the first base member is considered to be the moving base member and the second base member is considered to be the stationary reference base member;

5. calculating the effective length of each strut 301 that is required to configure the device to mimic the deformity if the device were placed on the bone segments 309, 311 at the predetermined appropriate location;
6. adjusting the effective length of each strut 301 to configure the device to mimic the deformity;
7. attaching the first attachment mechanism to the first bone at the predetermined appropriate location, and attaching the second attachment mechanism to the second bone; and
8. adjusting the effective length of each strut 301 to its initial neutral length, and thereby substantially correcting the deformity.

B. The Acute Technique

The acute technique is typically used for acute fracture reduction. In general, the unique process of using the device of the present invention in accordance with the acute technique includes the following steps.

Referring again to FIG. 30, the surgeon first attaches an appropriately sized device around the fracture with the struts at their neutral length (I). The three device parameters are determined based on the device size that is selected. Standard reduction techniques are utilized as the neutral device is applied. Postoperatively, AP and LAT radiographs 313, 315 are obtained and a clinical exam is performed (II). From these radiographs and the clinical exam six fracture deformity parameters, and four mounting parameters are measured. These thirteen parameters are input to a deformity computer or calculator program based on the general deformity equation, which returns six specific new strut lengths to adjust the fixator 11 to exactly mirror the deformity. The deformity will be fully corrected when the struts are moved to their new lengths (III).

More specifically, the unique process of using the device of the present invention in accordance with the acute technique for correcting a deformity between first and second bones segments includes the following steps:

1. selecting an appropriate size device and attaching the first attachment mechanism to the first bone segment 309, and attaching the second attachment mechanism to the second bone segment 311; the selected device size will provide the device parameters, which include the effective diameter of the first base member, the effective diameter of the second base member, and the initial neutral length of the struts;
2. determining the deformity parameters, which include the following measurements of the position of the first bone segment 309 relative to the second bone segment 311:
   a. AP displacement as seen on the LAT view,
   b. LAT displacement, as seen on the AP view,
   c. axial displacement, as seen on either the LAT or AP view,
   d. AP angulation, as seen on the LAT view,
   e. LAT angulation, as seen on the AP view,
   f. axial rotation, as determined through a clinical examination;
3. determining an origin at the deformity site that will act as a convenient reference point, preferably it is at the same level that the AP and LAT displacements are measured;
4. determining the device eccentricities, which include:
   a. the vertical distance from the first base member to the origin,
   b. the horizontal displacement of the origin from the centerline of the device, whereby the horizontal displacement consists of anterior-posterior displacement and lateral-medial displacement, and
   c. a predetermined orientation of the device and the amount the second bone segment is rotated about its axis from its correct position;

wherein the first base member is considered to be the moving base member and the second base member is considered to be the stationary reference base member;

5. calculating the effective length of each strut 301 that is required to configure the device 11 to mirror the deformity; and
6. adjusting the effective length of each strut 301 to configure the device 11 to mirror the deformity, and thereby substantially correcting the deformity.

II. The Device Parameters

In both the deformity technique and the acute technique, the surgeon must select the appropriate device size, i.e., the device parameters. There are three device parameters, including the effective diameter of the first base member 305, the effective diameter of the second base member 307, and the initial neutral length of the struts 301. The effective diameter of a base member 71 is the diameter of a circle that substantially intersects the connectors 303 associated with such base member. In accordance with the preferred embodiment of the present device, as illustrated in FIG. 1, the base members 71 are circular, and therefore their effective diameters are the actual diameters of the base members 71. Alternative base member shapes, however, may be used in the device of the current invention.

III. Determining the Position of the First Bone Segment Relative to the Second Bone Segment (the Deformity Parameters)

The deformity parameters include six measurements that characterize the deformity. Specifically, the six measurements describe the location of one bone segment or fragment relative to the second bone segment or fragment. The six deformity parameters include: AP translation, LAT translation, axial translation, AP angulation, LAT angulation, and axial rotation. Determining the deformity parameters is a step in both the chronic technique (step 1, above) and the acute technique (step 2, above).

In general, the orthopaedic surgeon must identify a common axis (anatomic or mechanical) for the bone segments 309, 311 for use in making the measurements. AP and LAT radiographs are taken to assist the surgeon in identifying the deformity parameters. Anatomic or mechanical axes can be assessed by using long films (including hip, knee, and ankle) with a radiographic ruler.

We have found that it is useful to consider one fragment as being a stationary. reference and consider the other fragment as moving or deformed. Orthopaedic convention typically characterizes a deformity of the distal fragment with respect to a proximal fragment, i.e., the proximal fragment is the reference fragment, and the distal fragment is the moving fragment. The unique method of using the fixator of the current invention, however, can also be used when the distal fragment is considered the reference fragment, and the proximal fragment is considered the moving or deformed fragment. This atypical characterization of a deformity (i.e., using a proximal fragment as the moving or deformed fragment) is especially useful in proximal tibial nonunions or malunions with a short proximal fragment. The location of the attachment of the proximal base member (using the joint surface and fibular head as landmarks) will be more exactly determined in preoperative planning and in surgery than the level of attachment of the distal base member on the longer distal fragment. It also allows the surgeon to fully characterize the deformity even though the radiographs are too short to include the level of attachment of the distal base member.

Before specifically addressing the determination of the deformity parameters, a sign convention (+/−) must be adopted for the orthopedic reference terminology typically used when discussing the human body. Those of ordinary skill in the art will appreciate that the sign convention we adopt is arbitrary, and any other sign convention can be used. It is merely important that once a standard is selected, it must be consistently applied.

Figure 33:
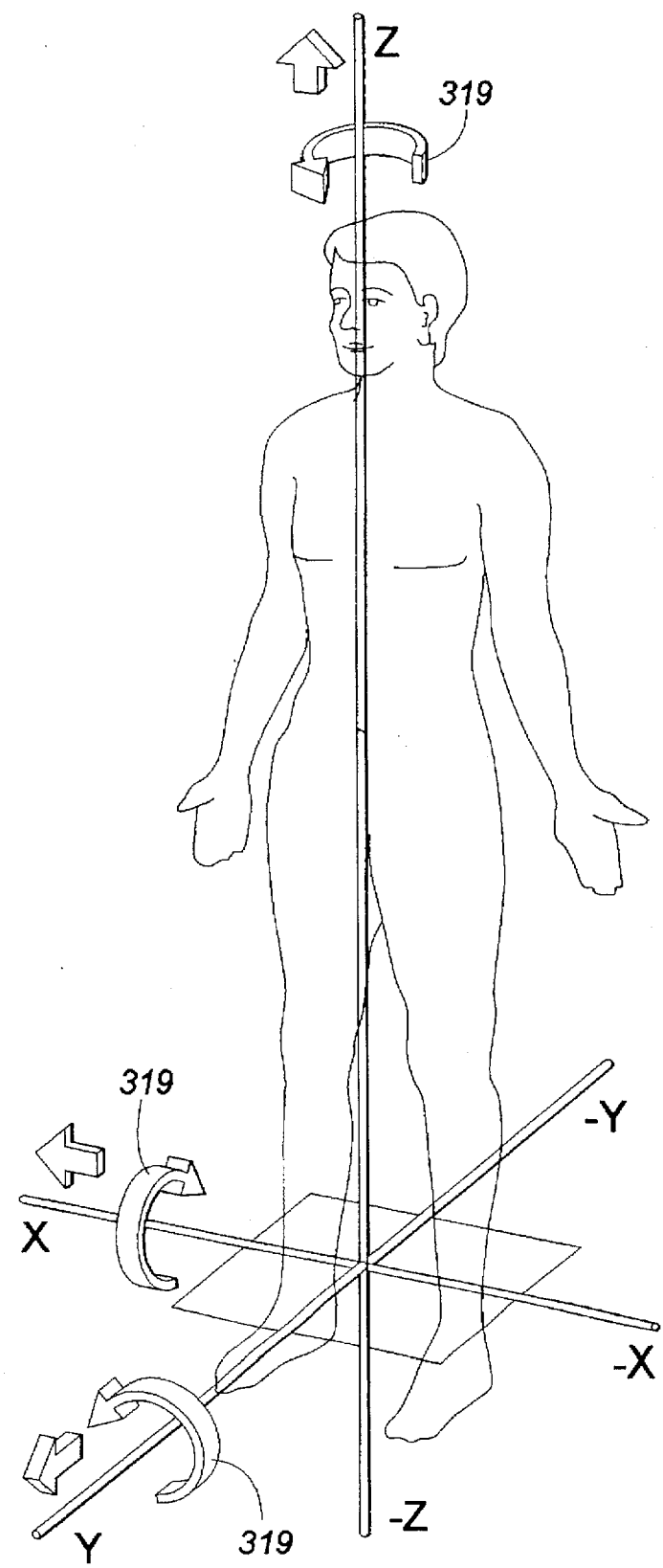
FIG. 33 is a diagram illustrating the sign (+/−) convention adopted for use with a specific embodiment of the method of the current invention.

Referring now to FIG. 33, the sign convention that we have adopted to illustrate the preferred embodiment of the present invention is shown. We have designated the sagittal plane as the Y-Z plane, the coronal plane as the X-Z plane, and the transverse plane as the X-Y plane. The point of interest, or the origin as we will refer to it, is the zero position in our coordinate system. As shown in FIG. 33, all points that are more cephalad than the origin along the Z axis are positive, all points anterior to the origin along the Y axis are positive, and assuming you are working on yourself, all points to the right of the origin along the X axis are positive.

A sign convention must also be adopted for rotational motion. In accordance with the preferred method of the present invention, the right-hand rule should be applied to determine the sign for rotational motion. According to the right-hand rule, with the right thumb pointing along a positive reference axis, positive rotation about that axis is in the direction of the finger tips. The arrows 319 in FIG. 33 indicate the positive direction for rotation about each axis as determined by the right-hand rule.

To more specifically illustrate the use of the preferred sign convention, the following table lists the conventional orthopaedic terminology and the corresponding mathematical signs for the various translations and rotations of a moving distal fragment with respect to a reference proximal fragment for left and right tibiae:

|  | Left | Right |
|---|---|---|
| Varus | − | + |
| Valgus | + | − |
| Flexion | − | − |
| Extension | + | + |
| Internal Rotation | − | + |
| External Rotation | + | − |
| Medial | + | − |
| Lateral | − | + |
| Anterior | + | + |
| Posterior | − | − |
| Short | + | + |
| Long (rare) | − | − |

To further more specifically illustrate the use of the preferred sign convention, the following table lists the conventional orthopaedic terminology and the corresponding mathematical signs for the various translations and rotations of a moving proximal fragment with respect to a reference distal fragment for left and right tibiae.

|  | Left | Right |
|---|---|---|
| Varus | + | − |
| Valgus | − | + |
| Flexion | + | + |
| Extension | − | − |
| Internal Rotation | + | − |
| External Rotation | − | + |
| Medial Displ. of Prox. Fragment | + | − |
| Lateral Displ. of Prox. Fragment | − | + |
| Anterior Disp. of Prox Fragment | + | + |
| Posterior Disp. of Prox Fragment | − | − |
| Short | − | − |
| Long (rare) | + | + |

Figure 32:
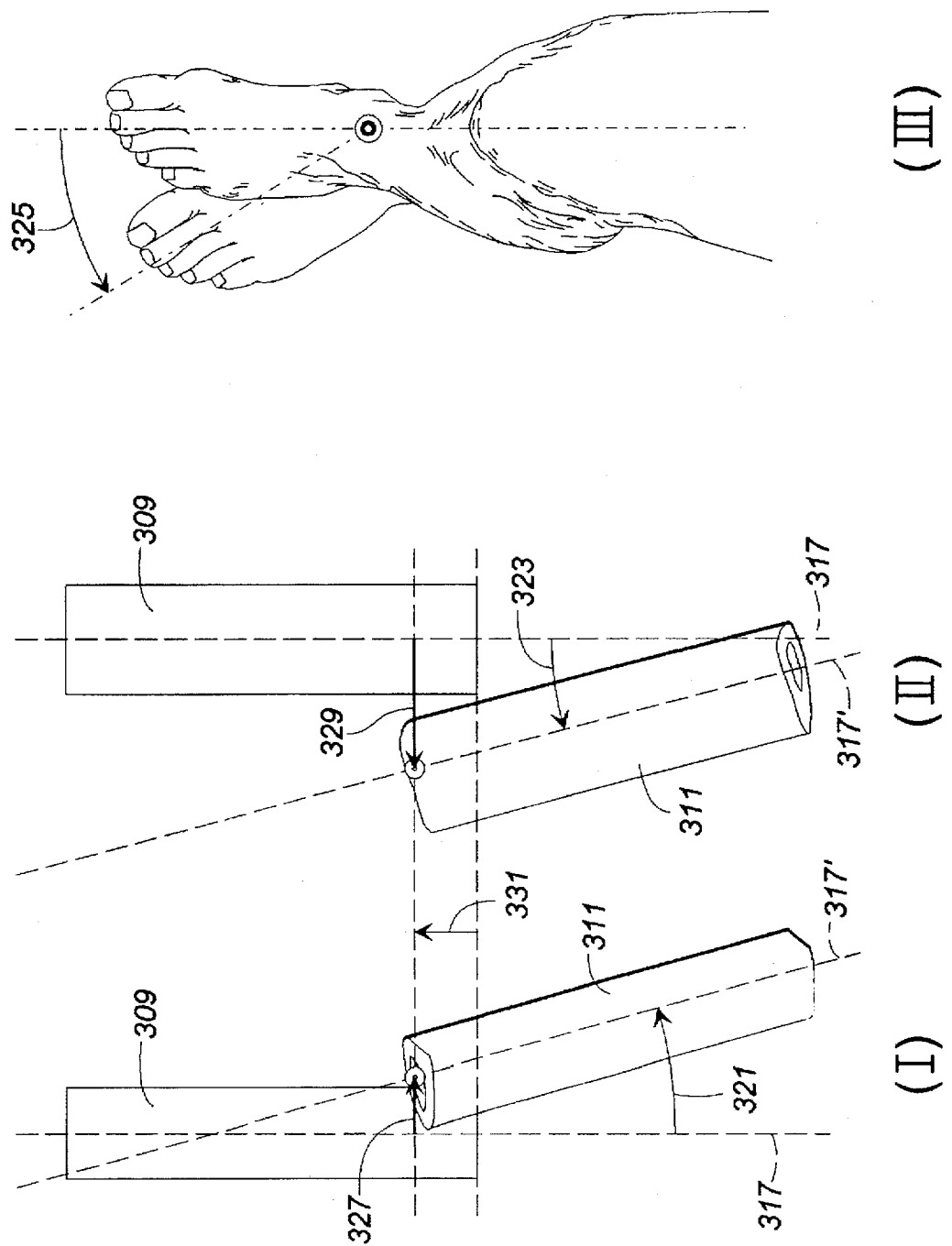
FIG. 32 is a diagram illustrating how deformity parameters are determined for a deformed tibia in accordance with a preferred method of the current invention, including an illustration of an anterior-posterior radiograph (I) of a fractured tibia, lateral-medial radiograph (II) of a fractured tibia, and a diagram illustrating a clinical exam (III).

After a common axis 317 is identified and a sign convention adopted, the deformity parameters can be determined. FIG. 32 illustrates how the deformity parameters are determined for a deformed tibia. For this illustration, we have chosen the proximal fragment 309 as the reference fragment, and the distal fragment 311 as the moving fragment. An AP radiograph (I) and LAT radiograph (II) are made of the deformity. As shown in FIG. 32, the centerline 317 of the reference fragment 309, and the centerline 317' of the deformed moving fragment 311 are drawn. Both centerlines 317, 317' extend along the common axis of the corrected bone. The AP angulation is indicated by the arrow 321 and the LAT angulation is indicated by the arrow 323, and are determined by using traditional methods to measure the divergence of the centerlines 317, 317' drawn in each fragment 309, 311. Axial rotation (III) (internal or external rotation) is assessed clinically or with special films. The axial rotation, as indicated by the arrow 325, will be the amount of rotation about the centerline of the bone from its normal position.

In accordance with the preferred method of using the device of the present invention, the translation deformity parameters are determined as follows. As shown in FIG. 32, AP translation (I) and LAT translation (II) (i.e., displacement) is the perpendicular distance from the reference fragment's centerline 317 to the moving fragment's centerline 317' at the level of the origin, which is usually the interior end of the moving fragment 311. The AP translation in FIG. 32 is indicated by the arrow 327. The LAT translation in FIG. 32 is indicated by the arrow 329. The axial translation can be measured on either the AP or the LAT radiograph, and is the distance between the interior ends of the fragments 309, 311 measured along the reference fragment centerline 317. The axial translation in FIG. 32 is indicated by the arrow 331. The signs for each of the deformity parameters is based on the coordinate axes and the right-hand rule as discussed above.

IV. Determining the Origin

In addition to determining the deformity parameters that characterize the skeletal deformity or fragment-to-fragment orientation, the surgeon must also determine the eccentricities that characterize the skeleton-to-device orientation. As a result, a point must be selected on the skeleton to act as a reference for characterizing the skeleton-to-device orientation. We refer to that reference point as the "origin."

In accordance with both the chronic technique (step 2, above), and acute technique (step 3, above), the surgeon must determine an "origin." In accordance with the preferred method of using the device of the present invention, the origin will be the point about which the corrective rotation will occur. The z-coordinate of the origin is preferably the same as the level at which the AP and LAT displacements were measured. The origin must be properly selected to avoid compression, distraction, or displacement at the osteotomy/nonunion site during the correction of the deformity.

Figure 36A:
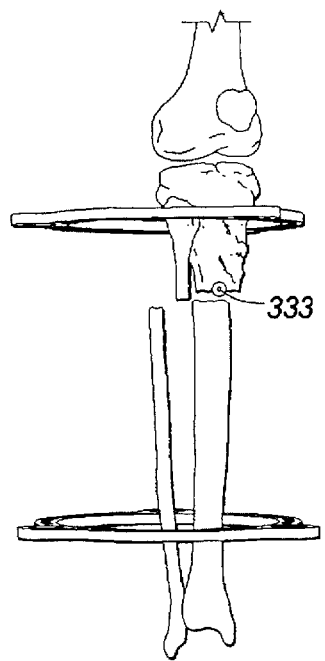
FIG. 36 is a diagram illustrating a preferred selection of an origin in accordance with the method of the current invention, and includes an anterior-posterior view (A), a lateral-medial view (B), and a cross-sectional axial view (C) of the base members of the current invention mounted on a deformity having significant axial rotation.
Figure 36B:
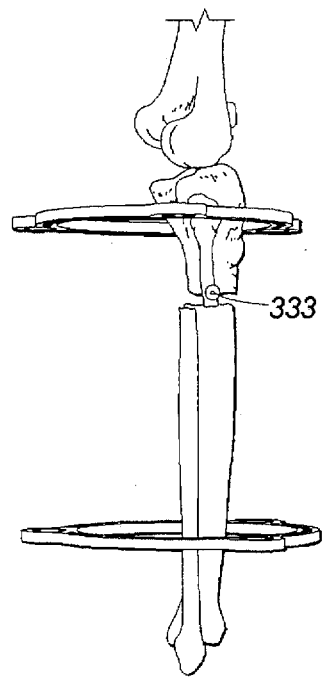
Figure 36C:
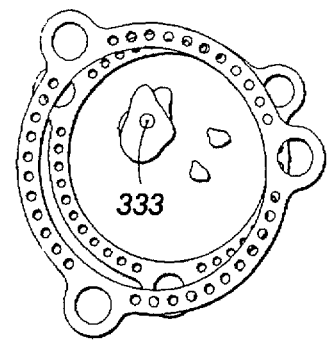

FIGS. 34–36 illustrate the preferred origins for several situations. As shown in FIG. 34, if the deformity consists of translations only, the center of the base member 305 at the level of the interior end of the moving fragment can be established as the origin 333. When pure translation deformities are involved, however, any point may be selected as the origin 333. As shown in FIG. 35, if the deformity has significant angulation, a point on the convex cortex of the interior end of the moving fragment should be chosen as the origin 333 to prevent a compressive hinge and excessive preload on pins and wires. As shown in FIG. 36, if the deformity contains significant rotation, the origin 333 should be chosen as the center of the moving fragment at the deformity to prevent unwanted translation of the moving fragment as it is rotated. Alternatively, the origin can be placed at the convexity of the deformity rather than the center of the moving fragment. Rotation at the convex cortex will be necessary especially for correction of congenital deformities, malunions, and stiff nonunions which require minimal or no lengthening. Otherwise, too much impaction and over constraint at the convex cortex may result in excessive preload on pins and wires and under-correction of the deformity.

V. Characterizing the Skeleton-to-Device Orientation (the Device Eccentricities)

After the origin 333 is selected, the surgeon can characterize the position of the device 11 relative to the origin 333. In accordance with the preferred method of the present invention, the position of the device relative to the bone is characterized in terms of four device eccentricities, which include the axial eccentricity, the lateral eccentricity, the AP eccentricity, and the rotational eccentricity. FIGS. 37–43 illustrate the determination of the device eccentricities. For purposes of illustration, the distal fragement and base member shall now be considered the reference fragment and base member, and the proximal fragment and base member shall be considered moving. Specifically, the second bone fragement 311 and the second base member 307 are considered the reference points, and the first base member 305 and the first bone fragement 309 are considered the moving components. As outlined above, the device eccentricities are used as part of both the chronic technique (step 3, above) and the acute technique (step 4, above).

A. Sign (+/−) Convention for the Eccentricities

As previously noted, it is important that a consistent sign convention be adopted and consistently applied in accordance with unique method described herein. In accordance with the preferred sign convention discussed above, the following table outlines what the signs are for the various eccentricities.

| Mounting Parameters Characterizing Bone to Frame Orientation | | |
|---|---|---|
| Rotary Eccentricity | | |
| | Left | Right |
| If reference fragment is rotated | | |
| Internally* | − | + |
| Externally* | + | − |
| *with respect to reference ring | | |
| LAT Eccentricity/AP Eccentricity | | |
| | Left | Right |
| If origin is | | |
| Medial* | + | − |
| Lateral* | − | + |
| Anterior* | + | + |
| Posterior* | − | − |
| *to centerline of moving ring | | |
| Axial Eccentricity | | |
| | Left | Right |
| Distal Ring Moving If origin is | | |
| Proximal* | + | + |
| Distal (Rare)* | − | − |
| Proximal Ring Moving If origin is | | |
| Proximal (Rare)* | + | + |
| Distal* | − | − |

*to moving ring

B. Axial Eccentricity

Figure 37:
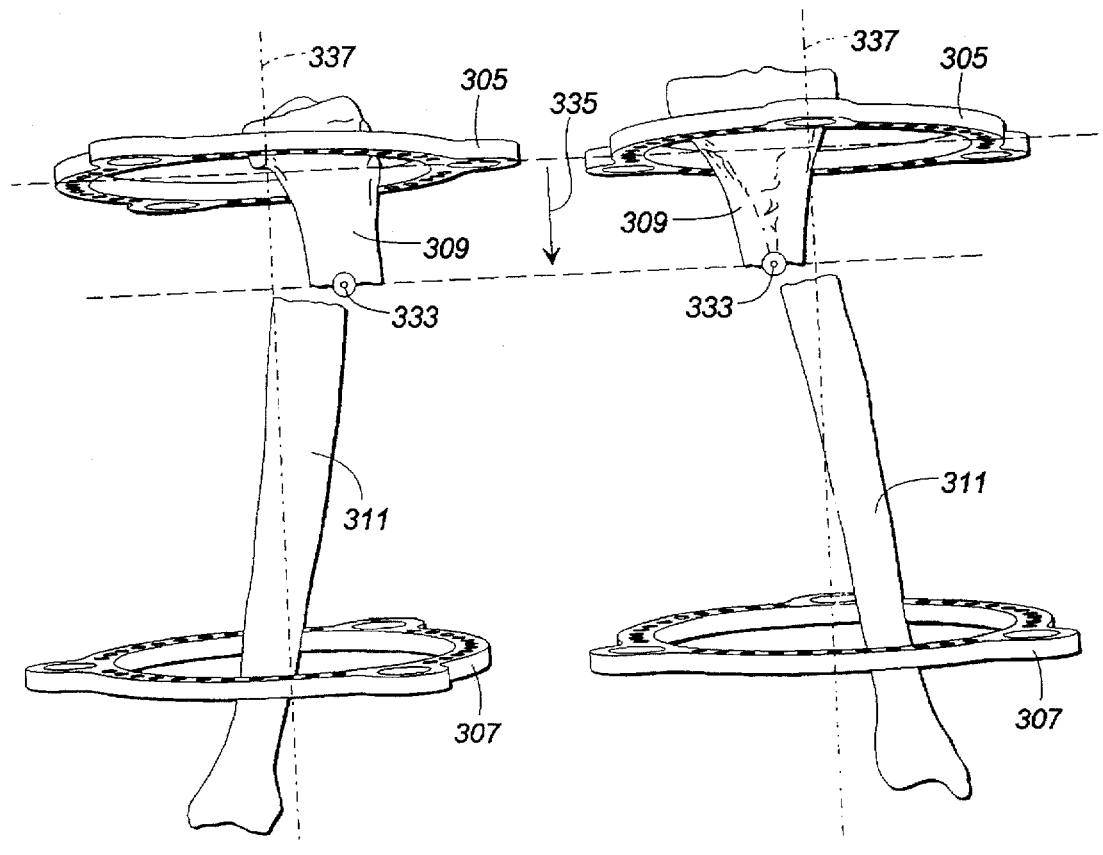
FIG. 37 is a perspective view of the base members of the present device mounted on a fractured bone, and illustrates both a lateral-medial radiograph (I) and a anterior-posterior radiograph (II) of a deformity.

As illustrated in FIG. 37, the axial eccentricity is indicated by the arrow 335, and is the measurement of length parallel to the device centerline 337 from the level of the moving base member 305 to the origin 333. This can generally be measured on an AP radiograph (I) or LAT radiograph (II). This measurement partially specifies the orientation of the bone with respect to the device 11.

C. AP and Lateral Eccentricity of Bone with Device

Figure 38:
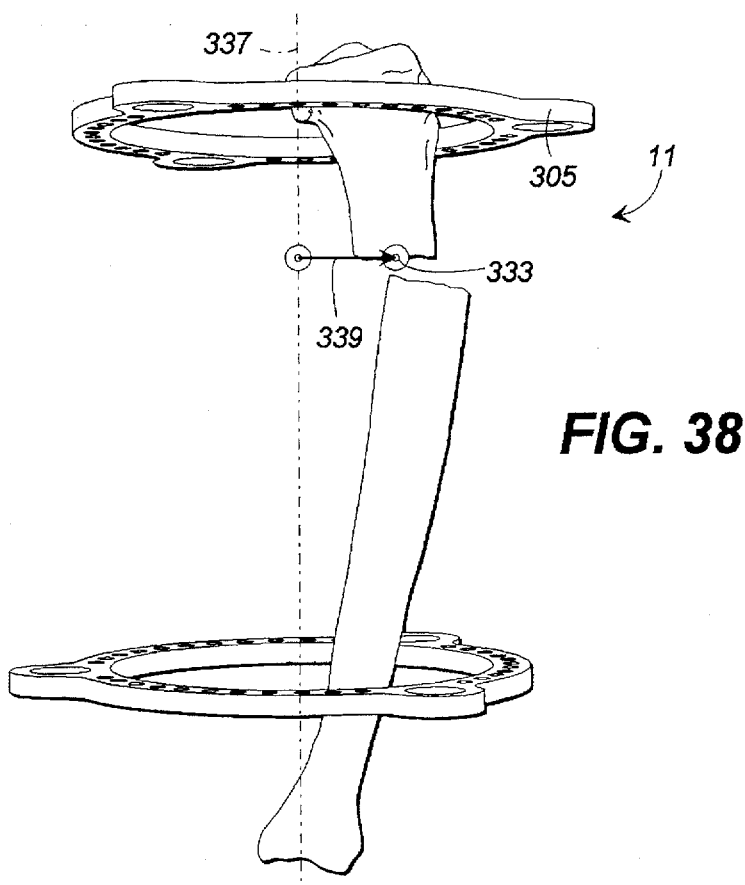
FIG. 38 is a perspective view of the base members of the present device mounted on a fractured bone, and illustrates a lateral-medial radiograph of a deformity.
Figure 39:
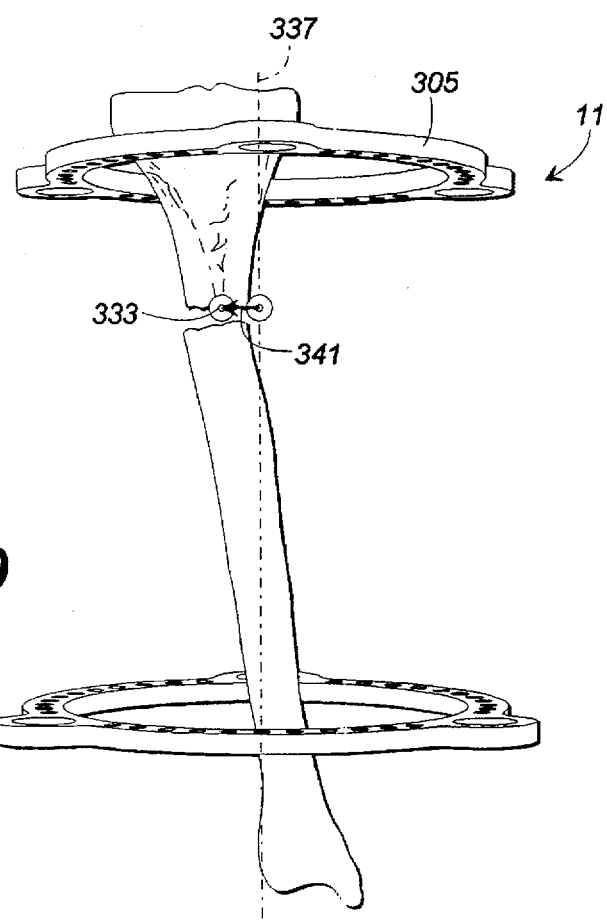
FIG. 39 is a perspective view of the base members of the present device mounted on a fractured bone, and illustrates a anterior-posterior radiograph of a deformity.
Figure 40:
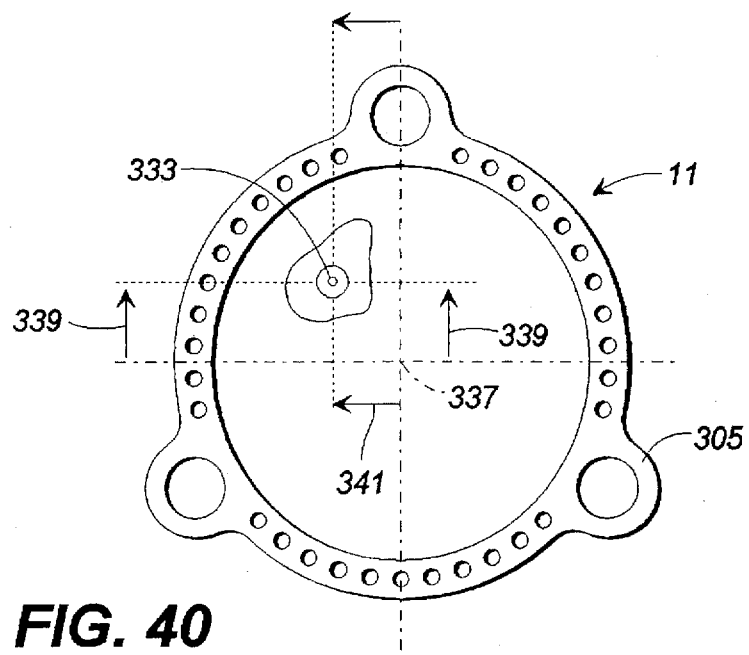
FIG. 40 is a cross-sectional view of the device of the current invention mounted on a tibia, and illustrates the determination of the anterior-posterior eccentricity and the lateral-medial eccentricity in accordance with a preferred method of using the device of the current invention.

In most tibial mountings with circular fixators, the tibia is located anterior to the geometric center of the base member. Referring to FIG. 38, a lateral radiograph of a deformity is shown. As illustrated in FIGS. 38 and 40, in accordance with a preferred method of the present invention, the surgeon must measure the distance from the centerline 337 of the device 11 to the origin 333 within a plane parallel to the moving base member 305. This distance is the lateral eccentricity as indicated by arrow 339. Referring now to FIG. 39, an AP radiograph is shown. As illustrated in FIGS. 39 and 40, if the tibia fragments are not centered on the AP radiograph, the surgeon should measure the distance from the centerline 337 of the device 11 to the origin 333 within a plane parallel to the moving base member 305. This distance is the AP eccentricity as indicated by the arrow 341.

In accordance with the chronic technique outlined above, when treating stiff nonunions, malunions, and congenital deformities, the position of the bone with respect to the device 11 can be anticipated. Corresponding values for the axial eccentricity, lateral eccentricity, and AP eccentricity are entered into a general deformity equation, as set forth hereinbelow, to determine exact strut lengths for the device to mimic the given deformity while maintaining the anticipated relative position of the device and bone.

In accordance with the acute technique outlined above, when treating fresh fractures, the axial eccentricity, lateral eccentricity, and AP eccentricity are measured on postoperative films. Similar to the chronic technique, these values are entered into a general deformity equation to determine exact strut lengths for the device to compensate for or mirror the acute deformity.

D. Rotary Eccentricity

Figure 41:
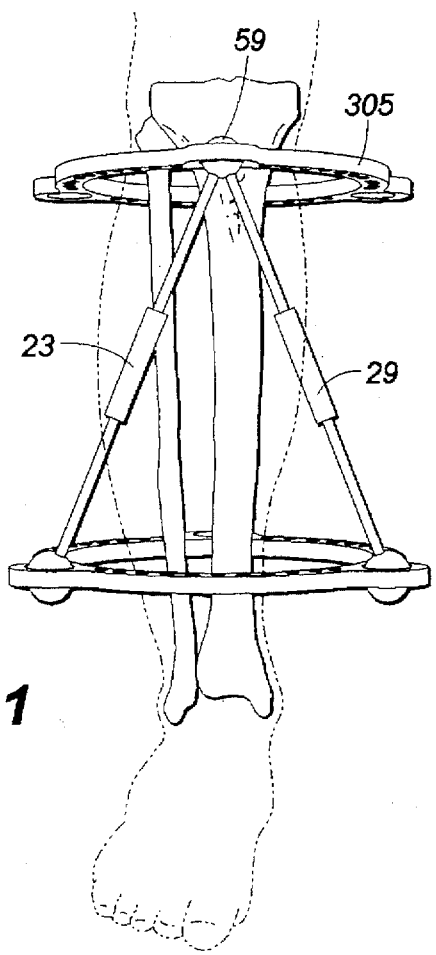
FIG. 41 is a perspective view of the device of the current invention mounted on a tibia.
Figure 42:
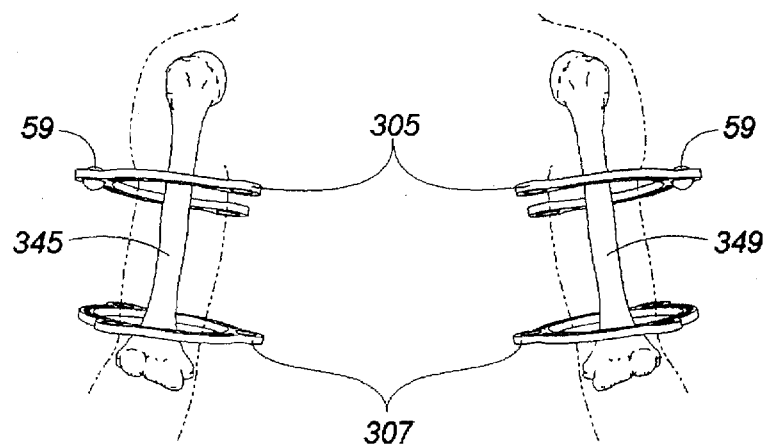
FIG. 42 is a perspective view of the ring members of the device of the current invention mounted on various portions of a human body.
Figure 43:
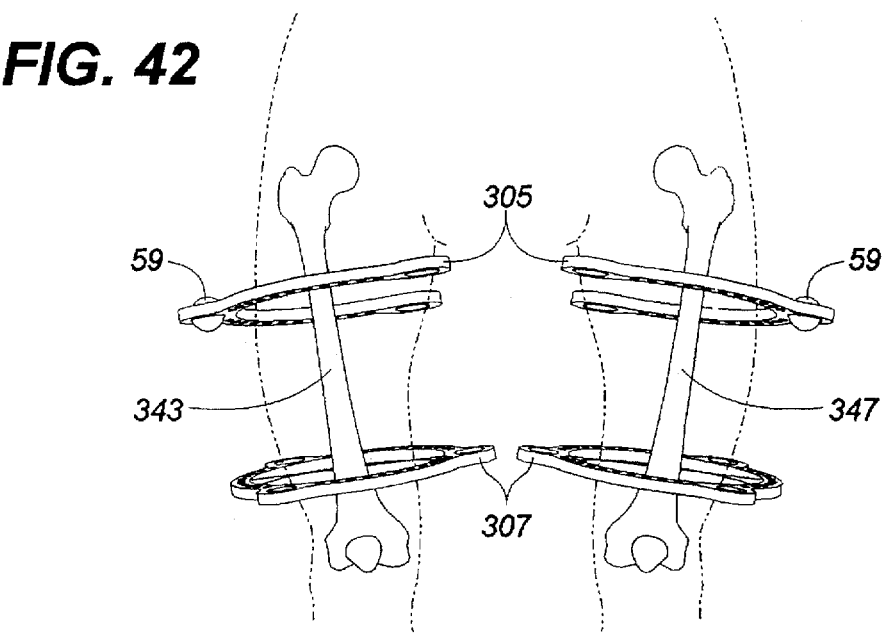
FIG. 43 is a cross-sectional view of the device of the current invention mounted on a tibia, and illustrates the determination of the rotary eccentricity in accordance with a preferred method of using the device of the current invention.
Figure 43:
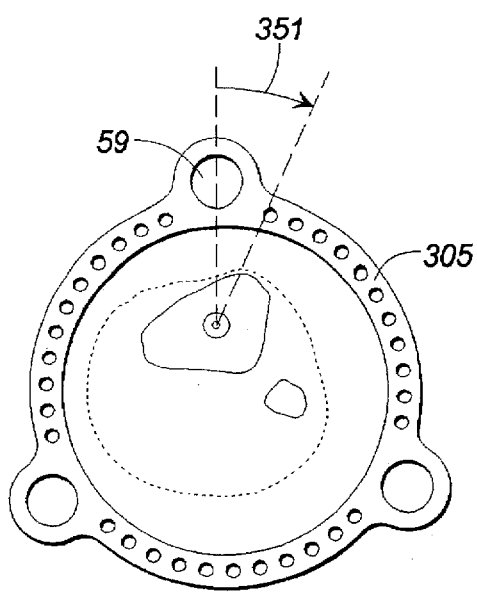

In order to characterize the rotational position of the device 11 relative to the skeleton, a preferred orientation of the device 11 relative to the skeleton must be adopted to provide a frame of reference. Those of ordinary skill in the art will appreciate that the preferred rotational orientation that we have selected is arbitrary, and other reference orientations may be selected. We have found that in accordance with the preferred method of the present invention, a convenient reference orientation, as illustrated in FIG. 41, is with the connector 59 of the proximal base member 305 (i.e., the master connector) between strut 23 and strut 29 located exactly anterior. This preferred orientation is appropriate for both tibiae and both forearms. Referring to FIG. 42, the preferred device orientation is shown for the right and left femur and humerus. For the right femur 343 and right humerus 345 the preferred orientation is with the master connector 59 rotated 90 degrees to the right (i.e., −90°). For the left femur 347 and left humerus 349 the preferred orientation is with the master connector 59 rotated 90 degrees to the left (i.e., +90°). FIG. 43 illustrates the rotary eccentricity for a tibia. The rotary eccentricity indicated by line 351, and is determined clinically as the amount of rotation of the bone relative to the device from the preferred orientation.

When used for fractures in accordance with the acute technique, the device 11 may be inadvertently malrotated when applied. To compensate for the malrotated device, the rotary eccentricity will be the angular position of the anatomic sagittal plane of the reference fragment with respect to the reference base member.

VI. Calculating the Requisite Length of Each Strut

In the 19th century, Michel Chasles was the first to realize that the complex repositioning of an object in 6-axes (three translations plus three rotations) could be duplicated by rotation of a threaded nut along a threaded shaft. In general this shaft is oblique to the reference axes. The offset from the center of the shaft will satisfy two translations and the pitch of the thread will satisfy the third translation. Rotation around this oblique shaft is the equivalent to three orthogonal rotations. Consequently, Chasles' oblique shaft (the Chasles Axis) can serve as a useful model for understanding deformity correction. This oblique Chasles Axis is the ultimate Ilizarov hinge axis, in that it can simultaneously correct all three malrotations.

Figure 44:
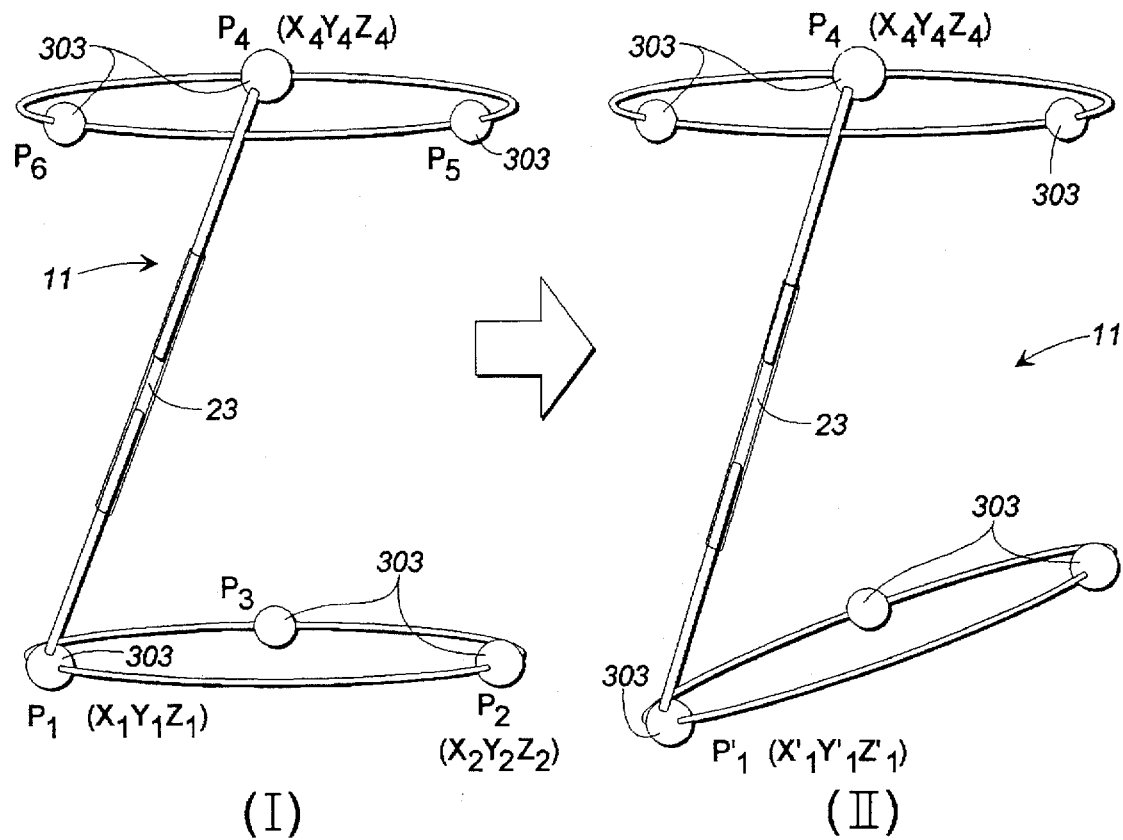
FIG. 44 is a partial perspective view of the device of the current invention in its neutral position (I), and its deformed position (II).

The method of the current invention utilizes a general deformity equation that is based on a vector analysis of rotation measured on the radiographs and a clinical examination, which yields a Chasles Axis and an associated rotation matrix. In general, the unique position of any object can be determined by locating three noncollinear points on that object. Referring to FIG. 44, the method of using the device of the present invention uses the general deformity equation to determine the location (P) of the connectors 303 of the device 11 when the device is in (1) its neutral position I and (2) its deformed position (II). More specifically, the unique method of the current invention utilizes a general deformity equation to determine the connector coordinates for each strut, (e.g., $P_1(X_1, Y_1, Z_1)$ and $P_4(X_4, Y_4, Z_4)$ For strut 23 in its neutral position (I) and $P_1'(X_1', Y_1', Z_1')$ and $P_4(X_4, Y_4, Z_4)$ For strut 23 in its deformed position (II). The pythagorean theorem is then used to solve for the distance between the connectors, which equals the appropriate length for the strut.

Figure 45:
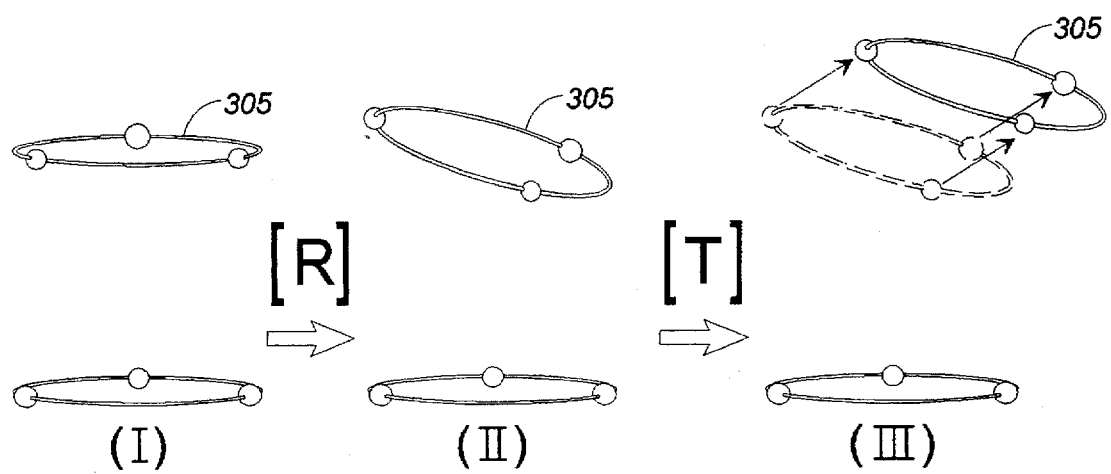
FIG. 45 is a diagram illustrating how the rotational and translational components of the general deformity equation are applied in accordance with a preferred method of using the device of the current invention.

Referring to FIG. 45, when mimicking or mirroring a deformity, one of the base members 305 is rotated and/or translated. In accordance with a preferred method, one starts with a neutral device (I), and the rotational motion is first applied (II). Thereafter the translation motion is applied (III). The general deformity equation, therefore, includes a rotation component [R] and a translation component [T]. The Following discussion first analyzes the rotation component of the general deformity equation, and then addresses the translation component.

A. Rotation Component of the General Deformity Equation

The rotation component of the general deformity equation consists of a rotation matrix based on the Chasles Axis, and can be expressed as:

$$|R| \begin{bmatrix} X \\ Y \\ Z \end{bmatrix} = \begin{bmatrix} X^1 \\ Y^1 \\ Z^1 \end{bmatrix}$$

With this rotational matrix, the initial coordinates (X,Y,Z) of any point of interest in the one state (e.g., the normal state) can be used to determine the new coordinates (X',Y',Z') of the same point in the second state (e.g., the deformed state).

Utilizing the sign convention discussed above, the Chasles Axis can be developed as a vector, with direction and magnitude. The three contributions to the vector will be based on three angles (i.e., rotations). Two angles are determined from radiographs, and the third angle is determined from a clinical exam.

In going from the normal state to the deformed state, rotation of the fragment around this Chasles Axis will always be positive, based on the right-hand rule; clockwise looking out along the Axis, counterclockwise looking back toward the origin. Realize that the Chasles Axis may be directed along the positive or negative coordinate axis, but that rotation about the Chasles Axis will always be positive going from the normal to the deformed state.

Figure 46:
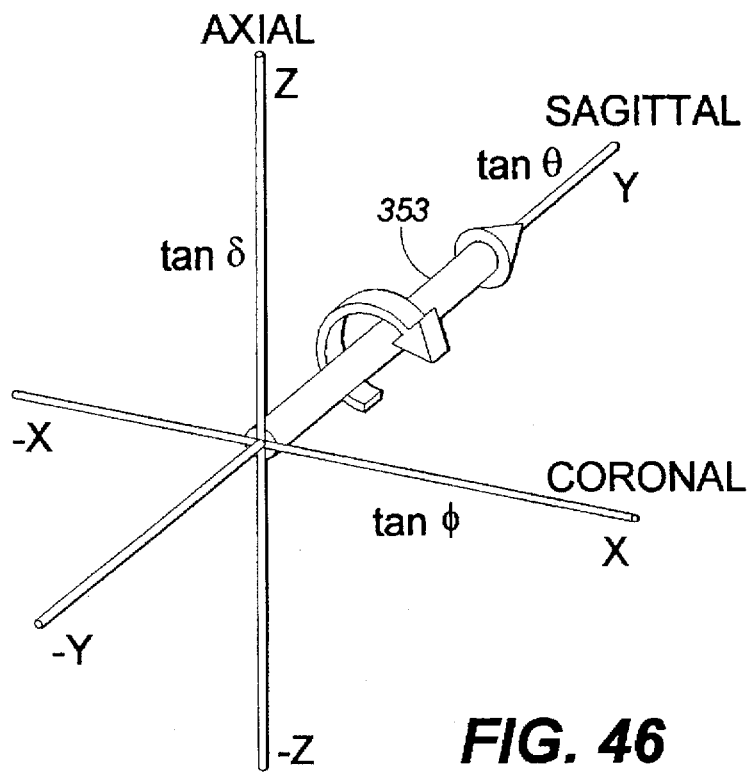
FIG. 46 is an illustration of a vector representation of a Chasles Axis for a one dimensional rotational deformity.

In accordance with the preferred embodiment of the present invention, the following procedure is used to determine the Chasles Axis. To illustrate how the Chasles Axis is determined, we first consider the simplest situation where the deformity is only a one-dimensional angular deformity. Consider a radiograph as a projection of the deformity onto a reference plane. FIG. 32 (I) illustrates such a radiograph. A fractured bone is shown having two fragments 309 and 311 with each fragment having a centerline 317 and 317', respectively. If the angle 321 between centerlines 317 and 317' is θ (consider the right-hand rule to determine sign), then the axis around which such rotation took place is perpendicular to the reference plane, and its orientation (along the positive or negative axis) is determined by the value of tan θ. Thus as illustrated in FIG. 46, for angles >−90° and <+90°, if θ is positive, tan θ is positive, and the Chasles Axis 353 parallels the positive Y coordinate axis and would provide the sagittal hinge to recreate the frontal plane deformity. The magnitude of rotation (σ) in this one-dimensional case is:

$$\sigma = A\tan\sqrt{\tan^2\theta} = \theta$$

where Atan is the arc tangent.

Figure 47:
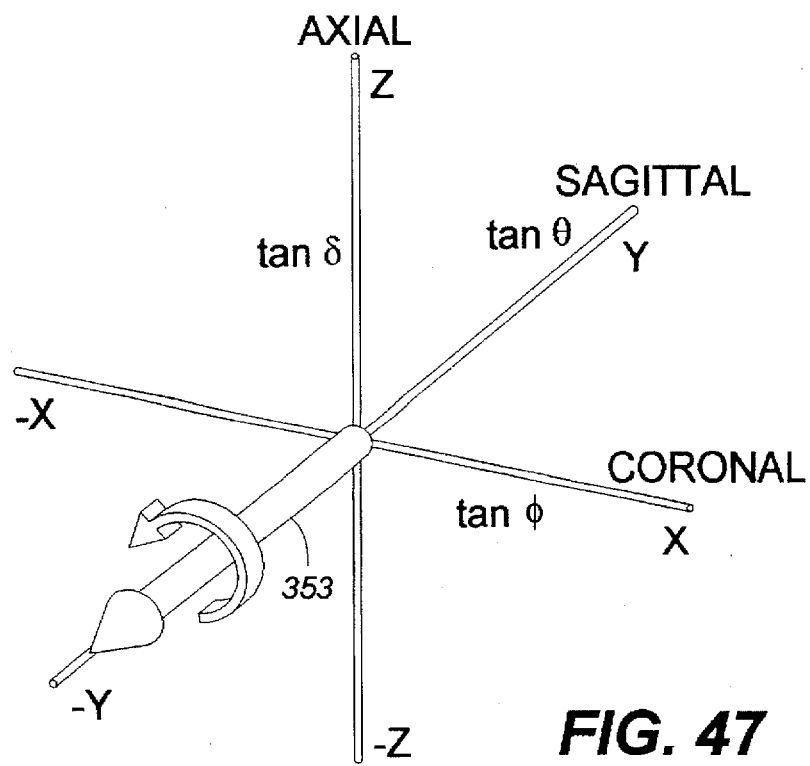
FIG. 47 is an illustration of a vector representation of a Chasles Axis for a one dimensional rotational deformity.

As illustrated in FIG. 47, if the angle on AP radiograph were −θ, then tan −θ is negative and the Chasles Axis would be directed parallel to the negative Y coordinate axis and would provide the sagittal hinge to recreate the frontal plane deformity, but in the opposite direction of the first example. Since we have characterized the Chasles Axis as a vector with directional sense, you will note that the effective rotation of the Chasles Axis in the example illustrated in FIG. 46 is opposite that of the Chasles Axis illustrated in FIG. 47. But rotation around the Chasles Axis will always be positive based on the right-hand rule as is true in the examples illustrated in FIGS. 46 and 47. Thus, by establishing the Chasles Axis as a vector and not just a hinge line, it carries with it a directional sense which when the right-hand rule is applied will always yield the proper direction of rotation. This avoids the problems associated with conventional methods causing confusion concerning which direction to rotate about a hinge, particularly with two-plane and three-plane deformities.

Figure 48:
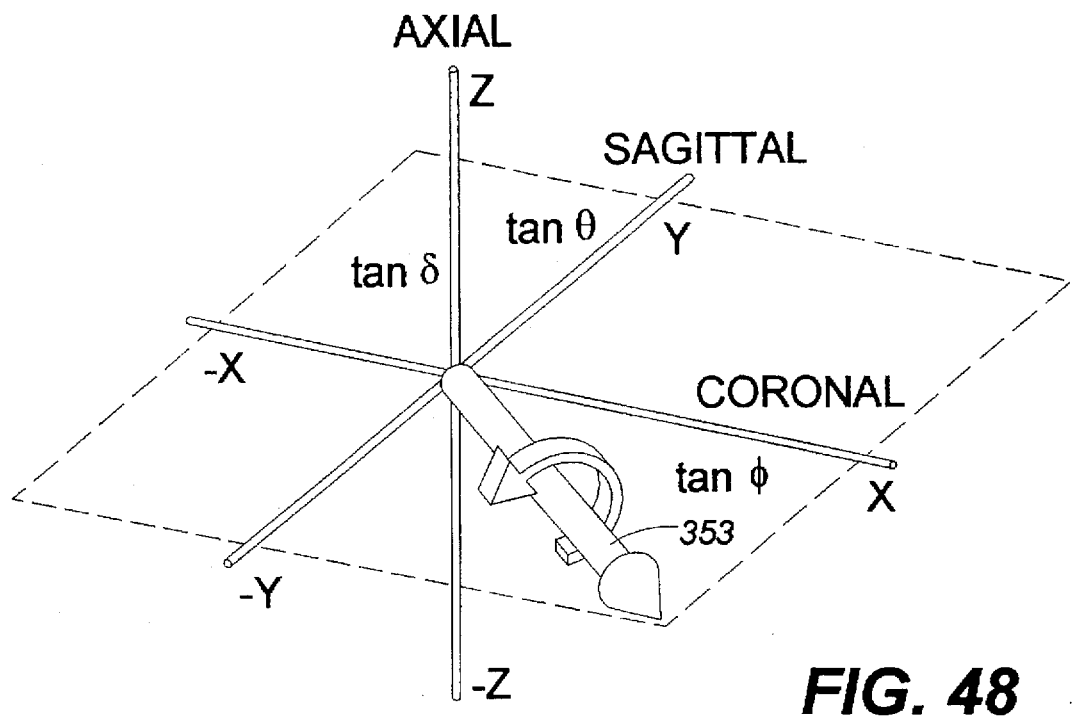
FIG. 48 is an illustration of a vector representation of a Chasles Axis for a two dimensional rotational deformity.

We next consider the case were there is two-dimensional angular deformity with angulation apparent on each of two orthogonal radiographs. For each radiograph determine the angle of deformity and determine its sign based on the right-hand rule. Take the tan of that angle and plot the value along the reference coordinate axis perpendicular to that radiographic plane. The final rotation axis will be the vector sum of the two orthogonal contributions. Not only can the final Chasles Axis lie along the reference axes in special cases, but as illustrated in FIG. 48, the Chasles Axis 353 can exist in any of the four quadrants of space as determined by +/− coronal axis and +/− sagittal axis. The true magnitude of the two-dimensional rotation is:

$$\sigma = A\tan\sqrt{\tan^2\theta + \tan^2\phi}$$

where θ is the amount of rotation measured on the AP radiograph, and φ is the amount of rotation measured on the LAT radiograph.

Figure 49:
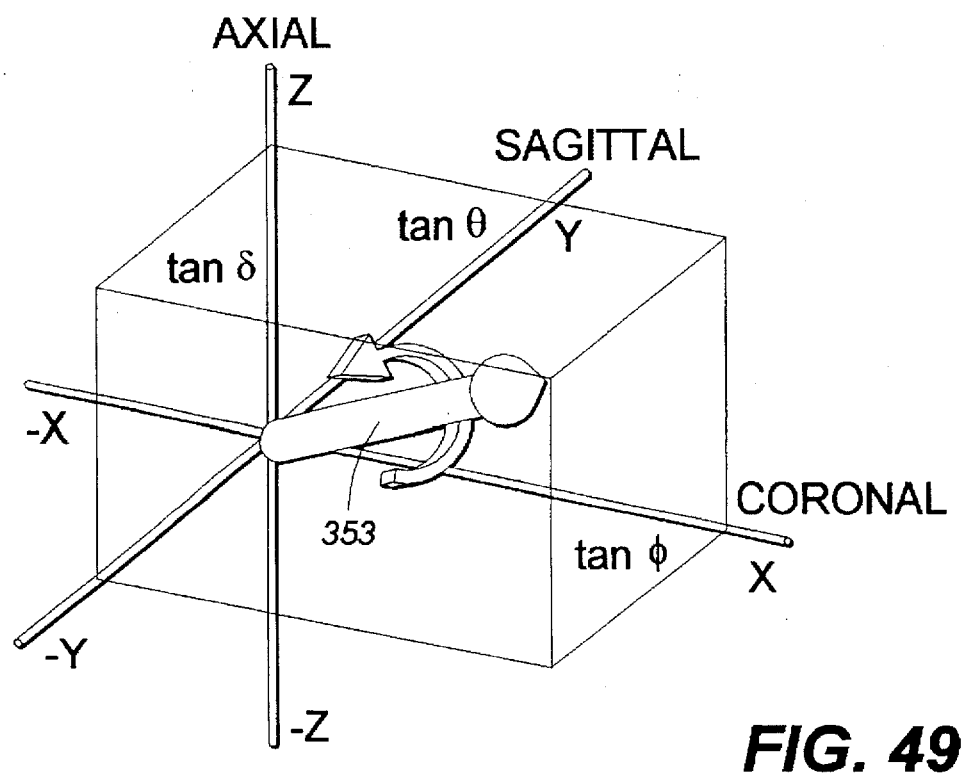
FIG. 49 is an illustration of a vector representation of a Chasles Axis for a three dimensional rotational deformity.

Finally, we consider the most difficult situation where there is a three-dimensional rotational deformity. The amount of rotation is determined from two orthogonal radiographs and a clinical exam for axial malrotation. For each radiograph or clinical exam determine the angle of deformity, take the tan of that angle and plot the value along the reference axis perpendicular to that radiographic plane. Referring now to FIG. 49, the final rotation axis 353 will be the vector sum of the three orthogonal contributions. This Chasles Axis 353 may lie along a reference coordinate axis in special cases, but as illustrated in FIG. 49, the Chasles Axis 353 can exist in any of the eight octants of space as determined by +/− coronal axis, +/− sagittal axis, and +/− vertical axis. The true magnitude of the three-dimensional rotation is:

$$\sigma = A\tan\sqrt{\tan^2\theta + \tan^2\phi + \tan^2\delta}$$

where θ is the amount of rotation measured on the AP radiograph, φ is the amount of rotation measured on the LAT radiograph, and δ is the amount of axial rotation determined from a clinical exam.

By treating the rotation or Chasles Axis as a vector quantity, the surgeon is able to exactly locate this axis in any of eight octants and by invoking the right-hand rule can readily determine direction of rotation about this axis to recreate the deformity. This specificity eliminates the occasional problem of building an Ilizarov fixator as the inverse of what is needed. For example, the hinge axis of a varus/extension deformity is conceivably the same as a valgus/flexion deformity except that the rotations are opposite. The surgeon must roll up his pants leg and continually double check that he is not building the inverse device. Imagine now that the surgeon is also routinely addressing longitudinal malrotation. The difficulty of maintaining proper sign double again.

Once the Chasles Axis (or hinge vector) and the extent of rotation (s) are known, they can be used to create a rotation transformation matrix [R] which exactly duplicates the three angular deformities measured radiographically and clinically. In accordance with the preferred embodiment of the method of the present invention, the matrix that we have found works best was established for the situation of a rotation about an oblique axis where the three angles from the oblique axis to the three orthogonal reference axes are known. The general formula for this matrix is:

$$[R] = \begin{bmatrix} \cos(\sigma) + \\ [(1-\cos(\sigma))*\cos(\alpha)*\cos(\alpha)] & -[\sin(\sigma)*\cos(\gamma)] + \\ [(1-\cos(\sigma))*\cos(\alpha)*\cos(\beta)] & [\sin(\sigma)*\cos(\beta)] + \\ [(1-\cos(\sigma))*\cos(\alpha)*\cos(\alpha)] \\ [\sin(\sigma)*\cos(\gamma)] + \\ [(1-\cos(\sigma))*\cos(\alpha)*\cos(\beta)] & \cos(\sigma) + \\ [(1-\cos(\sigma))*\cos(\beta)*\cos(\beta)] & [-\sin(\sigma)*\cos(\alpha)] + \\ [(1-\cos(\sigma))*\cos(\beta)*\cos(\gamma)] \\ [-\sin(\sigma)*\cos(\beta)] + \\ [(1-\cos(\sigma))*\cos(\alpha)*\cos(\gamma)] & [\sin(\sigma)*\cos(\alpha)] + \\ [(1-\cos(\sigma))*\cos(\beta)*\cos(\gamma)] & \cos(\sigma) + \\ [(1-\cos(\sigma))*\cos(\gamma)*\cos(\gamma)] \end{bmatrix}$$

It should be noted that the three angles that this matrix is based on are the real angles alpha (α) (angle to the x-axis), beta (β) (angle to the y-axis), and gamma (γ) (angle to the z-axis) and not the projection angles theta (θ), phi (φ) and delta (δ) measure on a radiograph and a clinical examination. The three real angles (α, β, γ) can be solved for in terms of the projected angles (θ, φ, δ) as follows:

$$\alpha = A\cos\left(\frac{\tan(\phi)}{\sqrt{\tan(\theta)^2 + \tan(\phi)^2 + \tan(\delta)^2}}\right)$$

$$\beta = A\cos\left(\frac{\tan(\theta)}{\sqrt{\tan(\theta)^2 + \tan(\phi)^2 + \tan(\delta)^2}}\right)$$

$$\gamma = A\cos\left(\frac{\tan(\delta)}{\sqrt{\tan(\theta)^2 + \tan(\phi)^2 + \tan(\delta)^2}}\right)$$

In addition, as previously noted the value of σ is given by the equation:

$$\sigma = A\tan\sqrt{\tan^2\theta + \tan^2\phi + \tan^2\delta}$$

Knowing the three real angles (α, β, γ), and the magnitude of the rotation (σ), the rotation matrix can be solved completely in terms of the projected angles (θ, φ, δ). Thus, if we know the coordinates of three noncollinear points (i.e., for the connectors) on an external fixator base member in the natural or preferred state, using the above rotation matrix, we can determine the new coordinates of those points if the external fixator were to undergo the same angular deformity as the skeleton.

B. Translation Component of the General Deformity Equation

Figure 50:
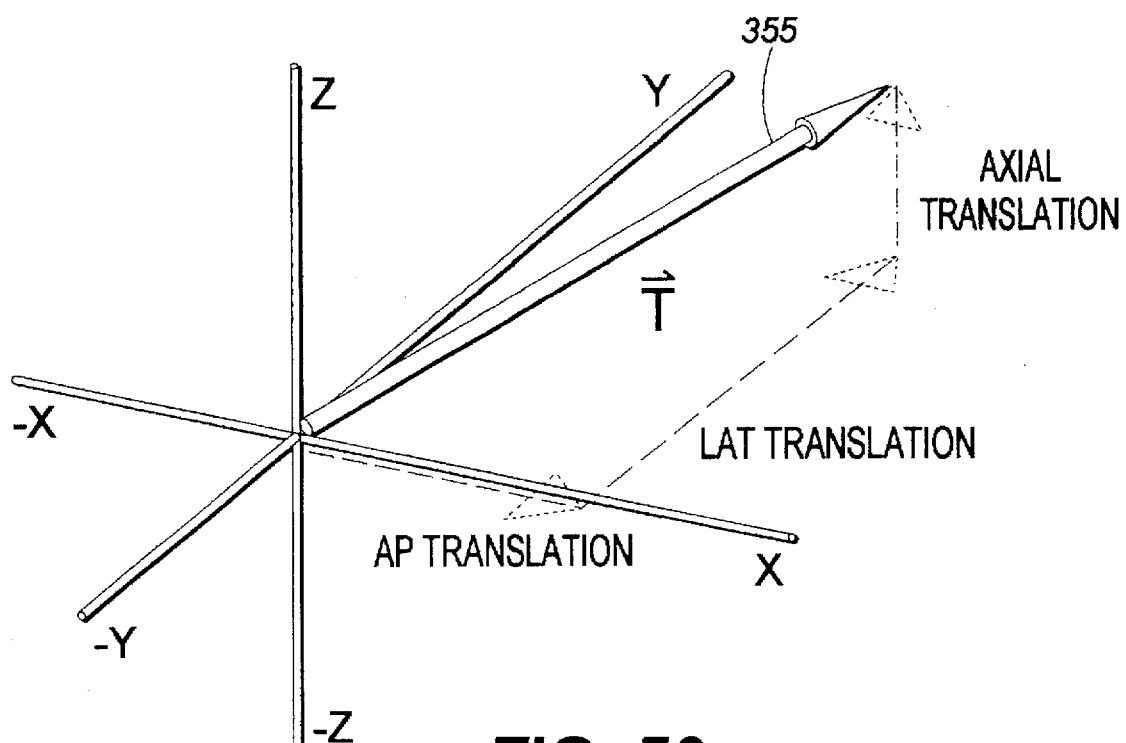
FIG. 50 is perspective view of a translation vector that represents the combined translations that may be corrected in accordance with a preferred method of using the device of the current invention.

The three translations observed radiographically measure the offset of the fragments along the X, Y, and Z axes. As illustrated in FIG. 50, these three translations may be added vectorily to yield the equivalent translation vector 355 [T] that is given by the formula:

$$[T] = \begin{bmatrix} AP\text{ trans} \\ LAT\text{ trans} \\ \text{axial trans} \end{bmatrix}$$

[T] is the translation component of the general deformity equation. The translational contribution to general deformity $$[R] = \begin{bmatrix} \cos(\sigma) + & -[\sin(\sigma)*\cos(\gamma)] + & [\sin(\sigma)*\cos(\beta)] + \\ [(1-\cos(\sigma))*\cos(\alpha)*\cos(\alpha)] & [(1-\cos(\sigma))*\cos(\alpha)*\cos(\beta)] & [(1-\cos(\sigma))*\cos(\alpha)*\cos(\alpha)] \\ [\sin(\sigma)*\cos(\gamma)] + & \cos(\sigma) + & [-\sin(\sigma)*\cos(\alpha)] + \\ [(1-\cos(\sigma))*\cos(\alpha)*\cos(\beta)] & [(1-\cos(\sigma))*\cos(\beta)*\cos(\beta)] & [(1-\cos(\sigma))*\cos(\beta)*\cos(\gamma)] \\ [-\sin(\sigma)*\cos(\beta)] + & [\sin(\sigma)*\cos(\alpha)] + & \cos(\sigma) + \\ [(1-\cos(\sigma))*\cos(\alpha)*\cos(\gamma)] & [(1-\cos(\sigma))*\cos(\beta)*\cos(\gamma)] & [(1-\cos(\sigma))*\cos(\gamma)*\cos(\gamma)] \end{bmatrix}$$

is added after the rotation matrix has been applied to the coordinates of the point being considered. Therefore, the general deformity equation can be represented as follows:

$$[R]\begin{bmatrix} X \\ Y \\ Z \end{bmatrix} + [T] = \begin{bmatrix} X' \\ Y' \\ Z' \end{bmatrix}$$

where [R] is the rotation matrix; X, Y, and Z are the initial ball coordinates for the moving ring; [T] is the translation matrix for the X, Y, Z directions; and X', Y', and Z' are the transformed ball coordinates for the moving ring.

C. Computer/Calculator Program

Figure 6:
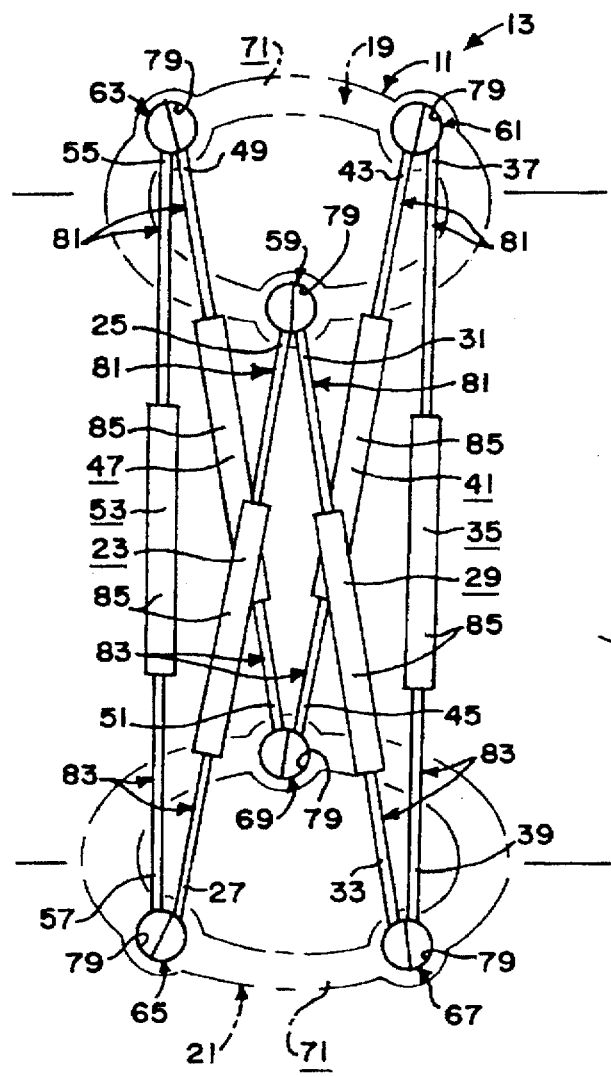
FIG. 6 is a diagrammatic view of the external fixator of FIG. 1 shown in a first spatial arrangement.
Figure 7:
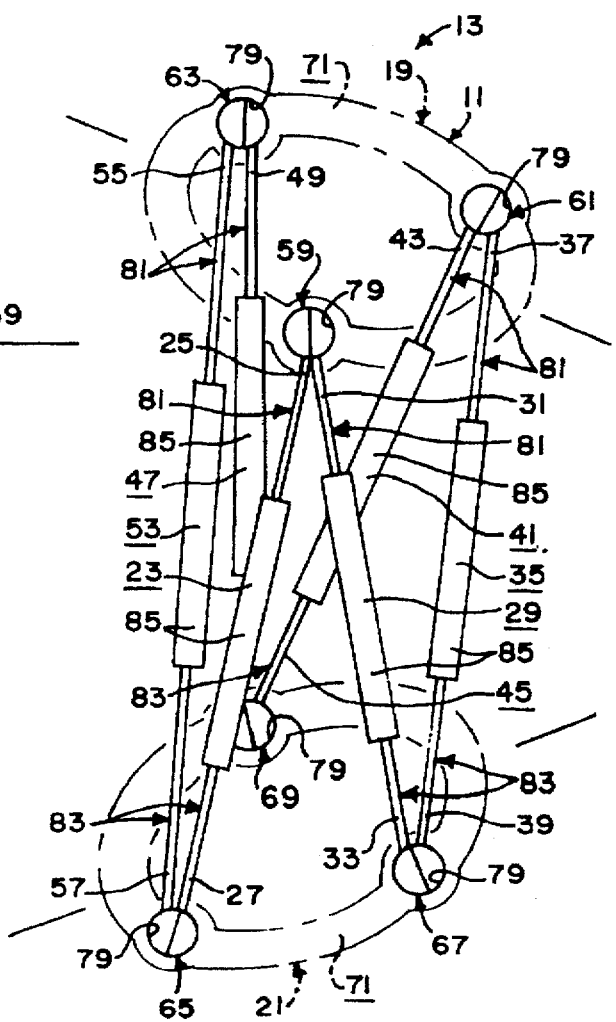
FIG. 7 is a diagrammatic view of the external fixator of FIG. 1 in a second spatial arrangement.

The general deformity equation can be used to develop a computer/calculator program that will provide the strut lengths required to mimic or mirror a deformity. In accordance with a preferred embodiment of the present invention, as illustrated in FIGS. 1 and 6, where the device includes six adjustable struts interconnected with six split ball connectors, the strut lengths are determined as follows.

The positions of the six ring connectors when the device is in its neutral position are first characterized in cylindrical coordinates (r, θ, z). These coordinates are then adjusted for the rotary eccentricity, and the axial eccentricity to yield adjusted connector cylindrical coordinates (r, θ', z'). Next, the Cartesian coordinates for the device connectors when the device is in its neutral position are calculated as follows:

$x = r\cos\theta$
$y = r\sin\theta'$
$z' = z'$

The six connector coordinates are thus characterized in Cartesian coordinates, and have been adjusted for the eccentricities. The neutral device Cartesian coordinates can then be adjusted for the lateral and axial eccentricities to yield adjusted Cartesian coordinates (x', y', z'). We can then construct an array:

$$\begin{vmatrix} x' \\ y' \\ z' \end{vmatrix}$$

for the adjusted Cartesian coordinates of each connector that takes into account the various eccentricities. The connector coordinate arrays of the moving ring are transformed via the rotation matrix:

and provides new coordinates determined by the angular deformity parameters:

$$[R]\begin{vmatrix} x' \\ y' \\ z' \end{vmatrix} = \begin{vmatrix} x'' \\ y'' \\ z'' \end{vmatrix}$$

The translation matrix based on the translations in the deformity is then added to yield the new ball coordinates that will mimic or mirror the deformity:

$$\begin{vmatrix} x'' \\ y'' \\ z'' \end{vmatrix} + \begin{vmatrix} T_x \\ T_y \\ T_z \end{vmatrix} = \begin{vmatrix} x''' \\ y''' \\ z''' \end{vmatrix}$$

Using the pythagorean theorem, the strut lengths required to mimic or mirror the deformity can be determined. For example, if we assume that strut 23 in FIG. 6 is strut 1, and connector 59 is connector 1 and connector 65 is connector 4, and connector 1 is on the moving ring, the length of strut 1 would be determined by the formula:

$$\text{length}_1 = \sqrt{(x'''_1 - x'_4)^2 + (y'''_1 - y'_4)^2 + (z'''_1 - z'_4)^2}$$

This calculation can be repeated for each of the remaining five struts to yield the new strut lengths to mimic the deformity. Similarly, the strut lengths required to mirror the deformity can be determined by simply reversing the direction of the rotation matrix and the translation matrix.

Using the technique outlined above, one of ordinary skill in the art can readily program a computer or calculator to calculate the six strut lengths based on the input of the thirteen variables, including the device parameters, the deformity parameters, and the eccentricities.

VII. Clinical Considerations

A. Compensation for Structures at Risk

It is incumbent upon the surgeon to be aware of the structures at risk on the concavity of the deformity. When dealing with rotation about the longitudinal axis in addition to conventional angular correction, the risks may be less or greater depending on the direction of axial rotation. For example, when correcting a flexion/valgus/external rotati- peroneal nerve is a proximal tibia, the peroneal nerve is at increased risk. However, when correcting a flexion/valgus/ internal rotation deformity, the axial rotation will tend to offset the stretch on the peroneal nerve created during the correction of flexion/valgus.

Figure 51:
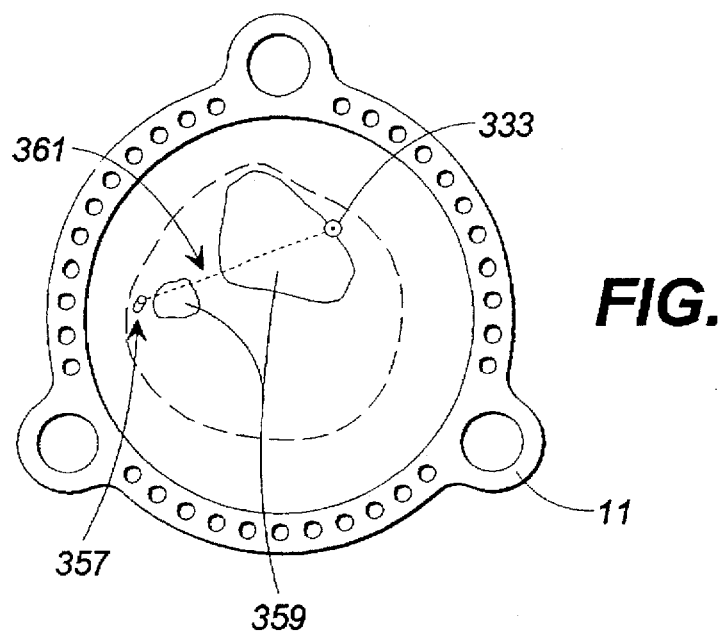
FIG. 51 is a cross-sectional view of the device of the current invention mounted on a tibia, and illustrates the assessment of the risk radius in accordance with a preferred method of using the device of the current invention.

Referring to FIG. 51, a cross section of a tibia 359 is shown with the device 11 of the current invention mounted thereon. In primarily angulated deformities, the distance from the virtual hinge axis (origin) 333 to the structure at risk, such as a peroneal nerve 357, is the risk radius as indicated by the line 361. Knowing the real angle of deformity in degrees ($\sigma$), and the risk radius (r), the extra length needed in the structure at risk to trace the arc segment is given by the equation:

$$\text{arc length} = \frac{2\pi\sigma r}{360}$$

or if the real angle of deformity is expressed in radians, the arc length is given by:

arc length$_{radian}=\sigma r$

The arc length probably overestimates the needed length in most cases, but can be used as the safest determination for length especially if the structure at risk is orbiting a firm mass of scar or bone fragment. The shortest length or chord length between the structure at risk in the deformed state to the normal state is given by:

$$\text{chord length} = 2\, r \sin\frac{\sigma}{2}$$

Alternatively, using the same program which calculates new positions of the connectors of the moving ring, the coordinates of the structure at risk with respect to the origin for a normal bone can be used to determine the coordinates of the structure at risk in the deformed position. The additional length needed for the structure at risk as the deformity is corrected is simply the distance between these two points, solved with the Pythagorean theorem.

B. Rate of Correction

Knowing the distance for correction and a biologically safe velocity, the total number of days required to safely correct the deformity may be determined. Typically the appropriate rate will be 1 mm/day. However, one of ordinary skill in the art can determine what the best rate of correction is for their specific case. Deformity with three axes translation only, has no contribution to displacement by rotation.

The total linear displacement of any point on the moving fragment is given by:

$$\text{Displacement} = \sqrt{(AP\,\text{tran})^2 + (LAT\,\text{tran})^2 + (AX\,\text{tran})^2} \quad \text{OR}$$

$$|\overrightarrow{P-P'}| \text{ OR } |\vec{T}|$$

Using one of the above methods the total displacement of the structure at greatest risk can be determined. This distance divided by the safe velocity will yield the total days until the deformity is corrected.

From their neutral or "0" length, each strut will be adjusted to a new length, which either reproduces or compensates for the deformity. The sum of the absolute values of all new strut lengths represents the total excursion of all struts during the deformity correction. Divide the total strut excursion by the number of days of treatment to obtain the amount of adjustment needed daily. In accordance with the preferred design of the present invention, one complete revolution of the turnbuckle changes the length by 1.6 min.

One method of adjusting struts takes the daily excursion required and divides by 1.6 mm to obtain the number of complete revolutions of turnbuckles daily. Start at strut 1. Make one complete revolution toward "0" (for the chronic technique). Continue to strut 2 etc. until the total number of daily revolutions has been reached. This sequence can be performed throughout the day to achieve divided doses. The next day the patient begins on the next strut in the 1–6 sequence. It is not necessary to turn each strut daily. Once a strut reaches its neutral position it is skipped on the remaining adjustments.

The device can be adjusted toward way points in a similar manner.

C. Clinical Considerations when Correcting a Acute Deformity—Fracture

Fractures should be stabilized with the device in neutral position—i.e., all struts set to neutral or 0 (zero) position. The fragments should be reduced during application in conventional fashion. However, because of the 6-axis correctability of the device of the current invention, an extraarticular fracture could be stabilized blindly and corrected later by adjusting struts gradually, eliminating the need for subsequent anesthesia or device modification.

D. Clinical Considerations when Correcting a Chronic Deformity

Because of nonorthogonal initial radiographs, error in measuring radiographs, or excessive preload and bending of wires and pins, there may still be acute deformity when the struts have reached their neutral lengths. Simply measure the radiographs and make the clinical exam for malrotation and determine the new strut lengths to create a compensating device. This situation is analogous to the acute deformity after fracture stabilization.

E. Way Points

Figure 52:
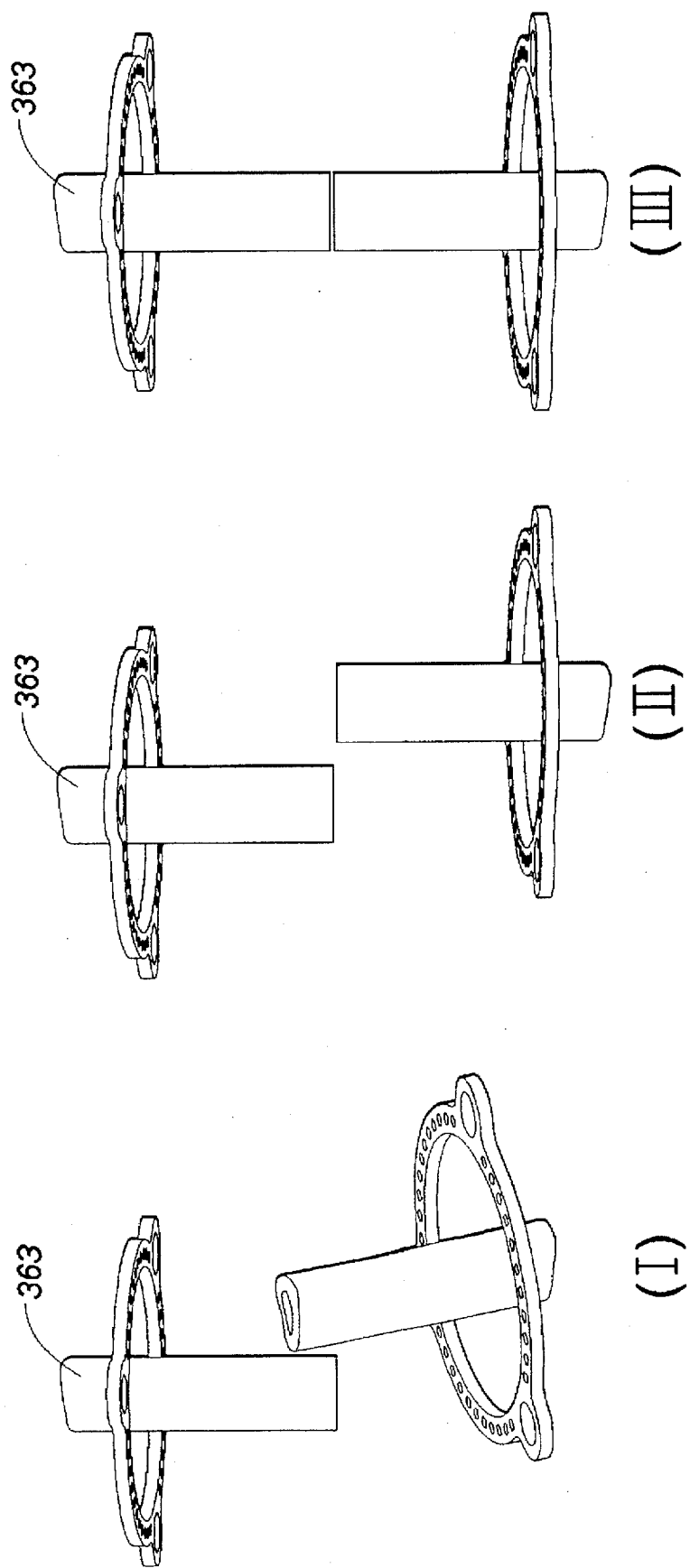
FIG. 52 is a perspective view of the base members of the current device attached to a fracture, and illustrates the use of way points in accordance with a preferred method of using the device of the current invention.

During correction of deformity with significant shortening and bayonet apposition, it is desirable to bring the fragments out to length before undergoing transverse plane translation. To boost patient morale it may also be desirable to correct angular and rotational alignment early. Any number of way points or intermediate points of deformity correction can be established and the exact combination of strut lengths to accomplish the way point determined. Referring to FIG. 52, the use of a way point is illustrated. A deformed bone 363 is shown (I) initially having the deformity parameters ($\theta,\phi,\delta,X,Y,Z$). A way point is shown at position (II) where the deformity parameters are (0,0,0,X, Y,0), and all angulation and axial translation are corrected. These way point parameters can be inserted into the strut length program, and the strut lengths to establish this intermediate position will be provided. The surgeon/patient will first gradually adjust the device to this intermediate position, and then finally adjust the strut lengths to their neutral positions and correct the deformity as shown in step (III).

Although the present invention has been described and illustrated with respect to preferred embodiments thereof and preferred uses therefor, it is not to be so limited since modifications and changes can be made therein which are within the full intended scope of the invention.

We claim:

1. A method of using an external fixation device to reposition a first tissue segment to a predetermined position relative to a second tissue segment, whereby the external fixation device includes a first base member, a second base member, and at least six adjustable-length struts interconnecting said first and second base members through a plurality of connectors, wherein the method comprises the steps of:

(A) attaching said first base member to said first tissue segment;

(B) attaching said second base member to said second tissue segment;

(C) calculating new effective lengths for each of said struts that are required to reposition said first tissue segment to said predetermined position, wherein said calculation includes the steps of:

1) using a mathematical correlation of the relative positions of said first tissue segment, said second tissue segment, and said device to determine new connector locations required to reposition the first tissue segment to said predetermined position; and 2) determining said new effective lengths of said struts based on said new connector locations; and (D) adjusting the effective lengths of said struts to said new effective lengths.

2. The method of claim 1 wherein a deformity exists between said first tissue segment and said second tissue segment and said deformity includes an angulation component, whereby said method further includes the step of characterizing said deformity in terms of at least one projected angle, and said mathematical correlation includes a correlation of the magnitude of the angulation component of said deformity to said projected angle.

3. The method of claim 2 wherein said deformity is characterized in terms of three projected angles, and said mathematical correlation is $$\sigma = A\tan\sqrt{\tan^2\theta + \tan^2\phi + \tan^2\delta}$$

where $\sigma$ is the magnitude of angulation and $\theta$, $\phi$, and $\delta$ are the projected angles.

4. The method of claim 1 wherein said first and second tissue segments include hard tissue and soft tissue.

5. The method of claim 4 wherein said first and second tissue segments are bone.

6. The method of claim 1 wherein said connectors are selected from the group consisting of split ball connectors, ball joint connectors, universal joint connectors, flexible connectors, and elastic connectors.

7. A method of using an external fixation device to correct a tissue deformity between a first tissue segment and a second tissue segment, whereby the external fixation device includes a first base member, a second base member, and a plurality of adjustable-length struts interconnecting said first and second base members through connectors, wherein the method comprises the steps of:

(A) attaching said first base member to said first tissue segment, (B) attaching said second base member to said second tissue segment, (C) defining a hinge axis about which the correction will occur, (D) determining new connector locations if correction occurred about said hinge axis, (E) determining new lengths of the adjustable struts based on said new connector locations, and (F) adjusting the struts to said new lengths.

8. The method of claim 7 wherein the new connector locations are determined from a general deformity equation.

9. The method of claim 8 wherein the general deformity equation includes the rotational matrix given by the formula:

$$[R] = \begin{bmatrix} \cos(\sigma) + \\ [(1-\cos(\sigma))*\cos(\alpha)*\cos(\alpha)] & -[\sin(\sigma)*\cos(\gamma)] + \\ [(1-\cos(\sigma))*\cos(\alpha)*\cos(\beta)] & [\sin(\sigma)*\cos(\beta)] + \\ [(1-\cos(\sigma))*\cos(\alpha)*\cos(\gamma)] \\ [\sin(\sigma)*\cos(\gamma)] + \\ [(1-\cos(\sigma))*\cos(\alpha)*\cos(\beta)] & \cos(\sigma) + \\ [(1-\cos(\sigma))*\cos(\beta)*\cos(\beta)] & [-\sin(\sigma)*\cos(\alpha)] + \\ [(1-\cos(\sigma))*\cos(\beta)*\cos(\gamma)] \\ [-\sin(\sigma)*\cos(\beta)] + \\ [(1-\cos(\sigma))*\cos(\alpha)*\cos(\gamma)] & [\sin(\sigma)*\cos(\alpha)] + \\ [(1-\cos(\sigma))*\cos(\beta)*\cos(\gamma)] & \cos(\sigma) + \\ [(1-\cos(\sigma))*\cos(\gamma)*\cos(\gamma)] \end{bmatrix}$$

10. The method of claim 7 wherein the new lengths of the adjustable struts are determined using the pythagorean theorem.

11. The method of claim 7 wherein said deformity includes an angulation component, and said method further includes the step of characterizing said deformity in terms of at least one projected angle, and determining the new connector locations by mathematically correlating the magnitude of the angulation component of said deformity to said projected angle.

12. The method of claim 11 wherein said deformity is characterized in terms of three projected angles, and said mathematical correlation is $$\sigma = A\tan\sqrt{\tan^2\theta + \tan^2\phi + \tan^2\delta}$$

where $\sigma$ is the magnitude of angulation and $\theta$, $\phi$, and $\delta$ are the projected angles.

13. The method of claim 7 wherein said first and second tissue segments include hard tissue and soft tissue.

14. The method of claim 13 wherein said first and second tissue segments are bone.

15. The method of claim 7 wherein said new lengths are determined using a calculator or computer.

16. The method of claim 7 wherein a safe rate at which the effective lengths of said struts are adjusted to said new effective lengths is determined by the steps including:

(1) determining a total displacement of a structure at greatest risk;

(2) dividing the total displacement by a clinically determined safe correction velocity to yield the total number of days required for correction;

(3) calculating the sum of the absolute value of the difference between each new strut length and its corresponding initial length to provide the total excursion of all struts that is required to correct the deformity; and (4) dividing the total excursion by the total number of days required for correction to obtain said safe rate in terms of an amount of daily adjustment.

17. The method of claim 16 wherein said struts are adjusted to said new effective lengths at said safe rate.

18. The method of claim 7 wherein said device includes from two to eight struts.

19. A method of using an external fixation device to correct a deformity in a tissue having a first tissue segment and a second tissue segment with a deformity site therebetween, whereby the external fixation device includes:

(1) a first base member having a first effective diameter, (2) a second base member having a second effective diameter, (3) a plurality of adjustable-length struts interconnecting said first and second base members with each strut initially having a neutral length that is the same, (4) a first attachment mechanism associated with the first base member, and (5) a second attachment mechanism associated with the second base member, whereby the device has a centerline extending from an effective center of the first base member to an effective center of the second base member; wherein the method comprises:

(A) determining the following measurements of the first tissue segment relative to the second tissue segment:

(1) deformity anterior-posterior displacement, (2) deformity lateral-medial displacement, (3) axial displacement, (4) anterior-posterior angulation, (5) lateral-medial angulation, (6) axial rotation;

(B) determining an origin at the deformity site that will act as a convenient reference point;

(C) predetermining an appropriate location on said first tissue segment for attachment of the first base member to the first tissue segment, said location being characterized by (1) the vertical distance from the first base member to the origin, (2) the horizontal displacement of the origin from the centerline of the device, whereby the horizontal displacement consists of am eccentric anterior-posterior displacement and an eccentric lateral-medial displacement, and (3) a predetermined orientation of the device and the amount said second tissue segment is rotated about its axis from its correct position;

(D) calculating a new effective length of each strut that is required to configure the device to mimic the deformity;

(E) adjusting the effective length of each strut to said new effective length;

(F) attaching the first attachment mechanism to the first tissue segment at the predetermined appropriate location, and attaching the second attachment mechanism to the second tissue segment;

(G) adjusting the effective length of each strut to said initial neutral length, and thereby substantially correcting the deformity.

20. The method of claim 19 wherein said new effective length is calculated from:

(A) said first effective diameter, (B) said second effective diameter, (C) said neutral strut length, (D) said deformity anterior-posterior displacement, (E) said deformity lateral-medial displacement, (F) said axial displacement, (G) said anterior-posterior angulation, (H) said lateral-medial angulation, (I) said axial rotation, (J) said vertical distance from the first base member to the origin, (K) said eccentric anterior-posterior displacement, (L) said eccentric lateral-medial displacement, and (M) said amount the second tissue segment is rotated about its axis from its correct position.

21. The method of claim 19 wherein said deformity includes an angulation component, and the new effective lengths are calculated by a method including the steps of: (A) characterizing said deformity in terms of three projected angle; and (B) mathematically correlating said angulation component of said deformity to said projected angles by the equation:

$$\sigma = A\tan \sqrt{\tan^2\theta + \tan^2\phi + \tan^2\delta}$$

where $\sigma$ is the magnitude of said angulation and $\theta$, $\phi$, and $\delta$ are the projected angles.

22. The method of claim 19 wherein a safe rate at which the effective lengths of said struts are adjusted from said new effective lengths to said initial neutral length is determined by the steps including:

(1) determining a total displacement of a structure at greatest risk;

(2) dividing the total displacement by a clinically determined safe correction velocity to yield the total number of days required for correction;

(3) calculating the sum of the absolute value of the difference between each new strut length and its corresponding initial length to provide the total excursion of all struts that is required to correct the deformity; and (4) dividing the total excursion by the total number of days required for correction to obtain said safe rate in terms of an amount of daily adjustment.

23. The method of claim 22 wherein said struts are adjusted to said initial neutral effective length at said safe rate.

24. The method of claim 19 wherein said plurality of adjustable-length struts interconnect said first and second base members through connectors, and said new effective length of each strut is calculated by the steps comprising:

(A) determining new connector locations from a general deformity equation that includes the rotational matrix given by the formula:

$$[R] = \begin{bmatrix} \cos(\sigma) + & -[\sin(\sigma)*\cos(\gamma)] + & [\sin(\sigma)*\cos(\beta)] + \\ [(1-\cos(\sigma))*\cos(\alpha)*\cos(\alpha)] & [(1-\cos(\sigma))*\cos(\alpha)*\cos(\beta)] & [(1-\cos(\sigma))*\cos(\alpha)*\cos(\gamma)] \\ [\sin(\sigma)*\cos(\gamma)] + & \cos(\sigma) + & [-\sin(\sigma)*\cos(\alpha)] + \\ [(1-\cos(\sigma))*\cos(\alpha)*\cos(\beta)] & [(1-\cos(\sigma))*\cos(\beta)*\cos(\beta)] & [(1-\cos(\sigma))*\cos(\beta)*\cos(\gamma)] \\ [-\sin(\sigma)*\cos(\beta)] + & [\sin(\sigma)*\cos(\alpha)] + & \cos(\sigma) + \\ [(1-\cos(\sigma))*\cos(\alpha)*\cos(\gamma)] & [(1-\cos(\sigma))*\cos(\beta)*\cos(\gamma)] & [(1-\cos(\sigma))*\cos(\gamma)*\cos(\gamma)] \end{bmatrix}$$

and (B) determining the new lengths of the adjustable struts that interconnect the connectors if said connectors were positioned at said new connector locations.

25. A method of using an external fixation device to correct a deformity in a tissue having a first tissue segment and a second tissue segment with a deformity site therebetween, whereby the external fixation device includes:

(1) a first base member having a first effective diameter,
   (2) a second base member having a second effective diameter,
   (3) a plurality of adjustable-length struts interconnecting said first and second base members with each strut initially having a neutral length that is the same,
   (4) a first attachment mechanism associated with the first base member, and
   (5) a second attachment mechanism associated with the second base member, whereby the device has a centerline extending from an effective center of the first base member to an effective center of the second base member;

wherein the method comprises:

(A) attaching the first attachment mechanism to the first tissue segment, and attaching the second attachment mechanism to the second tissue segment;
   (B) determining the following measurements of the first tissue segment relative to the second tissue segment:
      (1) deformity anterior-posterior displacement,
      (2) deformity lateral-medial displacement,
      (3) axial displacement,
      (4) anterior-posterior angulation,
      (5) lateral-medial angulation,
      (6) axial rotation;
   (c) determining an origin at the deformity site that will act as a convenient reference point;
   (D) characterizing the location of the first tissue segment relative to the first base member in terms of
      (1) the vertical distance from the first base member to the origin,
      (2) the horizontal displacement of the origin from the centerline of the device, whereby the horizontal displacement consists of an eccentric anterior-posterior displacement and an eccentric lateral-medial displacement, and
      (3) a predetermined orientation of the device and the amount the second tissue segment is rotated about its axis from its correct position;
   (E) calculating new effective lengths for each strut that is required to configure the device to mirror the deformity;
   (F) adjusting each strut to its new effective length to configure the device to mirror the deformity, and thereby substantially correcting the deformity.

26. The method of claim 25 wherein said new effective lengths is calculated from:

(A) said first effective diameter,
   (B) said second effective diameter,
   (C) said neutral strut length,
   (D) said deformity anterior-posterior displacement,
   (E) said deformity lateral-medial displacement,
   (F) said axial displacement,
   (G) said anterior-posterior angulation,
   (H) said lateral-medial angulation,
   (I) said axial rotation,
   (J) said vertical distance from the first base member to the origin,
   (K) said eccentric anterior-posterior displacement,
   (L) said eccentric lateral-medial displacement, and
   (M) said amount the second tissue segment is rotated about its axis from its correct position.

27. The method of claim 25 wherein said deformity includes an angulation component, and the new effective lengths are calculated by a method including the steps of: (A) characterizing said deformity in terms of three projected angle; and (B) mathematically correlating said angulation component of said deformity to said projected angles by the equation:

$$\sigma = A\tan\sqrt{\tan^2\theta + \tan^2\phi + \tan^2\delta}$$

where $\sigma$ is the magnitude of said angulation and $\theta$, $\phi$, and $\delta$ are the projected angles.

28. The method of claim 25 wherein a safe rate at which the effective lengths of said struts are adjusted to said new effective lengths is determined by the steps including:

(1) determining a total displacement of a structure at greatest risk;
   (2) dividing the total displacement by a clinically determined safe correction velocity to yield the total number of days required for correction;
   (3) calculating the sum of the absolute value of the difference between each new strut length and its corresponding initial length to provide the total excursion of all struts that is required to correct the deformity; and
   (4) dividing the total excursion by the total number of days required for correction to obtain said safe rate in terms of an amount of daily adjustment.

29. The method of claim 28 wherein said struts are adjusted to said new effective lengths at said safe rate.

30. The method of claim 25 wherein said plurality of adjustable-length struts interconnect said first and second base members through connectors, and said new effective length of each strut is calculated by the steps comprising:

(A) determining new connector locations from a general deformity equation that includes the rotational matrix given by the formula:

$$[R] = \begin{bmatrix} \cos(\sigma) + & -[\sin(\sigma)*\cos(\gamma)] + & [\sin(\sigma)*\cos(\beta)] + \\ [(1-\cos(\sigma))*\cos(\alpha)*\cos(\alpha)] & [(1-\cos(\sigma))*\cos(\alpha)*\cos(\beta)] & [(1-\cos(\sigma))*\cos(\alpha)*\cos(\gamma)] \\ [\sin(\sigma)*\cos(\gamma)] + & \cos(\sigma) + & [-\sin(\sigma)*\cos(\alpha)] + \\ [(1-\cos(\sigma))*\cos(\alpha)*\cos(\beta)] & [(1-\cos(\sigma))*\cos(\beta)*\cos(\beta)] & [(1-\cos(\sigma))*\cos(\beta)*\cos(\gamma)] \\ [-\sin(\sigma)*\cos(\beta)] + & [\sin(\sigma)*\cos(\alpha)] + & \cos(\sigma) + \\ [(1-\cos(\sigma))*\cos(\alpha)*\cos(\gamma)] & [(1-\cos(\sigma))*\cos(\beta)*\cos(\gamma)] & [(1-\cos(\sigma))*\cos(\gamma)*\cos(\gamma)] \end{bmatrix}$$

and (B) determining the new lengths of the adjustable struts that interconnect the connectors if said connectors were positioned at said new connector locations.

31. A method of using an external fixation device to correct a deformity in a bone having a first bone segment and a second bone segment with a deformity site therebetween, whereby the external fixation device includes:

(1) a first base member having a first effective diameter, (2) a second base member having a second effective diameter, (3) a plurality of adjustable-length struts interconnecting said first and second base members through a plurality of connectors, wherein each strut initially has a neutral length that is the same, (4) a first attachment mechanism associated with the first base member, and (5) a second attachment mechanism associated with the second base member, whereby the device has a centerline extending from an effective center of the first base member to an effective center of the second base member;

wherein the method comprises:

(A) determining the following measurements of the first bone segment relative to the second bone segment:
  (1) deformity anterior-posterior displacement,
  (2) deformity lateral-medial displacement,
  (3) axial displacement,
  (4) anterior-posterior angulation,
  (5) lateral-medial angulation,
  (6) axial rotation;

(B) determining an origin at the deformity site that will act as a convenient reference point;

(C) characterizing the location or anticipated location of said first bone segment relative to said device in terms of
  (1) the vertical distance from the first base member to the origin,
  (2) the horizontal displacement of the origin from the centerline of the device, whereby the horizontal displacement consists of an eccentric anterior-posterior displacement and an eccentric lateral-medial displacement, and
  (3) a predetermined orientation of the device and the amount the second bone segment is rotated about its axis from its correct position;

(D) calculating new effective lengths for each strut by
  (1) determining new connector locations from a general deformity equation that includes the rotational matrix given by the formula:

$$[R] = \begin{bmatrix} \cos(\sigma) + & -[\sin(\sigma)*\cos(\gamma)] + & [\sin(\sigma)*\cos(\beta)] + \\ [(1-\cos(\sigma))*\cos(\alpha)*\cos(\alpha)] & [(1-\cos(\sigma))*\cos(\alpha)*\cos(\beta)] & [(1-\cos(\sigma))*\cos(\alpha)*\cos(\gamma)] \\ [\sin(\sigma)*\cos(\gamma)] + & \cos(\sigma) + & [-\sin(\sigma)*\cos(\alpha)] + \\ [(1-\cos(\sigma))*\cos(\alpha)*\cos(\beta)] & [(1-\cos(\sigma))*\cos(\beta)*\cos(\beta)] & [(1-\cos(\sigma))*\cos(\beta)*\cos(\gamma)] \\ [-\sin(\sigma)*\cos(\beta)] + & [\sin(\sigma)*\cos(\alpha)] + & \cos(\sigma) + \\ [(1-\cos(\sigma))*\cos(\alpha)*\cos(\gamma)] & [(1-\cos(\sigma))*\cos(\beta)*\cos(\gamma)] & [(1-\cos(\sigma))*\cos(\gamma)*\cos(\gamma)] \end{bmatrix}$$

and (2) determining the new lengths of the adjustable struts that interconnect the connectors if said connectors were positioned at said new connector locations; and (E) adjusting the length said struts to said new effective lengths.

32. The method of claim 31 wherein said deformity includes an angulation component, and the new effective lengths are calculated by a method including the steps of: (A) characterizing said deformity in terms of three projected angle; and (B) mathematically correlating said angulation component of said deformity to said projected angles by the equation:

$$\sigma = A\tan\sqrt{\tan^2\theta + \tan^2\phi + \tan^2\delta}$$

where $\sigma$ is the magnitude of said angulation and $\theta$, $\phi$, and $\delta$ are the projected angles.

33. The method of claim 31 wherein a safe rate at which the effective lengths of said struts are adjusted to said new effective lengths is determined by the steps including:

(1) determining a total displacement of a structure at greatest risk;

(2) dividing the total displacement by a clinically determined safe correction velocity to yield the total number of days required for correction;

(3) calculating the sum of the absolute value of the difference between each new strut length and its corresponding initial length to provide the total excursion of all struts that is required to correct the deformity; and (4) dividing the total excursion by the total number of days required for correction to obtain said safe rate in terms of an amount of daily adjustment;

wherein said struts are adjusted to said new effective lengths at said safe rate.

34. A method of using an external fixation device to reposition a first tissue segment to a predetermined position relative to a second tissue segment, whereby the external fixation device includes a first base member, a second base member, and at least six adjustable-length struts interconnecting said first and second base members, wherein the method comprises the steps of:

(A) attaching said first base member to said first tissue segment;

(B) attaching said second base member to said second tissue segment;

(C) calculating new effective lengths for each of said struts that are required to reposition said first tissue segment to said predetermined position, wherein said calculation is based on a mathematical correlation of the relative positions of said first tissue segment, said second tissue segment, and said device; and (D) adjusting the effective lengths of said struts to said new effective lengths.

35. The method set forth in claim 34 wherein a location of said first tissue segment relative to said second tissue segment is mathematically correlated to a length of at least one of said struts, and a desired positioning of said first tissue segment relative to said second tissue segment is achieved by adjusting at least one of said struts to a new length derived from said mathematical correlation.

36. The method of claim 34 wherein the length of at least one of said struts is adjusted to configure the device to mimic the deformity before the first base member is attached to the first tissue segment.

37. The method of claim 34 wherein the length of at least one of said struts is adjusted to configure the device to mirror the deformity after the first base member is attached to the first tissue segment and the second base member is attached to the second tissue segment.

38. The method of claim 34 wherein a deformity exists between said first tissue segment and said second tissue segment wherein said deformity includes an angulation component, and said method further includes the step of characterizing said deformity in terms of at least one projected angle, and said mathematical correlation includes a correlation of the magnitude of the angulation component of said deformity to said projected angle.

39. The method of claim 38 wherein said deformity is characterized in terms of three projected angles, and said mathematical correlation is $$\sigma = A\tan\sqrt{\tan^2\theta + \tan^2\phi + \tan^2\delta}$$

where $\sigma$ is the magnitude of angulation and $\theta$, $\phi$, and $\delta$ are the projected angles.

40. The method of claim 34 wherein said mathematical correlation includes a rotational matrix component and a translational vector component.

41. The method of claim 40 wherein said fixation device includes six adjustable struts and said rotational matrix component is:

$$[R] = \begin{bmatrix} \cos(\sigma) + & -[\sin(\sigma)*\cos(\gamma)] + & [\sin(\sigma)*\cos(\beta)] + \\ [(1-\cos(\sigma))*\cos(\alpha)*\cos(\alpha)] & [(1-\cos(\sigma))*\cos(\alpha)*\cos(\beta)] & [(1-\cos(\sigma))*\cos(\alpha)*\cos(\gamma)] \\ [\sin(\sigma)*\cos(\gamma)] + & \cos(\sigma) + & [-\sin(\sigma)*\cos(\alpha)] + \\ [(1-\cos(\sigma))*\cos(\alpha)*\cos(\beta)] & [(1-\cos(\sigma))*\cos(\beta)*\cos(\beta)] & [(1-\cos(\sigma))*\cos(\beta)*\cos(\gamma)] \\ [-\sin(\sigma)*\cos(\beta)] + & [\sin(\sigma)*\cos(\alpha)] + & \cos(\sigma) + \\ [(1-\cos(\sigma))*\cos(\alpha)*\cos(\gamma)] & [(1-\cos(\sigma))*\cos(\beta)*\cos(\gamma)] & [(1-\cos(\sigma))*\cos(\gamma)*\cos(\gamma)] \end{bmatrix}$$

and said translational vector component is:

$$[T] = \begin{bmatrix} AP \text{ trans} \\ LAT \text{ trans} \\ \text{axial trans} \end{bmatrix}$$

42. The method of claim 34 wherein said first and second tissue segments include hard tissue and soft tissue.

43. The method of claim 42 wherein said first and second tissue segments are bone.

44. The method of claim 34 wherein said new length is determined using a calculator or computer.

45. The method of claim 34 wherein said struts have initial effective lengths defined by the effective lengths prior to the adjustment to said new effective lengths, wherein said initial effective lengths of the struts are not all the same and the new effective lengths of the struts are not all the same.

46. The method of claim 34 wherein said device includes an automatic adjustment mechanism and said struts are automatically adjusted to said new effective lengths by said automatic adjustment mechanism.

47. The method of claim 34 wherein a safe rate at which the effective lengths of said struts are adjusted to said new effective lengths is determined by the steps including:

(1) determining a total displacement of a structure at greatest risk;

(2) dividing the total displacement by a clinically determined safe correction velocity to yield the total number of days required for correction;

(3) calculating the sum of the absolute value of the difference between each new strut length and its corresponding initial length to provide the total excursion of all struts that is required to correct the deformity; and (4) dividing the total excursion by the total number of days required for correction to obtain said safe rate in terms of an amount of daily adjustment.

48. The method of claim 47 wherein said struts are adjusted to said new effective lengths at said safe rate.

49. The method of claim 34, wherein both said first tissue segment and said second tissue segment are repositioned upon adjustment of the effective lengths of said struts.

* * * * *